United States Patent [19]

Nohr et al.

[11] Patent Number: 5,120,888
[45] Date of Patent: Jun. 9, 1992

[54] SURFACE-SEGREGATABLE, MELT-EXTRUDABLE THERMOPLASTIC COMPOSITION

[75] Inventors: Ronald S. Nohr, Roswell; J. Gavin MacDonald, Decatur, both of Ga.

[73] Assignee: Kimberly-Clark Corporation, Neenah, Wis.

[21] Appl. No.: 720,569

[22] Filed: Jun. 25, 1991

Related U.S. Application Data

[62] Division of Ser. No. 466,556, Jan. 17, 1990, Pat. No. 5,057,262, which is a division of Ser. No. 181,359, Apr. 14, 1988, Pat. No. 4,923,914.

[51] Int. Cl.$^5$ .............................................. C08K 5/34
[52] U.S. Cl. ........................................ 524/99; 524/91;
524/100; 524/265; 428/447; 525/100; 525/104;
525/105; 525/106; 525/343; 525/398; 525/416;
525/446; 525/464; 525/474; 525/431
[58] Field of Search .................. 524/99, 91, 100, 265;
525/100, 104, 105, 106, 393, 398, 416, 446, 464,
474, 431; 428/447

[56] References Cited

U.S. PATENT DOCUMENTS

| | | | |
|---|---|---|---|
| Re. 32,514 | 10/1987 | Steklenski | 524/32 |
| 3,360,421 | 12/1967 | Sands | 161/63 |
| 3,629,308 | 12/1271 | Bailey et al. | 260/448.2 |
| 3,766,115 | 10/1973 | Sands | 260/29.1 |
| 3,867,188 | 2/1975 | Campbell et al. | 117/138.8 |
| 3,929,509 | 12/1975 | Taskier | 136/146 |
| 3,973,068 | 8/1976 | Weber | 28/198 |
| 4,070,218 | 1/1978 | Weber | 156/167 |
| 4,105,569 | 8/1978 | Crossfield | 252/8.6 |
| 4,150,013 | 4/1979 | Punderson | 260/42.26 |
| 4,426,203 | 1/1984 | Abel et al. | 8/138 |
| 4,444,563 | 4/1984 | Abel | 8/588 |
| 4,446,090 | 5/1984 | Lovgren et al. | 264/211 |
| 4,480,009 | 10/1984 | Berger | 428/447 |
| 4,499,149 | 2/1985 | Berger | 428/447 |
| 4,500,659 | 2/1985 | Kroupa et al. | 523/213 |
| 4,535,113 | 8/1985 | Foster et al. | 524/262 |
| 4,563,190 | 1/1986 | Topfl | 8/524 |
| 4,578,414 | 3/1986 | Sawyer et al. | 524/310 |
| 4,585,830 | 4/1986 | Sweet | 524/862 |

(List continued on next page.)

FOREIGN PATENT DOCUMENTS

| | | |
|---|---|---|
| 1049682 | 8/1975 | Canada . |
| 0071349A2 | 2/1982 | European Pat. Off. . |
| 0124347A1 | 11/1984 | European Pat. Off. . |
| 0152883A3 | 8/1985 | European Pat. Off. . |

OTHER PUBLICATIONS

A. J. Savia and R. B. Metzler, *Nonwovens Ind.*, 14, 16 (1983).

[57] ABSTRACT

A surface-segregatable, melt-extrudable thermoplastic composition suitable for processing by melt extrusion to form a fiber or film having a differential, increasing concentration of an additive from the center of the fiber or film to the surface thereof, which differential, increasing concentration imparts to the surface of the fiber or film at least one desired characteristic which otherwise would not be present, which composition includes at least one thermoplastic polymer and at least one defined additive. During formation of the fiber or film, the additive rapidly segregates in a controllable manner toward the newly-formed surface of the fiber or film, thereby resulting in a controllable differential concentration of the polymeric material, which concentration increases with increasing distance from the center of the fiber or film to its surface. The weight ratio of the polymer to the additive is in the range of from about 1 to about 1,000. The preferred polymer is a polyolefin such as polyethylene and polypropylene.

The thermoplastic composition is useful in the preparation of fibers or films which have at least one surface characteristic which is different from that of the polymer component of the thermoplastic composition. The thermoplastic composition is particularly useful in the formation of nonwoven webs which are used in the construction of such disposable absorbent products as diapers, feminine care products, incontinence products, and the like.

7 Claims, 9 Drawing Sheets

U.S. PATENT DOCUMENTS

| | | | |
|---|---|---|---|
| 4,645,691 | 2/1987 | Ona et al. | 427/180 |
| 4,652,489 | 3/1987 | Crass et al. | 428/337 |
| 4,659,777 | 4/1987 | Riffle et al. | 525/100 |
| 4,672,005 | 6/1987 | Dyer | 428/474.4 |
| 4,698,388 | 10/1987 | Ohmura et al. | 525/88 |
| 4,923,914 | 5/1990 | Nohr et al. | 524/99 |

*Chem. Abstr.*, 84:91066z (1976).

*Chem. Abstr.*, 77:89559z (1972).

R. H. Somani and M. T. Shaw, *Macromolecules*, 14, 886 (1981).

S. N. Pandit et al., *Polymer Compos.*, 2, 68 (1981).

"SILWET® Surface Active Copolymers", Bulletin SUI-394A, 7/85-5M, Union Carbide Corporation.

"Silicon Compounds Register and Review", Petrarch Systems Silanes and Silicones, pp. 253-300, Petrarch Systems.

"TEGOPREN® Silicone Surfactants—Products, Data, Information", Th. Goldschmidt AG.

"Surfactants at Th. Goldschmidt AG", Th. Goldschmidt AG.

"Goldschmidt informiert...", 1/82, No. 56, Mar. 1982, English Edition, Th. Goldschmidt AG.

"Goldschmidt informiert...", 4/84, No. 63, Dec. 1984, Functional Oligomers, Th. Goldschmidt AG.

"SILWET® Surfactants", Bulletin SC-877, P8-2538, 2/88-10M, Union Carbide Corporation.

*Primary Examiner*—Melvyn I. Marquis
*Attorney, Agent, or Firm*—William E. Maycock

SURFACE-SEGREGATABLE, MELT-EXTRUDABLE THERMOPLASTIC COMPOSITION

This is a divisional application of application Ser. No. 07/466,556, filed on Jan. 17, 1990, now U.S. Pat. No. 5,057,262, which is a divisional application of application Ser. No. 07/181,359, filed on Apr. 14, 1988, now U.S. Pat. No. 4,923,914.

CROSS-REFERENCES TO RELATED APPLICATIONS

Novel benzotriazolyl-substituted polysiloxanes useful as additives in the surface-segregatable, melt-extrudable thermoplastic compositions of the present invention are described and claimed in copending and commonly assigned application Ser. No. 07/181,624, entitled BENZOTRIAZOLYL-SUBSTITUTED POLYSILOXANES, filed Apr. 14, 1988 in the names of Ronald S. Nohr, J. Gavin MacDonald, and William E. Maycock, now abandoned. Novel 2,2,6,6-tetraalkylpiperidyl-substituted polysiloxanes, also useful as additives in the surface-segregatable, melt-extrudable thermoplastic compositions of the present invention, are described and claimed in copending and commonly assigned application Ser. No. 07/181,623, entitled TETRAALKYL-PIPERIDYL-SUBSTITUTED POLYSILOXANES, filed Apr. 14, 1988 in the names of Ronald S. Nohr, J. Gavin MacDonald, and William E. Maycock, now abandoned. Novel siloxanes containing at least one benzotriazolyl/tetraalkylpiperidyl substituent which are useful as additives in the surface-segregatable, melt-extrudable thermoplastic compositions of the present invention are described and claimed in copending and commonly assigned application Ser. No. 07/181,463, entitled SILOXANE CONTAINING BENZOTRIAZOLYL/TETRAALKYLPIPERIDYL SUBSTITUENT, filed Apr. 14, 1988 in the names of William E. Maycock, Ronald S. Nohr, and J. Gavin MacDonald, now U.S. Pat. No. 4,859,759. A method of stabilizing the compositions of the present invention under melt-extrusion conditions, and the stabilized compositions, are described and claimed in copending and commonly assigned application Ser. No. 07/181,352, entitled STABILIZED SILOXANE-CONTAINING MELT-EXTRUDABLE THERMOPLASTIC COMPOSITIONS, filed Apr. 14, 1988 in the names of Ronald S. Nohr and J. Gavin MacDonald, now U.S. Pat. No. 4,920,168. The use, described herein, of a post-formation, gentle heat treatment in the formation of nonwoven webs from the compositions of the present invention is described and claimed in copending and commonly assigned application Ser. No. 07/181,282, entitled METHOD OF FORMING A NONWOVEN WEB FROM SURFACE-SEGREGATABLE THERMOPLASTIC COMPOSITIONS, filed Apr. 14, 1988 in the names of Ronald S. Nohr and J. Gavin MacDonald, now U.S. Pat. No. 4,857,251. The use, also described herein, of a heated compaction roll in the formation of spunbonded webs from the compositions of the present invention is described and claimed in copending and commonly assigned application Ser. No. 07/181,601, entitled METHOD OF FORMING A SPUNBONDED NONWOVEN WEB FROM SURFACE-SEGREGATABLE THERMOPLASTIC COMPOSITIONS, filed Apr. 14, 1988 in the names of Ronald S. Nohr and J. Gavin MacDonald, now abandoned.

BACKGROUND OF THE INVENTION

The present invention relates to a surface-segregatable, melt-extrudable thermoplastic composition. More particularly, the present invention relates to a thermoplastic composition which rapidly surface segregates in a controllable manner upon melt extrusion to form fibers and films having modified surface characteristics. The surface-segregatable, melt-extrudable thermoplastic composition comprises at least one thermoplastic polymer and at least one defined additive which preferably will contain at least one tetrasubstituted disiloxanylene group.

Polymers are used widely throughout the world to make a variety of products which include blown and cast films, extruded sheets, injection molded articles, foams, blow molded articles, extruded pipe, monofilaments, and nonwoven webs. Some of such polymers, such as polyolefins, are naturally hydrophobic, and for many uses this property is either a positive attribute or at least not a disadvantage.

There are a number of uses for polyolefins, however, where their hydrophobic nature either limits their usefulness or requires some effort to modify the surface characteristics of the shaped articles made therefrom. By way of example, polyolefins are used to manufacture nonwoven webs which are employed in the construction of such disposable absorbent articles as diapers, feminine care products, incontinence products, and the like. Frequently, such nonwoven webs need to be wettable. Wettability can be obtained by spraying or coating the web with a surfactant solution during or after its formation. The web then must be dried, and the surfactant which remains on the web is removed upon exposure of the web to aqueous media. Alternatively, a surfactant can be included in the polymer which is to be melt-processed, as disclosed in U.S. Pat. Nos. 3,973,068 and 4,070,218 to R. E. Weber. In that case, however, the surfactant must be forced to the surface of the fibers from which the web is formed. This typically is done by heating the web on a series of steam-heated rolls or "hot cans". This process, called "blooming", is expensive and still has the disadvantage of ready removal of the surfactant by aqueous media. Moreover, the surfactant has a tendency to migrate back into the fiber which adversely affects shelf life, particularly at high storage temperatures. In addition, it is not possible to incorporate in the polymer levels of surfactant much above 1 percent by weight because of severe processability problems; surfactant levels at the surface appear to be limited to a maximum of about 0.33 percent by weight. Most importantly, the blooming process results in web shrinkage in the cross-machine direction and a significant loss in web tensile strength.

Other methods of imparting wettability to, or otherwise affecting the surface characteristics of, shaped articles made from polyolefins and other hydrophobic polymers are known. Representative examples of a number of such methods are described in the paragraphs which follow.

U.S. Pat. No. 4,578,414 to L. H. Sawyer and G. W. Knight describes wettable olefin polymer fibers. The fibers are formed from a composition comprising a polyolefin resin and one or more defined surface-active agents. Such agents may be present in an amount of from about 0.01 to about 5 percent by weight. The surface-active agents can be (1) an alkoxylated alkyl phenol in combination with a mixed mono-, di-, and/or triglyceride; (2) or a polyoxyalkylene fatty acid ester; or (3) a combination of (2) with any part of (1). The preferred polyolefin is polyethylene, and all of the examples employed an ethylene/1-octene copolymer, the latter apparently being a minor component. The surface-active agents are stated to bloom to the fabricated fiber surfaces where at least one of the surface-active agents remains partially embedded in the polymer matrix. The patent further states that the permanence of wettability can be controlled through the composition and concentration of the additive package.

Polysiloxane/polyoxazoline block copolymers are disclosed in U.S. Pat. No. 4,659,777 to J. S. Riffle and I. Yilgor. The copolymers are stated to be useful as surface-modifying additives for base polymers. Such use apparently has primary reference to personal care products where the surface properties to be imparted include glossiness, smoothness, and lubricity. However, incorporation of the copolymers into fibers is stated to impart surface stain resistance, antistatic properties, flame retardancy, and wettability by both polar and nonpolar solvents. Such incorporation preferably is in the range of from about 1 to 5 parts by weight. Suitable base polymers include some vinyl polymers, acrylate polymers, polyurethanes, cellulose derivatives, and polyethylene, polypropylene, ethylenepropylene copolymers, and copolymers of ethylene with, for example, vinyl acetate. However, the single example illustrating incorporation of the disclosed copolymers into a base polymer employed as the base polymer poly(vinyl chloride), and the resulting mixture was used to cast films from solution.

U.S. Pat. No. 4,672,005 to M. E. Dyer describes a process for improving the hygroscopic, soil release, and other surface properties of a polymer substrate. The process involves contacting the substrate with an aqueous mixture containing a water-soluble vinyl monomer and a hydrophobic vinyl monomer. Polymerization of the water-soluble vinyl monomer then is initiated by a polymerization initiator, thereby forming a vinyl polymer on the surface of the polymer substrate.

U.S. Pat. No. 4,698,388 to H. Ohmura et al. describes a method for modifying the surface of a polymer material by means of a block copolymer. The block copolymer consists of a hydrophilic polymer portion formed from a vinyl monomer and a polymer portion which is compatible with the polymer material, also formed from a vinyl monomer. The block copolymer is added to the polymer material by, for example, coating the material with a solution or suspension of the block copolymer, mixing the block copolymer with the polymer material during formation of the article, forming a film from the block copolymer which then is melt-pressed or adhered to the surface of the polymer material, and coating the surface of the polymer material with powdered block copolymer.

Polymer compositions having a low coefficient of friction are described by U.S. Pat. No. Re. 32,514 to D. J. Steklenski. The compositions comprise a blend of at least 80 percent by weight of a polymer and at least 0.35 percent by weight of a crosslinked silicone polycarbinol. The polymer preferably is a blend of cellulose nitrate and a hydrophobic acrylate polymer. The silicone polycarbinol in general is a hydroxy-terminated polysiloxane or hydroxy-substituted polysiloxane. The compositions typically are prepared by dissolving the polymer or polymer blend, silicone polycarbinol, and crosslinking agent in a suitable solvent and casting a film from which the solvent is allowed to evaporate.

Canadian Patent No. 1,049,682 describes the inclusion in a thermoplastic polymer of from 0.1 to 10 percent by weight of a carboxy-functional polysiloxane. Suitable thermoplastic polymers include polyolefins. Such inclusion is stated to enhance the properties or characteristics of the themoplastic polymer in one or more ways. By way of illustration, products or articles made from the polymer mixture were stated to have self-lubricating properties and increased resistance to wear. For molded articles, less friction during transfer, injection or extrusion molding was observed, and better release of parts from the molds was obtained. See, also, German Published Patent Application (Offenlegungschrift) No. 2,506,667 [*Chem. Abstr.,* 84:91066z (1976)].

Other, similar references which may be of interest include R. H. Somani and M. T. Shaw, *Macromolecules,* 14, 886 (1981), which describes the miscibility of polydimethylsiloxane in polystyrene; and S. N. Pandit et al., *Polym. Compos.,* 2, 68 (1981), which reports the use of a vinyltriethoxysilane polymer as a coupling agent in glass fiber-reinforced polypropylene.

It also may be noted that polysiloxanes have been utilized in the production of nonwoven webs or fabrics, or products made therefrom, as illustrated by the references which follow.

U.S. Pat. No. 3,360,421 to S. Sands describes a bonded nonwoven backing material having perforate selvage which is used in the manufacture of carpet. In the production of the nonwoven backing material, a nonwoven web is produced from a polyolefin such as polyethylene or polypropylene. The resulting web then is subjected to bonding conditions, followed by applying to the web a lubricant which can be, among other things, methyl hydrogen polysiloxane and dimethyl polysiloxane.

A finish composition for application to a continuous filament polypropylene sheet is disclosed in U.S. Pat. No. 3,766,115 to S. Sands. The composition comprises a mixture of two polysiloxane components, the first of which is a dyeable component comprising a primary or secondary aminoalkyl- or aminoalkoxyalkylpolysiloxane fluid having an amine functionality in the range of 4-7 percent and being substantially free of other reactive groups. The second component is a lubricant component comprising a polydialkyl/arylsiloxane fluid having hydroxy end groups and being substantially free of other reactive groups. The polypropylene sheet typically is a spunbonded sheet made from isotactic polypropylene.

U.S. Pat. No. 3,867,188 to P. E. Campbell and J. G. Kokoszka relates to a spunbonded nonwoven fabric which is especially useful as a carpet backing. The fabric has on it a silicone-glycol copolymer having the general formula:

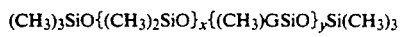

in which G is a radical of the structure —R(C$_3$H$_6$)$_z$OH, R is an alkylene radical containing from 1 to 18 carbon atoms, x has an average value of from 40-90, y has an average value of from 1-10, and z has an average value of from 1-10.

U.S. Pat. No. 3,929,509 to H. T. Taskier describes a hydrophilic microporous film which is useful as a battery separator. The film comprises a hydrophobic microporous film coated with a silicone glycol copolymer surfactant, preferably at a level of from 2 to 20 percent by weight, based on the uncoated film. In preferred embodiments, the surfactant coating comprises a mixture of a silicone glycol copolymer surfactant and a second surfactant which preferably is an imidazoline tertiary amine The silicone glycol copolymer surfactant preferably is a polyoxyethylene polymethylsiloxane.

A yarn finish formulation is disclosed in U.S. Pat. No. 4,105,569 to R. J. Crossfield. In preferred embodiments, the formulation contains a hydrocarbon-soluble, long molecular chain polymeric viscosity improver, such as polyisobutylene, and a polysiloxane. Preferably, the polysiloxane is an alkoxylated polysiloxane, such as a dimethylpolysiloxane with substituted polyethylene glycol or polypropylene glycol side chains or mixed polyethylene/polypropylene glycol side chains.

U.S. Pat. No. 4,563,190 to R. Töpfl describes a siloxane/oxyalkylene copolymer as an optional component of a dyeing assistant for dyeing or printing polyamide fiber material with anionic dyes. See also U.S. Pat. Nos. 4,444,563 to H. Abel and 4,426,203 to H. Abel and J. Oxe.

U.S. Pat. No. 4,645,691 to I. Ona and M. Ozaki describes a method for treating materials with organopolysiloxane compounds. The method involves applying to the material a composition containing a silicone compound which has one or more alkoxysilylalkyl groups and one or more polyoxyalkylene groups. The materials to be treated preferably are fibers and fiber-containing materials.

For a limited review of similar applications of silicones, see A. J. Sabia and R. B. Metzler, *Nonwovens Ind.*, 14, 16 (1983). Also note British Patent No. 1,273,445 [*Chem. Abstr.*, 76: 89559z (1972)], which describes the use of a block polysiloxane, among other materials, in the preparation of a leather substitute.

It may be noted that the above review briefly discusses polysiloxanes which have been modified by inclusion of a poly(oxyalkylene) moiety; such modified polysiloxanes can be employed in the composition of the present invention as an additive.

A modified polysiloxane in which the poly(oxyalkylene) moiety is a poly(oxypropylene) is described in U.S. Pat. No. 3,867,188 to P. E. Campbell and J. G. Kokoszka. The modified polysiloxane apparently is employed as a lubricant which coats a spunbonded nonwoven fabric. The fabric, in turn, is employed as a carpet backing. The addition of the modified polysiloxane to the backing is stated to reduce damage to the backing which results from the tufting process used to manufacture the carpet.

Additionally, polysiloxanes have been used in the manufacture of films. For example, U.S. Pat. No. 4,652,489 describes a sealable, opaque polyolefinic multilayer film. The film is composed of a polypropylene base layer, a nonsealable surface layer, and a sealable surface layer. The nonsealable layer is a combination of a propylene homopolymer and a slip agent which preferably is a polydiorganosiloxane. The polydiorganosiloxane is used in an amount of from about 0.3 to about 2.5 percent by weight and preferably comprises a polymethylphenylsiloxane or a polydimethylsiloxane.

Finally, several references are known which are or may be of interest in relation to the additive when it contains a disubstituted siloxane. Such references are described below.

Siloxane-oxyalkylene block copolymers are disclosed in U.S. Pat. No. 3,629,308 to D. L. Bailey and A. S. Pater. The copolymers are stated to be particularly useful as a foam stablizer in the production of polyurethane resin foams. The copolymers are represented by the formula:

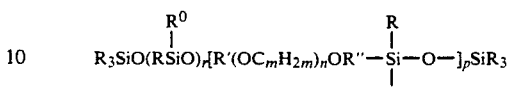

in which R is a monovalent hydrocarbon group, $R^0$ is hydrogen or a monovalent hydrocarbon group, $R'$ is hydrogen or a monovalent hydrocarbon group, $R''$ is a divalent hydrocarbon group, r has a value of at least 0, m is an integer that has a value of at least 2, n is a number that has a value of at least 1 (preferably at least 4), p is a number that has a value of at least 1, there are not more than three hydrogen atoms represented by $R^0$ in the copolymer (preferably less than one or none), and at least 25 weight-percent of the groups represented by $(OC_mH_{2m})$ are oxyethylene groups.

U.S. Pat. No. 4,150,013 to J. O. Punderson describes melt-processible tetrafluoroethylene copolymers containing organopolysiloxanes which are useful as wire insulation coatings. The organopolysiloxane is present in an amount of between about 0.2 and 5 percent by weight, based on the weight of the resulting copolymer composition. Representative organopolysiloxanes include polyphenylmethylsiloxane, polydimethylsiloxane, polymethylsiloxane, a copolymer of phenylmethylsiloxane and dimethylsiloxane, and the like.

A high viscosity silicone blending process is disclosed in U.S. Pat. No. 4,446,090 to E. M. Lovgren et al. The blends produced by the process are stated to have engineering properties and flame retardance superior to known blends. The process involves (a) melting a solid thermoplastic composition comprising one or more thermoplastic polymers within an extruder, (b) injecting a high viscosity silicone fluid into the molten thermoplastic composition within the extruder, and (c) blending said molten thermoplastic composition with said high viscosity silicone fluid within the extruder. The thermoplastic compositions include polyethylene and polypropylene. The silicone fluid typically is a polydimethylsiloxane. The blend can contain such additives as reinforcing fillers, antioxidants, lubricants, flame retardants, and the like. The additives can be introduced by means of the thermoplastic polymers, the silicone fluid, or both. Typical flame retardants include magnesium stearate, calcium stearate, barium stearate, antimony oxide, and decabromodiphenyloxide.

Siloxane-containing polymers are described in U.S. Pat. Nos. 4,480,009 and 4,499,149 to A. Berger. The properties of polymeric compositions are stated to be improved by the presence of a polysiloxane unit having a defined formula. The listing of polymers, however, does not include polyolefins. The disclosed compositions apparently are useful as protective coatings and as molding, extruding, laminating, and calendaring compositions. Solutions of the compositions can be used to prepare films and fibers.

U.S. Pat. No. 4,500,659 to L. A. Kroupa and E. H. Relyea relates to extrudable, curable polyorganosiloxane compositions. The compositions are similar to those of U.S. Pat. No. 4,585,830, described below. In the present case, the compositions comprise (A) a liquid triorganosiloxy end-blocked polydimethylsiloxane wherein the triorganosiloxy units are dimethylvinylsiloxy or methylphenylvinylsiloxy; (B) a reinforcing silica filler which has been reacted with a liquid or solubilized treating agent, at least one component of which is a liquid hydroxy end-blocked polyorganosiloxane wherein at least 50 percent of the silicon atoms are bonded to a fluorine-substituted hydrocarbon radical; (C) a liquid methylhydrogensiloxane having an average of at least three silicon-bonded hydrogen atoms per molecule; and (D) a platinum-containing catalyst. The bonded treating agent for the silica filler would be incompatible, i.e., insoluble, with the polydimethylsiloxane component if it were not bonded to the silica.

Olefin polymer compositions containing silicone additives are described in U.S. Pat. No. 4,535,113 to G. N. Foster and R. B. Metzler. The compositions apparently can be extruded through relatively narrow die gaps at commercial extrusion rates to provide films having improved optical and mechanical properties. The silicone additives have the formula,

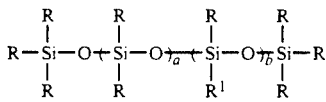

in which each R, which can be the same or different, is an alkyl radical preferably having from one to six carbon atoms, $R^1$ is a monovalent organic radical containing at least one ethyleneoxide group, vicinal epoxy group, or amino group, and a and b, which can be the same or different, each has a value of at least 1 and generally has a value of from about 4 to about 5,000. The silicone additives typically are present in the compositions in an amount of from about 0.01 to about 5 percent by weight.

U.S. Pat. No. 4,585,830 to R. P. Sweet describes polyorganosiloxane compositions useful for preparing unsupported extruded profiles. Such compositions are stated to include a triorganosiloxy end-blocked polydiorganosiloxane containing at least two vinyl radicals per molecule, in which at least 50 percent of the silicon-bonded organic radicals are methyl; and an organohydrogensiloxane containing at least two silicon-bonded hydrogen atoms per molecule, in which said hydrogen atoms are bonded to different silicon atoms. Examples of such two types of compounds are dimethylvinylsiloxy end-blocked polydimethylsiloxanes and trimethylsiloxy end-blocked dimethylsiloxane/methylhydrogensiloxane copolymers, respectively.

From the foregoing, it is evident that surfactants have been added to polymers to impart a hydrophilic character to the surface of the shaped article made from the polymer. These efforts appear to fall into either of two categories. In the first category, the surfactant is compatible with the polymer at ambient conditions, in which case the shaped article must be bloomed or heated after formation thereof to bring the surfactant to the surface. However, the surfactant is incompatible at melt-extrusion temperatures. In the second, the surfactant diffuses spontaneously to and remains on the surface of the shaped article because it is incompatible with the polymer at any temperature. Such incompatibility at melt-extrusion temperatures prevents or severely limits the use of such surfactants in the formation of melt-extruded fibers because the surfactant interferes with the continuous formation of fibers. Thus, in spite of the effort carried out to date, there is a pronounced need for a means of modifying the surface characteristics of fibers and films prepared from a thermoplastic polymer which avoids the disadvantages of known methods.

SUMMARY OF THE INVENTION

It therefore is an object of the present invention to provide a surface-segregatable, melt-extrudable thermoplastic composition.

It further is an object of the present invention to provide a surface-segregatable, melt-extrudable thermoplastic composition which comprises at least one thermoplastic polymer and at least one defined additive.

It also is an object of the present invention to provide a surface-segregatable, melt-extrudable thermoplastic composition comprising at least one thermoplastic polymer and at least one defined additive, which additive surface segregates in a controllable manner upon melt processing the composition to form a fiber or film with a well-defined interfacial surface, effective surface, subsurface, and core concentration gradient of the additive which imparts to the fiber or film at least one desired characteristic which otherwise would not be present.

A further object of the present invention is to provide a surface-segregatable, melt-extrudable thermoplastic composition which comprises at least one polymer and at least one defined additive which preferably contains at least one tetrasubstituted disiloxanylene group.

Yet another object of the present invention is to provide a fiber or film made from a surface-segregatable, melt-extrudable thermoplastic composition comprising at least one polymer and at least one defined additive, which fiber or film has at least one surface characteristic different from the surface characteristics of the polymer component of said composition.

These and other objects will be apparent to those having ordinary skill in the art from a consideration of the specification and claims which follow.

Accordingly, the present invention provides a surface-segregatable, melt-extrudable thermoplastic composition which comprises at least one thermoplastic polymer and at least one additive having at least two moieties, A and B, in which:

(A) moiety A and moiety B act as a single molecular unit which is compatible with said polymer at melt extrusion temperatures but is incompatible at temperatures below melt extrusion temperatures, but each of moiety A and moiety B, taken as separate molecular units, is incompatible with said polymer at melt extrusion temperatures and at temperatures below melt extrusion temperatures;

(B) moiety B has at least one functional group which imparts to said additive at least one desired characteristic;

(C) the molecular weight of said additive is in the range of from about 400 to about 15,000; and (D) the weight ratio of said polymer to said additive is in the range of from about 1 to about 1,000;

with the proviso that said additive cannot be a compound having the general formula,

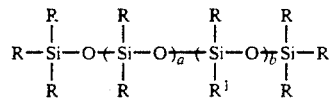

in which each R independently is a monovalent organic group selected from the group consisting of alkyl groups; $R^1$ is a monovalent organic group containing at least one ethyleneoxy group, vicinal epoxy group, or amino group; and a and b, which can be the same or different, each have a value of at least 1.

In preferred embodiments, the additive is a siloxane-containing compound.

In other preferred embodiments, moiety A comprises at least one tetrasubstituted disiloxanylene group, optionally associated with one or more groups selected from the group consisting of trisubstituted silyl and trisubstituted siloxy groups, the substituents of all such groups being independently selected from the group consisting of monovalent alkyl, cycloalkyl, aryl, and heterocyclic groups, each of which may be substituted or unsubstituted, and moiety B.

In still other preferred embodiments, the additive contains a plurality of groups selected from the group represented by the following general formulae:

$$B_1-, \tag{1}$$

$$B_2-O-, \tag{2}$$

$$R_1-, \tag{3}$$

$$R_2-Si\equiv, \tag{4}$$

$$(R_3)(R_4)(R_5)Si-, \tag{5}$$

$$(R_6)(R_7)(R_8)Si-O-, \tag{6}$$

$$[-Si(R_9)(R_{10})-O-]_c, \tag{7 and}$$

$$[-Si(R_{11})(B_3)-O-]_3; \tag{8}$$

in which each of $R_1$ and $R_2$ independently is a monovalent group selected from the group consisting of hydrogen, alkyl, cycloalkyl, aryl, and heterocyclic groups, each of which, except for hydrogen, may be substituted or unsubstituted; each of $R_3-R_5$, inclusive, independently is a monovalent group selected from the group consisting of alkyl, cycloalkyl, aryl, and heterocyclic groups, each of which may be substituted or unsubstituted, and $B_4$; each of $R_6-R_{11}$, inclusive, independently is a monovalent group selected from the group consisting of alkyl, cycloalkyl, aryl, and heterocyclic groups, each of which may be substituted or unsubstituted; each of c and d independently represents an integer from 0 to about 100 which indicates only the quantity of the respective group present in the additive without indicating or requiring, in instances when an integer is greater than 1, that such plurality of the respective group are connected to one another to form an oligomer or polymer or that all of such groups have identical substituents; and each of $B_1-B_4$, inclusive, independently is a moiety which imparts to the additive at least one desired characteristic; with the proviso that such plurality of groups results in at least one tetrasubstituted disiloxanylene group.

In other preferred embodiments, the additive is a compound having the general formula,

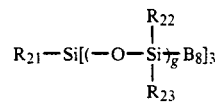

in which each of $R_{12}$ and $R_{13}$ independently is a monovalent group selected from the group consisting of hydrogen, alkyl, cycloalkyl, aryl, and heterocyclic groups, each of which, except for hydrogen, may be substituted or unsubstituted; each of $B_5$ and $B_6$ independently is a monovalent group having a desired characteristic; and e represents an integer from 2 to about 100.

In still other preferred embodiments, the additive is a compound having the general formula,

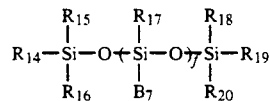

in which each of $R_{14}-R_{20}$, inclusive, independently is a monovalent group selected from the group consisting of hydrogen, alkyl, cycloalkyl, aryl, and heterocyclic groups, each of which, except for hydrogen, may be substituted or unsubstituted; $B_7$ is a monovalent group having a desired characteristic; and f represents an integer from 1 to about 100.

In yet other preferred embodiments, the additive is a compound having the general formula,

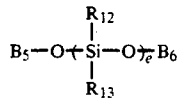

in which each of $R_{21}-R_{23}$, inclusive, independently is a monovalent group selected from the group consisting of hydrogen, alkyl, cycloalkyl, aryl, and heterocyclic groups, each of which, except for hydrogen, may be substituted or unsubstituted; $B_8$ is a monovalent group having a desired characteristic; and g represents an integer from 1 to about 100.

The surface-segregatable, melt-extrudable composition of the present invention is adapted to processing by melt extrusion to form a fiber or film having a differential, increasing concentration of the additive from the center to the surface thereof, such that the concentration of additive in at least one of the interfacial surface, effective surface, and subsurface of the fiber or film is greater than the average concentration of additive in the core of the fiber or film and imparts to the surface of the fiber or film at least one desired characteristic which otherwise would not be present. The additive is miscible with said polymer at melt extrusion temperatures, under which conditions the additive and the polymer form a metastable solution. As the temperature of the newly formed fiber or film drops below melt extrusion temperatures, the additive becomes significantly less compatible with the polymer. Concurrent with this marked change in compatibility, the polymer begins to solidify. Both factors contribute to the rapid migration or segregation of the additive which takes place in a controllable manner.

The present invention also provides a method for preparing a fiber or film having a differential, increasing concentration of an additive from the center to the surface thereof, such that the concentration of additive in at least one of the interfacial surface, effective surface, and subsurface of the fiber or film is greater than the average concentration of additive in the core of the fiber or film, thereby imparting to the surface of the fiber or film at least one desired characteristic which otherwise would not be present, which method comprises melting a mixture of at least one thermoplastic polymer and at least one additive having at least two moieties, A and B, and extruding the resulting melt through a die at a shear rate of from about 50 to about 30,000 sec$^{-1}$ and a throughput of from about 0.01 to about 5.4 kg/cm/hour, in which:

(A) moiety A and moiety B act as a single molecular unit which is compatible with said polymer at melt extrusion temperatures but is incompatible at temperatures below melt extrusion temperatures, but each of moiety A and moiety B, taken as separate molecular units, is incompatible with said polymer at melt extrusion temperatures and at temperatures below melt extrusion temperatures;

(B) moiety B has at least one functional group which imparts to said additive at least one desired characteristic;

(C) said additive is miscible with said polymer at melt extrusion temperatures, under which conditions said additive and said polymer form a metastable solution, but as the temperature drops below melt extrusion temperatures, said additive becomes significantly less compatible with said polymer and, concurrently, the polymer begins to solidify, with both events contributing to the rapid, controlled surface segregation of said additive;

(D) the molecular weight of said additive is in the range of from about 400 to about 15,000; and (E) the weight ratio of said polymer to said additive is in the range of from about 6 to about 350;

with the proviso that said additive cannot be a compound having the general formula,

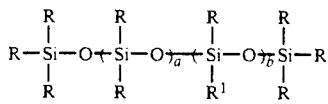

in which each R independently is a monovalent organic group selected from the group consisting of alkyl groups; R$^1$ is a monovalent organic group containing at least one ethyleneoxy group, vicinal epoxy group, or amino group; and a and b, which can be the same or different, each have a value of at least 1.

The present invention further provides a fiber or film which is made from a thermoplastic composition of the present invention, and a nonwoven web comprising fibers made from a thermoplastic composition of the present invention. The present invention also provides a disposable absorbent product, at least one component of which is a nonwoven web comprising fibers made from a thermoplastic composition of the present invention.

In certain preferred embodiments, the polymer component of the thermoplastic composition of the present invention is a polyolefin, such as polyethylene and polypropylene. In other preferred embodiments, the polymer is a polyester, such as poly(ethylene terephthalate).

The surface-segregatable, melt-extrudable thermoplastic composition of the present invention is useful in the preparation of fibers and films which have at least one surface characteristic which is different from the surface characteristics of the polymer component of the thermoplastic composition. Such thermoplastic composition is particularly useful in the formation of nonwoven webs which are employed in the construction of such disposable absorbent products as diapers, feminine care products, incontinence products, and the like.

DETAILED DESCRIPTION OF THE INVENTION

A full appreciation of the uniqueness of the present invention requires an understanding of the definitions of various terms used throughout the specification and claims. The definitions, in turn, will be more fully understood by reference to FIG. 1.

Figure 1:
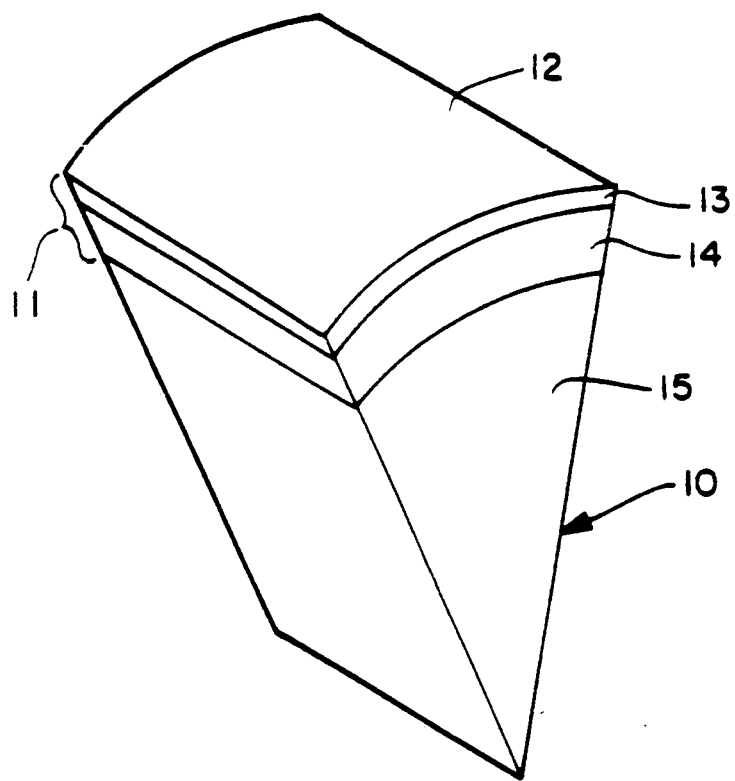
FIG. 1 is a diagrammatic representation of a wedge of fiber to illustrate certain definitions used throughout the specification and claims.

FIG. 1 is a diagrammatic representation of a wedge of a fiber prepared in accordance with the present invention. Fiber 10 can be considered to consist of two major portions, surface 11 and core 15. The latter includes all of the fiber which is not included in surface 11. Surface 11 has three components: interfacial surface 12, effective surface 13, and subsurface 14. The interfacial surface in essence is the monomolecular layer of the fiber which is at the air/polymer (or nonfiber/fiber) interface. The effective surface begins at the interfacial surface and extends into the fiber a distance of about 15 Å. The subsurface lies below the effective surface and extends into the fiber to a depth of about 1,000 Å; thus, the subsurface has a thickness of about 985 Å. Although not illustrated by a drawing, these definitions also apply to films prepared from a composition of the present invention.

In order for the surface of a fiber or film to exhibit the desired characteristic which is not exemplified by the polymer in the absence of the additive, it is not necessary for the additive, and moiety B in particular, to be present at the interfacial surface. Rather, such desired characteristic will be observed if the additive, and moiety B in particular, is within about 15 Å of the interfacial surface because of the conformational changes in the additive which occur spontaneously at ambient conditions. Below about 15 Å, however, these conformational changes usually are not sufficient to make the additive effectively available at the interfacial surface.

Nevertheless, the presence of additive in the subsurface region is important because additive in that region often can be "coaxed" to move into the effective surface region by the application of gentle heat. Moreover, there are some characteristics which do not require the additive to be at either the interfacial surface or effective surface for the additive to be effective with respect thereto. By way of illustration only, examples of such characteristics include ultraviolet radiation stability and degradation inhibition.

In this regard, the term "gentle heat" generally means temperatures in the range of from about 45° to about 110° Celsius for periods of only a few seconds up to about a minute or so. Usually, additive present in the core region can be moved to the effective surface only under conditions which are closer to the prior art blooming procedure discussed earlier.

It should be noted that the term "bulk" is used herein differently from the term "core". As already pointed out, the latter term refers to that portion or region of the fiber or film which is below the subsurface layer or region. The term "bulk", on the other hand, has reference to the entire fiber or film and usually is employed in reference to elemental analyses of fiber or film samples.

As already stated, the surface-segregatable, melt-extrudable thermoplastic composition of the present invention comprises at least one thermoplastic polymer and at least one additive.

The term "melt-extrudable" is equivalent to "melt-processable" and is not intended to be limited in any way. That is, the term is intended to encompass the use of the composition in any melt-extrusion process which is or may be employed to prepare fibers or films, provided the process meets the limitations imposed by the claims. Thus, the term includes the use of the composition in melt-spinning of continuous filaments; meltblowing, spun-bonding, and coforming of nonwoven webs; the casting and blowing of films; and the like.

As a matter of convenience, the present invention is described in detail primarily as applied to the formation of fibers and nonwoven webs. Such description, however, is by way of illustration only and is not intended to in any way limit either the spirit or scope of the present invention.

In general, the term "thermoplastic polymer" is used herein to mean any thermoplastic polymer which can be used for the preparation of fibers or films. Examples of thermoplastic polymers include, by way of illustration only, end-capped polyacetals, such as poly(oxymethylene) or polyformaldehyde, poly(trichloroacetaldehyde), poly(n-valeraldehyde), poly(acetaldehyde), poly(propionaldehyde), and the like; acrylic polymers, such as polyacrylamide, poly(acrylic acid), poly(methacrylic acid), poly(ethyl acrylate), poly(methyl methacrylate), and the like; fluorocarbon polymers, such as poly(tetrafluoroethylene), perfluorinated ethylene-propylene copolymers, ethylene-tetrafluoroethylene copolymers, poly(chlorotrifluoroethylene), ethylene-chlorotrifluoroethylene copolymers, poly(vinylidene fluoride), poly(vinyl fluoride), and the like; polyamides, such as poly(6-aminocaproic acid) or poly($\epsilon$-caprolactam), poly(hexamethylene adipamide), poly(hexamethylene sebacamide), poly(11-aminoundecanoic acid), and the like; polyaramides, such as poly(imino-1,3-phenyleneiminoisophthaloyl) or poly(m-phenylene isophthalamide), and the like; parylenes, such as poly-p-xylylene, poly(chloro-p-xylylene), and the like; polyaryl ethers, such as poly(oxy-2,6-dimethyl-1,4-phenylene) or poly(p-phenylene oxide), and the like; polyaryl sulfones, such as poly(oxy-1,4-phenylenesulfonyl-1,4-phenyleneoxy-1,4-phenylene-isopropylidene-1,4-phenylene), poly(sulfonyl-1,4-phenyleneoxy-1,4-phenylenesulfonyl-4,4'-biphenylene), and the like; polycarbonates, such as poly(bisphenol A) or poly(carbonyldioxy- 1,4-phenyleneisopropylidene-1,4-phenylene), and the like; polyesters, such as poly(ethylene terephthalate), poly(tetramethylene terephthalate), poly(cyclohexylene-1,4dimethylene terephthalate) or poly(oxymethylene-1,4-cyclohexylenemethyleneoxyterephthaloyl), and the like; polyaryl sulfides, such as poly(p-phenylene sulfide) or poly(thio-1,4-phenylene), and the like; polyimides, such as poly(pyromellitimido-1,4-phenylene), and the like; polyolefins, such as polyethylene, polypropylene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, polyacrylonitrile, poly(vinyl acetate), poly(vinylidene chloride), polystyrene, and the like; copolymers of the foregoing, such as acrylonitrile-butadiene-styrene (ABS) copolymers, and the like; and the like.

The preferred polymers are polyolefins and polyesters, with polyolefins being more preferred. Even more preferred are those polyolefins which contain only hydrogen and carbon atoms and which are prepared by the addition polymerization of one or more unsaturated monomers. Examples of such polyolefins include, among others, polyethylene, polypropylene, poly(1- butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polystyrene, and the like. In addition, such term is meant to include blends of two or more polyolefins and random and block copolymers prepared from two or more different unsaturated monomers. Because of their commercial importance, the most preferred polyolefins are polyethylene and polypropylene.

Broadly stated, the additive must have at least two moieties, A and B, in which:

(A) moiety A and moiety B act as a single molecular unit which is compatible with said polymer at melt extrusion temperatures but is incompatible at temperatures below melt extrusion temperatures, but each of moiety A and moiety B, taken as separate molecular units, is incompatible with said polymer at melt extrusion temperatures and at temperatures below melt extrusion temperatures; and (B) moiety B has at least one functional group which imparts to said polymeric material at least one desired characteristic.

Because the additive is compatible with the polymer at melt extrusion temperatures, the additive is miscible with the polymer and the polymer and the additive form a metastable solution. The solution formed by the additive and the polymer at temperatures above melt extrusion temperatures is referred to herein as a metastable solution since the solution is not stable at temperatures below melt extrusion temperatures. As the temperature of the newly formed fiber or film drops below melt extrusion temperatures, the polymer begins to solidify which contributes to additive separating from the polymer phase. At the same time, the additive becomes less compatible with the polymer. Both factors contribute to the rapid migration or segregation of additive toward the surface of the newly formed fiber or film which occurs in a controllable manner.

This preferential, rapid migration or segregation is controllable because the extent or degree of migration is, at least in part, a function of the molecular weight of the additive, the shear rate, and the throughput. While the mechanism of additive migration or segregation is not fully understood, it appears that the rate of migration or segregation is:

(1) indirectly proportional to the additive molecular weight—the higher the additive molecular weight, the slower the rate of segregation;

(2) directly proportional to the shear rate—the higher the shear rate, the faster the rate of segregation; and (3) indirectly proportional to throughput—the higher the throughput, the slower the rate of segregation.

There are at least three very surprising and unexpected aspects to the present invention. The first is that the additive as defined herein is compatible with the polymer at melt extrusion temperatures, given the fact that moieties A and B, when taken as separate molecular units, are incompatible with the polymer at any temperature. The second is that lower molecular weight additives perform better than higher molecular weight additives; this is contrary to the conventional wisdom of polymer additives which favors higher molecular weights. The third and perhaps most startling aspect is the rapidity with which the segregation of the additive takes place.

As just noted, the effect of additive molecular weight on the rate of segregation was surprising, especially in view of past experiences with polydimethylsiloxane. Upon reflection, it now appears that the movement of lower molecular weight additives through the gradually solidifying polymer is roughly analogous to the movement of small particles through a viscous fluid—the larger the particles, the greater the resistance to movement through the fluid. This analogy seem appropriate since it has been demonstrated that the additive exists as small globules in the polymer, which globules become smaller as the temperature of the molten composition increases. By imposing shear forces on the molten composition, the globules are broken down into smaller globules far more quickly than would have occurred in the absence of shear. Thus, shear is a contributing factor which enhances the segregation of the additive to the surface of the newly formed filament.

In general, the shear rate will be in the range of from about 50 to about 30,000 $sec^{-1}$. Preferably, the shear rate will be in the range of from about 150 to about 5,000 $sec^{-1}$, and most preferably from about 300 to about 2,000 $sec^{-1}$.

It perhaps should be mentioned at this point that the compatibility requirement is critical. That is, if the additive is not compatible with the polymer at melt-extrusion temperatures, the composition cannot be melt processed to give satisfactory fibers or films.

By way of clarification, it already has been noted that compounds such as polydimethylsiloxane have been incorporated in polymers which were extruded, but not melt processed to give fibers or films. Such compounds migrated to the surface of the extruded article to provide a lubricated surface to aid further processing or removal from a mold. Because extrusion times were very slow compared to the melt processing times typically experienced in fiber and film formation, migration or segregation rates were not an issue. However, the incompatibility of the added compounds prevents acceptable melt-processing because of discontinuities in fiber formation and holes and other related defects in films. In addition, such compounds often reduce friction within the extruder to the point that the molten mixture rotates essentially as a plug with no downstream movement taking place.

Finally, throughput is of importance because it affects the time the newly formed fiber or film is in a sufficiently molten or fluid state to allow migration or segregation of the additive to the newly formed surfaces, even though throughput also affects the shear rate. Stated differently, it is possible to control the rate of migration or segregation by controlling the rate of cooling of the newly formed fiber or film. Thus, for any given molecular weight additive, the extent of migration can be reduced by rapidly cooling the fiber or film. Alternatively, migration can be enhanced by reducing the rate of cooling.

Throughput typically will be in the range of from about 0.01 to about 5.4 kg/cm/hour. Preferably, throughput will be in the range from about 0.1 to about 4.0 kg/cm.hour. The throughput most preferably will be in the range of from about 0.5 to about 2.5 kg/cm/hour.

As used herein, the phrase "molten state" does not necessarily mean "flowable". Rather, the term is used to denote a condition of the thermoplastic composition in which the additive molecules still are capable of migrating or segregating to the surface of the newly formed fiber or film. Thus, the term is somewhat imprecise and not readily subject to accurate measurement. Consequently, this composition fluidity factor preferentially is described or accounted for by the term "throughput".

The controlled migration or segregation of additive toward the surface of the fiber or film results in a controllable differential concentration of additive in the fiber or film. If measurable migration is allowed to occur, the concentration of the additive in the fiber or film will increase with increasing distance from the center thereof. By the proper selection of additive, additive molecular weight, shear rate, and throughput (or rate of cooling), a substantial amount, or perhaps even all, of the additive can be found in the surface. Because the concentration of additive in the core of the fiber or film typically will vary nonlinearly from the concentration of the additive in the surface, this concentration difference is referred to herein as a differential concentration.

While the additive can be either a liquid or a solid, a liquid is preferred. It also is preferred that a liquid additive have a surface tension which is less than that of virgin polymer; the lower surface tension assures that the additive will be more likely to completely "wet" or cover the surface of the fiber or film as the segregation process proceeds to completion, especially under conditions favoring a large concentration differential.

As already noted, additive surface segregation is influenced by the molecular weight of the additive. More specifically, the lower the molecular weight of the additive, the more rapid is the rate of segregation of the additive to the surface of the fiber or film at any given temperature at which the fiber or film still is in a sufficiently molten state.

It should be apparent that the additive can be monomeric, oligomeric, or polymeric. Indeed, polymeric additives are required in order to achieve the higher additive molecular weights permitted by the present invention. Because lower additive molecular weights are preferred, the preferred additives perhaps are properly referred to as oligomers. However, such nomenclature can be misleading and reliance instead should be placed on the molecular weight of the additive and the other parameters already described. It is for this reason that the additive is not referred to as a polymeric additive, even though in many instances the additive will be oligomeric or polymeric in nature.

As already stated, the additive molecular weight will be in the range of from about 400 to about 15,000. This range encompasses suitable additive molecular weights, regardless of whether the additive is to be used to prepare a fiber or a film. As a practical matter, however, the suitable additive molecular weight range for fibers is not as broad as that for films because fiber formation generally takes place much more quickly than does film formation. Moreover, the additive molecular weight range also depends in part on whether or not an additive will be used by itself or in a mixture of additives.

Accordingly, the molecular weight range for additives which are to be used individually in compositions for fiber formation and not as part of a mixture of additives typically is from about 400 to about 3,000. Preferably, this range is from about 500 to about 2,000, and more preferably from about 500 to about 1,500. The most preferred range is from about 500 to about 1,000.

When additives are intended to be used in a mixture intended for incorporation in fiber-forming compositions, however, higher molecular weights can be employed. Although the reasons for this are not clearly understood, mixtures of additives frequently are more compatible with the polymer at melt-extrusion temperatures than are the individual additives. Although the selection of additive mixtures is somewhat empirical, in general such mixtures can utilize additives having molecular weights in the range of from about 400 to about 10,000 and preferably from about 400 to about 8,000. Fortunately, the hot stage microscope studies described in the Examples can be used as a simple screening method to estimate whether or not a given mixture can be used successfully.

In this regard, some clarification of the term "used successfully" is necessary. The successful use of an additive or a mixture of additives has reference to two factors. First, the additive or additive mixture must segregate to the target zone in order to achieve the intended properties. For example, if water-wettable fibers are desired, the additive or additive mixture must segregate to either or both of the interfacial surface and the effective surface of the fibers, unless a mild post-formation heat treatment is going to be included in the process. Second, the composition containing the additive or additive mixture must process well enough in commercial-scale equipment to give a web or fabric, or a film, having the required aesthetic and physical properties.

When an additive is to be used for the preparation of a film, the additive molecular weight typically will be in the range of from about 400 to about 15,000. This range preferably will be from about 500 to about 8,000, and most preferably from about 500 to about 4,000. As with additives intended for fiber formation, film-formation compositions also may use additive mixtures, in which case the upper limit of the specified molecular weight ranges can be somewhat higher.

It should be noted that the foregoing molecular weight ranges are based on the assumption that oligomeric or polymeric additives will have relatively broad polydispersities, e.g., of the order of about 1.2. While narrow polydispersities certainly are achievable, usually at a higher cost, they are not necessary in the practice of the present invention, even if relatively low molecular weight additives are to be employed. As a guideline, it may be noted that for a given additive, the average molecular weight of an additive having a narrower polydispersity usually should be slightly lower than the average molecular weight of an additive having a broad polydispersity. While this guideline is not precise and is somewhat empirical in nature, one skilled in the art will be able to properly select an additive of any polydispersity without undue experimentation.

The term "additive" is used broadly herein to encompass the use of two or more additives in a given composition. Such two or more additives may have the same or similar moieties B, or different moieties B having the same characteristic, e.g., water wettability. On the other hand, two or more additives may be used which have different characteristics, which characteristics may be related or unrelated. Such two or more additives may be present in similar or significantly different amounts. Moreover, the additives may have the same or similar molecular weights in order to segregate in the fiber or film to approximately the same region. Alternatively, different molecular weight additives may be employed in order to effectively layer the additives in the surface.

The use of different molecular weight additives is especially attractive for some characteristics which reinforce each other, an example of which is the use of a first additive having a moiety B which is an absorber of ultraviolet radiation and a second additive having a light stabilizing or degradation inhibiting moiety B which functions by deactivating excited oxygen molecules or terminating free radicals. The first additive normally will have a lower molecular weight than the second. While both additives segregate to the surface, the first additive migrates primarily to the effective surface, while the second additive migrates primarily to the subsurface. Thus, actinic radiation which is not absorbed by the first additive is effectively nullified by the second additive. The result is a complimentary or even synergistic effect which is greater than that which would be achieved if the two additives were comingled in the same region.

The additive preferably is a material which will be referred to herein loosely as a siloxane. When the additive is a siloxane, moiety A will comprise at least one tetrasubstituted disiloxanylene group, optionally associated with one or more groups selected from the group consisting of trisubstituted silyl and trisubstituted siloxy groups, the substituents of all such groups being independently selected from the group consisting of monovalent alkyl, cycloalkyl, aryl, and heterocyclic groups, each of which may be substituted or unsubstituted. As a practical matter, moiety A often will consist of all three groups. Moreover, more than one tetrasubstituted disiloxanylene group often will be present, particularly when the additive has an appreciable molecular weight.

As used herein, the term "tetrasubstituted disiloxanylene group" means a group having the following general formula:

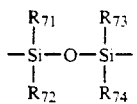

in which each of $R_{71}$-$R_{74}$, inclusive, is a monovalent group independently selected from the group consisting of alkyl, cycloalkyl, aryl, and heterocyclic groups.

As noted, the substituents of the groups comprising moiety A can be alkyl, cycloalkyl, aryl, or heterocyclic groups which may be the same or different and which in turn may be substituted or unsubstituted. Other than the obvious requirement that such substituents not adversely affect additive stability or other properties, there are no known limitations to such substituents. However, for reasons relating primarily to commercial availability and ease of synthesis, such substituents preferably are alkyl groups and more preferably are unsubstituted alkyl groups having from 1 to 3 carbon atoms. Most preferably, such substituents are methyl groups.

More specifically, the additive preferably contains a plurality of groups selected from the group represented by the following general formulae, it being understood that not all groups need to be present and that the presence of some groups precludes the presence of others:

$B_1-$,  (1)

$B_2-O-$,  (2)

$R_1-$,  (3)

$R_2-Si\equiv$,  (4)

$(R_3)(R_4)(R_5)Si-$,  (5)

$(R_6)(R_7)(R_8)Si-O-$,  (6)

$[-Si(R_9)(R_{10})-O-]_c$,  (7) and $[-Si(R_{11})(B_3)-O-]_d$.  (8)

in which each of $R_1$ and $R_2$ independently is a monovalent group selected from the group consisting of hydrogen, alkyl, cycloalkyl, aryl, and heterocyclic groups, each of which, except for hydrogen, may be substituted or unsubstituted; each of $R_3$-$R_5$, inclusive, independently is a monovalent group selected from the group consisting of alkyl, cycloalkyl, aryl, and heterocyclic groups, each of which may be substituted or unsubstituted, and $B_4$; each of $R_6$-$R_{11}$, inclusive, independently is a monovalent group selected from the group consisting of alkyl, cycloalkyl, aryl, and heterocyclic groups, each of which may be substituted or unsubstituted; each of c and d independently represents an integer from 0 to about 100 which indicates only the quantity of the respective group present in the additive without indicating or requiring, in instances when an integer is greater than that such plurality of the respective group are connected to one another to form an oligomer or polymer or that all of such groups have identical substituents; and each of $B_1$-$B_4$, inclusive, independently is a moiety which imparts to the additive at least one desired characteristic; with the proviso that such plurality of groups results in at least one tetrasubstituted disiloxanylene group.

Molecular weight limitations, if desired, are readily achieved by limiting the sum of c and d to the extent required to achieve the desired molecular weight.

In general, the preparation of the siloxane moiety is well known to those having ordinary skill in the art. Siloxanes that have reactive groups, such as H—Si≡, RO—Si≡, and Cl—Si≡, are used as starting products. Such materials are prepared either by hydrolysis of, e.g., methylchlorosilanes or by copolymerization of cyclic or linear polymethylsiloxanes with functional siloxanes. See, for example, W. Noll, "Chemistry and Technology of Silicones," Academic Press, New York, 1968; and R. Meals, "Encyclopedia of Chemical Technology," Vol. 18, 2nd Edition, 1969, p.221.

Turning now to moiety B, it is this moiety which must have at least one functional group which imparts to the additive at least one desired characteristic. Because the additive migrates or segregates toward the surface of the filament upon its formation, it is the presence of moiety B in the surface of the filament which results in such surface acquiring the at least one characteristic of moiety B. Such at least one characteristic clearly would not be found in the surface of the filament in the absence of the additive. Examples of such characteristics include, by way of illustration only and without limitation, wettability by water or other polar solvents, preferential wettability by alcohols, enhanced hydrophobicity which contributes to a nonstaining surface, and stability to actinic radiation, especially ultraviolet radiation.

It perhaps should be noted at this point that the term "functional group" refers to that portion of moiety B which imparts the desired at least one characteristic; the term is not to be equated to "reactive", although a group which also is reactive is not precluded by the term "functional group".

Moiety B need not be limited to a single desired characteristic. Alternatively, the additive can contain two or more moieties B which have different characteristics.

For example, a moiety B may have a wettable group and a group which is stable to actinic radiation or a group which absorbs ultraviolet radiation and a group which inhibits actinic radiation-induced degradation, or one moiety B may have a wettable group while a second moiety B is stable to actinic radiation.

The point of attachment of moiety B to moiety A is not known to be critical. For example, when moiety A is a siloxane, moiety B can be a substituent of any one or more of the tetrasubstituted disiloxanylene, trisubstituted silyl, and trisubstituted siloxy groups which may be present.

Those having ordinary skill in the art, upon determining the characteristic or characteristics desired for any given additive, will know what functional group or groups may be required for moiety B. In other words, the selection of functional groups is well within the abilities and understanding of one having ordinary skill in the art in view of the teaching herein. In order to illustrate the principles involved, though, several preferred embodiments will be described in detail.

To obtain a fiber or film having a surface which is water wettable and moiety A of the additive is a siloxane, moiety B preferably is a poly(oxyalkylene) moiety. More preferably, the alkylene portion of such moiety will contain from 2 to about 6 carbon atoms Most preferably, moiety B is a poly(oxyalkylene) moiety in which the oxyalkylene repeating units are oxyethylene or oxypropylene or a mixture thereof.

References which disclose polysiloxanes containing one or more poly(oxyalkylene) moieties suitable for use as the additive include, among others, U.S. Pat. Nos. 2,836,748, 2,917,480, 2,991,300, 2,991,301, 3,168,543, 3,172,899, 3,236,252, 3,278,485, 3,280,160, 3,299,113, 3,356,758, 3,402,192, 3,480,583, 3,505,377, 3,509,192, 3,530,159, 3,600,418, and Re. 27,541; Belgian Patent No. 627,281; British Patent Nos. 892,819, 954,041, 963,437, 981,811, 981,812, 1,073,368, and 1,098,646; French Patent Nos. 1,259,241, 1,356,962, 1,411,757, 1,413,125, 1,482,133, 1,511,661, 1,520,444, and 1,179,743; German published Specification (Offenlegungsschrift) Nos. 1,495,927, 1,570,656, 1,595,730, 2,045,360, and 2,555,053; German Patent Nos. 1,235,594, 1,257,433, 1,301,576, 1,570,647, and 1,195,953.

By way of illustration only, three types of additives for imparting water wettability to the surfaces of filaments, referred to hereinafter as types A, B, and C, respectively, are described below with reference to the plurality of preferred groups described earlier. In each case, moiety B is an oxyalkylene-containing moiety which is represented by the following general formula:

$$-(CH_2)_x-O-(C_2H_4O)_y(C_3H_6O)_z-R_{24},$$

in which $R_{24}$ is a monovalent group selected from the group consisting of hydrogen and lower alkyl; x represents an integer from 0 to about 3; and each of y and z independently represents an integer from 0 to about 100 which indicates only the quantity of the respective group present in the additive without indicating or requiring, in instances when an integer is greater than 1, that such plurality of the respective group are connected to one another to form an oligomer or polymer.

Type A Additives

The first type, which is most preferred, consists of groups of formulae 1, 2, and 7, in which each of $R_9$ and $R_{10}$ independently is an alkyl group containing from 1 to 3 carbon atoms; $R_{24}$ is an alkyl group containing from 1 to 4 carbon atoms; a is in the range of from 3 to about 60; x is 0; y is in the range of from about 5 to about 25; and z is in the range of from about 0 to about 25.

Specific examples of type A additives, by way of illustration only, include materials having the following general formula:

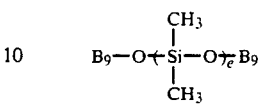

in which $B_9$ is $-(C_2H_4O)_y(C_3H_6O)_z-R_{24}$, where e, y, z, and $R_{24}$ are as already defined.

Commercially available additives of this type include TEGOPREN BC-1781, in which e has an average value of 5.5, $R_{24}$ is n-butyl, and the ethylene oxide/propylene oxide weight percent ratio in $B_9$ is 40/60; TEGOPREN D-985, in which e has an average value of 4.3, $R_{24}$ is methyl, and the ethylene oxide/propylene oxide weight percent ratio in $B_9$ is 70/30; and TEGOPREN V-337, in which e has an average value of 4, $R_{24}$ is methyl, and the ethylene oxide/propylene oxide weight percent ratio in $B_9$ is 100/0.

Type A additives in general are prepared by heating silicon with, e.g., chloromethane in the presence of a copper catalyst at about 300° C. to give dichlorodimethyl silane (see, e.g., U.S. Pat. No. 2,380,995 to E. G. Rochow) which, when reacted with water, gives a polymer having the following general formula:

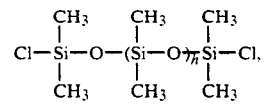

where h is an integer representing the number of repeating units in the molecule. See, for example, B. B. Hardman and A. Torkelson, "Encyclopedia of Chemical Technology," 3rd Edition, John Wiley & Sons, Inc., New York, 1982, pp. 922-962. The polymer then is reacted in the presence of trifluoroacetic acid with an oxyalkylene-containing compound having the general formula, $$HO-(C_2H_4O)_y(C_3H_6O)_z-R_{24}$$

in which $R_{24}$, y, and z are as already defined, to give the additive. See U.S. Pat. No. 2,836,748 to D. L. Bailey and F. M. O'Connor. See also U.S. Pat. No. 2,917,480, U.S. Pat. No. 3,505,377 to E. L. Morehouse, and German Patent No. 1,259,241.

Type B Additives

The second type of additives consists of groups of formulae 5-8, inclusive, in which each of $R_3-R_{11}$, inclusive, independently is an alkyl group containing from 1 to 3 carbon atoms; $R_{24}$ is an alkyl group containing from 1 to 4 carbon atoms; c is in the range of from about 3 to about 30; d is in the range of from about 1 to about 10; x is 3; y is in the range of from about 5 to about 25; and z is in the range of from about 0 to about 25.

Specific examples of type B additives, also by way of illustration only, include materials having the following general formula:

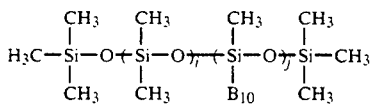

in which $B_{10}$ is $-(CH_3)_3-O-(C_2H_4O)_y(C_3H_6O)_zR_{24}$, where $R_{24}$, y, and z are as already defined, i represents an integer from 0 to about 100, and j represents an integer from 1 to about 100.

Commercially available examples of this type include SILWET L-77, SILWET L-7500, and SILWET L-7602 (Union Carbide Corporation, Danbury, Conn.). Other commercially available examples include TEGOPREN 5843, in which the i/j value is 13/5, $R_{24}$ is hydrogen, and the ethylene oxide/propylene oxide weight percent ratio in $B_{10}$ is 100/0; TEGOPRENr 5847, in which the i/j value is 0/1, $R_{24}$ is hydrogen, and the ethylene oxide/propylene oxide weight percent ratio in $B_{10}$ is 80/20; TEGOPREN 5852, in which the i/j value is 20/5, $R_{24}$ is hydrogen, and the ethylene oxide/propylene oxide weight percent ratio in $B_{10}$ is 20/80; TEGOPREN 5863, in which $R_{24}$ is hydrogen and the ethylene oxide/propylene oxide weight percent ratio in $B_{10}$ is 40/60; TEGOPREN 5873, in which the i/j value is 20/5, $R_{24}$ is hydrogen, and the ethylene oxide/propylene oxide weight percent ratio in $B_{10}$ is 35/65; and TEGOPREN 5878, in which $R_{24}$ is hydrogen and the ethylene oxide/propylene oxide weight percent ratio in $B_{10}$ is 100/0 (Th. Goldschmidt AG, Essen, Federal Republic of Germany).

The synthesis of the type B additives begins with a reactive silicon fluid, prepared by known methods, such as that represented by the following formula:

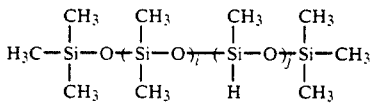

in which i and j are as already defined. The fluid is reacted with a compound having the general formula,

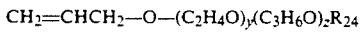

$CH_2=CHCH_2-O-(C_2H_4O)_y(C_3H_6O)_zR_{24}$ in which $R_{24}$, y, and z are as already defined, to give the additive. The reaction is carried out in the presence of a platinum/τ-aluminum oxide catalyst at a temperature of the order of 150° C. See, e.g., U.S. Pat. No. 3,280,160 to D. L. Bailey, U.S. Pat. No. 3,172,899, also to D. L. Bailey, and U.S. Pat. No.3,505,377 to E. L. Morehouse. The compound which is reacted with the silicone fluid is obtained by the condensation of ethylene oxide and propylene oxide with allyl alcohol in the presence of a catalytic amount of potassium hydroxide, a well-known reaction.

Type C Additives

The third, and last, type of additives consists of groups of formulae 2, 4, and 7, in which each of $R_2$, $R_9$, and $R_{10}$ independently is an alkyl group containing from 1 to 3 carbon atoms; $R_{24}$ is an alkyl group containing from 1 to 4 carbon atoms; c is in the range of from 0 to about 50; x is 0; y is in the range of from about 5 to about 25; and z is in the range of from about 0 to about 25.

Specific examples of type C additives, again by way of illustration only, include materials having the following general formula:

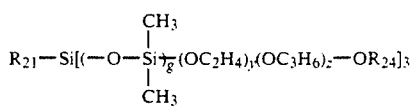

in which $R_{21}$ and $R_{24}$ are lower alkyl groups, g is as already defined, and each of y and z represents an integer from 0 to about 70.

A specific commercially available example is SILWET L-720 (Union Carbide Corporation, Danbury, Conn.).

Type C additives are prepared by the method described in U.S. Pat. No. 2,836,748 to D. L. Bailey and F. M. O'Connor. Briefly, methyltriethoxysilane and mixed cyclic polydimethylsiloxanes are heated at about 150° C. in the presence of potassium hydroxide as catalyst to give a material having the following general formula:

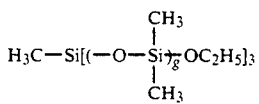

in which g is as already defined. This material then is reacted in the presence of trifluoroacetic acid with an oxyalkylene-containing compound having the general formula,

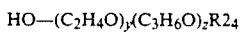

$HO-(C_2H_4O)_y(C_3H_6O)_zR_{24}$ where y, z, and $R_{24}$ are as already defined, to give the additive.

When the desired characteristic of the additive is ultraviolet light absorption, moiety B is a chromophore, especially a chromophore having a sufficiently high efficiency for the absorption of ultraviolet radiation. Preferably, moiety B is a benzotriazolyl group, more preferably a 2-(substituted-phenyl)benzotriazolyl group. A class of most preferred additives for the absorption of ultraviolet light is described and claimed in copending and commonly assigned application Ser. No. 07/181,624 cross-referenced earlier.

The most preferred additives which absorb ultraviolet radiation can be represented by the general formula, S—Z, in which S represents a siloxane moiety and Z represents a benzotriazolyl group having the following general formula:

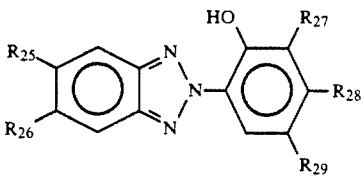

in which
(1) $R_{25}$ is either a monovalent group selected from the group consisting of hydrogen and chloro or a divalent connecting group;
(2) $R_{26}$ is either a monovalent group selected from the group consisting of hydrogen, chloro, carboxy, sulfo, ethylsulfonyl, $C_1$-$C_8$ alkyl, $C_1$-$C_4$ alkoxy, vinylbenzyloxy, and alkoxycarbonyl in which the alkoxy moiety contains from 2 to 9 carbon atoms, or a divalent connecting group;

(3) $R_{27}$ is a monovalent group selected from the group consisting of hydrogen, chloro, carboxyethyl, $C_1$-$C_{14}$ alkyl, $C_1$-$C_4$ alkoxy, cyclopentyl, cyclohexyl, phenyl, phenyl substituted with $C_1$-$C_8$ alkyl groups, $C_7$-$C_9$ phenylalkyl, and alkoxycarbonyl in which the alkoxy moiety contains from 2 to 9 carbon atoms;

(4) $R_{28}$ is a monovalent group selected from the group consisting of hydrogen, chloro, hydroxy, $C_1$-$C_4$ alkyl, $C_1$-$C_8$ alkoxy, and vinylbenzyloxy; and (5) $R_{29}$ is a monovalent group selected from the group consisting of hydrogen, chloro, $C_1$-$C_{14}$ alkyl, cyclopentyl, cyclohexyl, and $C_7$-$C_9$ phenylalkyl.

Preferably, $R_{25}$ is hydrogen or a divalent connecting group; $R_{26}$ is hydrogen, chloro, methyl, ethyl, methoxy, carboxy, or a divalent connecting group; $R_{27}$ is hydrogen, chloro, methyl, sec-butyl, t-butyl, t-pentyl, t-octyl, α-methylbenzyl, or α,α-dimethylbenzyl; $R_{28}$ is hydrogen; and $R_{29}$ is $C_1$-$C_8$ alkyl, cyclohexyl, phenyl, chloro, α-methylbenzyl, or carboxyethyl. $R_{25}$ most preferably will be hydrogen and $R_{26}$ will be a divalent connecting group.

Compounds coming within the foregoing general formula for the benzotriazolyl component, less the divalent connecting group(s), are known, as are procedures for preparing such compounds. See, by way of illustration, U.S. Pat. Nos. 3,004,896, 3,055,896, 3,072,585, 3,074,910, 3,189,615, 3,230,194, 3,253,921, 3,983,132, 4,041,044, 4,096,242, 4,127,586, 4,129,521, 4,226,763, 4,283,327, 4,278,590, 4,383,863, 4,414,393, and 4,447,511, each of which is incorporated herein by reference.

In general, such compounds can be prepared by various methods, such as (1) by coupling a phenyldiazonium compound with a phenyl azo compound, followed by oxidation of the resulting o-aminoazo compound; or (2) by coupling an o-nitrophenyldiazonium compound with a phenol, followed by reduction with, e.g., ammonium sulfide or zinc in an alkaline medium.

A benzotriazole is coupled to a siloxane by known means. For example, a reactive siloxane, such as one of those described earlier, can be converted to another siloxane having a different reactive group. As an illustration, the H—Si≡ group can be reacted with allyl glycidyl ether, in which case the new reactive group is an epoxide. The new reactive group then can be coupled to the benzotriazole by known means. Alternatively, the reactive siloxane can be combined directly with a benzotriazole having at least one functional group which is reactive with the siloxane.

Moiety B is a degradation inhibitor when the desired characteristic of the additive is light stabilization. Preferably, such inhibitor contains a piperidyl group. Most preferably, such inhibitor contains a polyalkyl-substituted piperidyl group. A most preferred class of additives for imparting to the fiber or film stabilization to light consists of those compounds disclosed and claimed in copending and commonly assigned application Ser. No. 07/181,623, also cross-referenced earlier.

Such preferred class of light-stabilizing additives can be represented by the general formula, S'—Z', in which S' represents a siloxane moiety and Z' represents a pendant tetraalkylpiperidyl group attached by means of a divalent connecting group to a silicon atom and having the following general formula:

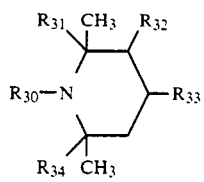

in which (1) $R_{30}$ is either (a) a monovalent group selected from the group consisting of hydrogen; hydroxy; $C_1$-$C_{18}$ alkyl; $C_2$-$C_4$ hydroxyalkyl; $C_8$-$C_{12}$ phenylhydroxyalkyl; $C_3$-$C_8$ alkenyl; $C_7$-$C_{12}$ phenylalkyl; $C_1$-$C_8$ alkanoyl; $C_3$-$C_5$ alkenoyl; and —CON($R_{35}$)—($R_{36}$), in which each of $R_{35}$ and $R_{36}$ is a monovalent group independently selected from the group consisting of hydrogen, $C_1$-$C_{18}$ alkyl, $C_3$-$C_{12}$ alkoxyalkyl, $C_2$-$C_8$ hydroxyalkyl, $C_3$-$C_{12}$ alkenyl, $C_7$-$C_{14}$ phenylalkyl, $C_6$-$C_{14}$ aryl, $C_7$-$C_{14}$ alkaryl, $C_3$-$C_7$ cycloalkyl, and 2,2,6,6,-tetramethyl-4-piperidyl; or (b) a divalent connecting group;

(2) $R_{31}$ is $C_1$-$C_5$ alkyl;

(3) $R_{32}$ is hydrogen or $C_1$-$C_5$ alkyl;

(4) $R_{33}$ is either (a) a monovalent group selected from the group consisting of hydrogen; hydroxy; $C_1$-$C_{12}$ alkoxy; $C_3$-$C_{14}$ alkoxyalkoxy (oxaalkoxy); $C_3$-$C_5$ alkenoxy; poly(oxyethylene) having from 1 to 10 oxyethylene repeating units; carboxy; $C_1$-$C_{18}$ alkoxycarbony; $C_3$-$C_5$ alkenoxycarbonyl; $C_3$-$C_8$ cycloalkoxycarbonyl; $C_6$-$C_{10}$ aryloxycarbonyl; $C_7$-$C_{12}$ alkylaryloxycarbonyl; $C_7$-$C_{12}$ phenylalkoxycarbonyl; carboxymethyl; $C_1$-$C_{18}$ alkoxycarbonylmethyl; $C_3$-$C_5$ alkenoxycarbonylmethyl; $C_5$-$C_8$ cycloalkoxycarbonyl; $C_6$-$C_{10}$ aryloxycarbonylmethyl; $C_7$-$C_{12}$ alkylaryloxycarbonyl; $C_7$-$C_{12}$ phenylalkoxycarbonylmethyl; $C_2$-$C_{20}$ alkanoyloxy (alkoxycarbonyloxy); cyano; cyanomethyl; 2-cyanoethoxy;

—N($R_{37}$)($R_{38}$), in which each of $R_{37}$ and $R_{38}$ independently is a monovalent group selected from the group consisting of $C_1$-$C_{18}$ alkyl, $C_2$-$C_{14}$ alkoxyalkyl, $C_3$-$C_5$ alkenyl, $C_5$-$C_8$ cycloalkyl, $C_7$-$C_{12}$ phenylalkyl, $C_6$-$C_{10}$ aryl, $C_2$-$C_5$ hydroxyalkyl, and $C_7$-$C_{10}$ cycloalkylalkyl;

—$CH_2CH_2$N($R_{37}$)($R_{38}$), in which $R_{37}$ and $R_{38}$ are as already defined;

—CO—N($R_{39}$)($R_{40}$), in which each of $R_{39}$ and $R_{40}$ independently is hydrogen, a group as defined for $R_{35}$ and $R_{36}$, or a monovalent group selected from the group consisting of $C_3$-$C_{12}$ alkoxyalkyl, $C_3$-$C_{12}$ alkenyl, $C_2$-$C_8$ hydroxyalkyl, $C_7$-$C_{14}$ phenylalkyl, $C_6$-$C_{14}$ aryl, and $C_7$-$C_{14}$ alkaryl;

—N($R_{41}$)—CO—$R_{42}$, in which $R_{41}$ is hydrogen or a group as defined for $R_{37}$ and $R_{38}$ and $R_{42}$ is a monovalent group selected from the group consisting of $C_1$-$C_{12}$ alkyl, $C_3$-$C_{14}$ alkoxyalky, $C_2$-$C_{14}$ alkyl which is substituted with carboxy or the $C_1$-$C_4$ alkyl ester thereof, $C_2$-$C_5$ alkenyl, $C_5$-$C_8$ cycloalkyl, $C_7$-$C_{12}$ phenylalkyl, $C_6$-$C_{10}$ aryl, and $C_7$-$C_{12}$ alkylaryl;

—O—CO—$R_{43}$, in which $R_{43}$ is a monovalent group selected from the group consisting of $C_1$-$C_{18}$ alkyl, $C_3$-$C_{14}$ alkoxyalkyl, $C_2$-$C_{14}$ alkyl which is substituted by carboxy or the $C_1$-$C_4$ alkyl ester thereof, $C_2$-$C_5$ alkenyl, $C_5$-$C_8$ cycloalkyl, $C_7$-$C_{12}$ phenylalkyl, $C_6$-$C_{10}$ aryl, $C_7$-$C_{12}$ alkylaryl, and phenyl or $C_7$-$C_{10}$ phenylalkyl which is substituted by hydroxy and 1-3 $C_1$-$C_4$ alkyl groups;

—N($R_{41}$)—CO—O—$R_{44}$, in which $R_{41}$ is as already defined and $R_{44}$ is a monovalent group selected from the group consisting of $C_1$-$C_{12}$ alkyl, $C_3$-$C_5$ alkenyl, $C_5$-$C_8$ cycloalkyl, phenyl, and $C_7$-$C_{12}$ phenylalkyl;

—O—CO—O—$R_{44}$, in which $R_{44}$ is as already defined; and

—O—CO—N($R_{45}$)($R_{46}$), in which each of $R_{45}$ and $R_{46}$ independently is hydrogen or a group as defined for $R_{37}$ and $R_{38}$;

or (b) a divalent connecting group; and (5) $R_{34}$ is $C_1$-$C_5$ alkyl.

Preferably, $R_{30}$ is hydrogen, $C_1$-$C_{12}$ alkyl, allyl, benzyl, acetyl, acryloyl, or a divalent connecting group; each of $R_{31}$ and $R_{34}$ is methyl; and $R_{32}$ is hydrogen.

Compounds coming within the foregoing general formula for the tetraalkylpiperidyl component, less the divalent connecting group(s), also are known, as are procedures for preparing such compounds. See, by way of illustration, U.S. Pat. Nos. U.S. Pat. Nos. 4,278,590, 4,299,926, 4,348,524, 4,472,547, 4,511,596, 4,569,997, 4,590,268, Re. 31,342, and Re. 31,343, each of which is incorporated herein by reference. See also, H. S. Mosher, "Piperidines and Partially Hydrogenated Pyridines," Chapter 9 in A. R. Katritzky and C. Rees, Editors, "Heterocyclic Compounds," Pergammon Press, Illinois, 1984, pp. 617-676.

Briefly, piperidines can be prepared by the reduction of pyridine compounds or by ring closure reactions at a nitrogen atom or between carbon atoms. Ring closure reactions at a nitrogen atom can be 1,5-dihalides, 1,5-aminohalides, 1,5-amino alcohols, 4,5-unsaturated amines, 1,5-diamines, or δ-aminocarbonyl compounds, or from the reduction of 1,3-dinitriles, 1,3-cyano esters, or 1,4-aminonitriles. Ring closure reactions between carbon atoms typically involve the Dieckmann condensation of suitable dicarboxylic esters or nitriles in which the ring closure is completed between the carbon atoms in the β,τ positions. Alternatively, ring closure be accomplished from several fragments by means of the Petrenko-Kritschenko reaction. Modifications of the piperidines then can be accomplished by a variety of methods, such as those described in the patent literature cited above.

The tetraalkylpiperidines can be coupled to siloxanes by known procedures, as already described.

If a moiety B is desired which has the capability of both absorbing ultraviolet radiation and inhibiting degradation, the additive preferably will one of those described and claimed in application Ser. No. 07/181,463, noted earlier. Such additives can be represented by the general formula, S"—Z", in which S" represents a siloxane moiety and Z" represents a pendant benzotriazolyl/tetraalkylpiperidyl group attached by means of a divalent connecting group to a silicon atom, in which:

(A) the benzotriazolyl moiety is represented by the general formula,

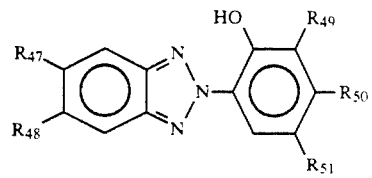

in which
(1) $R_{47}$ is (a) a monovalent group selected from the group consisting of hydrogen and chloro; (b) a tetraalkylpiperidyl group; or (c) a divalent connecting group;

(2) $R_{48}$ is (a) a monovalent group selected from the group consisting of hydrogen, chloro, carboxy, sulfo, ethylsulfonyl, $C_1$-$C_8$ alkyl, $C_1$-$C_4$ alkoxy, vinylbenzyloxy, and alkoxycarbonyl in which the alkoxy moiety contains from 2 to 9 carbon atoms; (b) a tetraalkylpiperidyl group; or (c) a divalent connecting group;

(3) $R_{49}$ is (a) a monovalent group selected from the group consisting of hydrogen, chloro, carboxyethyl, $C_1$-$C_{14}$ alkyl, $C_1$-$C_4$ alkoxy, cyclopentyl, cyclohexyl, phenyl, phenyl substituted with $C_1$-$C_8$ alkyl groups, $C_7$-$C_9$ phenylalkyl, and alkoxycarbonyl in which the alkoxy moiety contains from 2 to 9 carbon atoms; (b) a tetraalkylpiperidyl group; or (c) a divalent connecting group;

(4) $R_{50}$ is a monovalent group selected from the group consisting of hydrogen, chloro, hydroxy, $C_1$-$C_4$ alkyl, $C_1$-$C_8$ alkoxy, and vinylbenzyloxy; and (5) $R_{51}$ is (a) a monovalent group selected from the group consisting of hydrogen, chloro, $C_1$-$C_{14}$ alkyl, cyclopentyl, cyclohexyl, and $C_7$-$C_9$ phenylalkyl, alkyl; (b) a tetraalkylpiperidyl group; or (c) a divalent connecting group; and (B) the tetraalkylpiperidyl moiety is represented by the general formula,

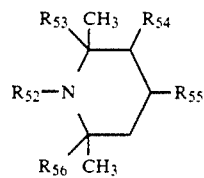

in which
(1) $R_{52}$ is (a) a monovalent group selected from the group consisting of hydrogen; hydroxy; $C_1$-$C_{18}$ alkyl; $C_2$-$C_4$ hydroxyalkyl; $C_8$-$C_{12}$ phenylhydroxyalkyl; $C_3$-$C_8$ alkenyl; $C_7$-$C_{12}$ phenylalkyl; $C_1$-$C_8$ alkanoyl; $C_3$-$C_5$ alkenoyl; and —CO—N($R_{57}$)($R_{58}$), in which each of $R_{57}$ and $R_{58}$ is a monovalent group independently selected from the group consisting of hydrogen, $C_1$-$C_{18}$ alkyl, $C_3$-$C_{12}$ alkoxyalkyl, $C_2$-$C_8$ hydroxyalkyl, $C_3$-$C_{12}$ alkenyl, $C_7$-$C_{14}$ phenylalkyl, $C_6$-$C_{14}$ aryl, $C_7$-$C_{14}$ alkaryl, $C_3$-$C_7$ cycloalkyl, and 2,2,6,6-tetramethyl-4-piperidyl; (b) a benzotriazolyl group; or (c) a divalent connecting group;

(2) $R_{53}$ is $C_1$-$C_5$ alkyl;

(3) $R_{54}$ is hydrogen or $C_1$-$C_5$ alkyl;

(4) $R_{55}$ is (a) a monovalent group selected from the group consisting of hydrogen; hydroxy; $C_1$-$C_{12}$ alkoxy; $C_3$-$C_{14}$ alkoxyalkoxy (oxaalkoxy); $C_3$-$C_5$ alkenoxy; poly(oxyethylene) having from 1 to 10 oxyethylene repeating units; carboxy; $C_1$-$C_{18}$ alkoxycarbony; $C_3$–$C_5$ alkenoxycarbonyl; $C_3$–$C_8$ cycloalkoxycarbonyl; $C_6$–$C_{10}$ aryloxycarbonyl; $C_7$–$C_{12}$ alkylaryloxycarbonyl; $C_7$–$C_{12}$ phenylalkoxycarbonyl; carboxymethyl; $C_1$–$C_{18}$ alkoxycarbonyl methyl; $C_3$–$C_5$ alkenoxycarbonylmethyl; $C_5$–$C_8$ cycloalkoxycarbonyl; $C_6$–$C_{10}$ aryloxycarbonylmethyl; $C_7$–$C_{12}$ alkylaryloxycarbonyl; $C_7$–$C_{12}$ phenylalkoxycarbonylmethyl; $C_2$–$C_{20}$ alkanoyloxy (alkoxycarbonyloxy); cyano; cyanomethyl; 2-cyanoethoxy;

—$N(R_{59})(R_{60})$, in which each of $R_{59}$ and $R_{60}$ independently is a monovalent group selected from the group consisting of $C_1$–$C_{18}$ alkyl, $C_2$–$C_{14}$ alkoxyalkyl, $C_3$–$C_5$ alkenyl, $C_5$–$C_8$ cycloalkyl, $C_7$–$C_{12}$ phenylalkyl, $C_6$–$C_{10}$ aryl, $C_2$–$C_5$ hydroxyalkyl, and $C_7$–$C_{10}$ cycloalkylalkyl;

—$CH_2CH_2N(R_{59})(R_{60})$, in which $R_{59}$ and $R_{60}$ are as already defined;

—$CO$—$N(R_{61})(R_{62})$, in which each of $R_{61}$ and $R_{62}$ independently is hydrogen, a group as defined for $R_{57}$ and $R_{58}$, or a monovalent group selected from the group consisting of $C_3$–$C_{12}$ alkoxyalkyl, $C_3$–$C_{12}$ alkenyl, $C_2$–$C_8$ hydroxyalkyl, $C_7$–$C_{14}$ phenylalkyl, $C_6$–$C_{14}$ aryl, and $C_7$–$C_{14}$ alkaryl;

—$N(R_{63})$—$CO$—$R_{64}$, in which $R_{63}$ is hydrogen or a group as defined for $R_{59}$ and $R_{60}$ and $R_{64}$ is a monovalent group selected from the group consisting of $C_1$–$C_{12}$ alkyl, $C_3$–$C_{14}$ alkoxyalky, $C_2$–$C_{14}$ alkyl which is substituted with carboxy or the $C_1$–$C_4$ alkyl ester thereof, $C_2$–$C_5$ alkenyl, $C_5$–$C_8$ cycloalkyl, $C_7$–$C_{12}$ phenylalkyl, $C_6$–$C_{10}$ aryl, and $C_7$–$C_{12}$ alkylaryl;

—$O$—$CO$—$R_{65}$, in which $R_{65}$ is a monovalent group selected from the group consisting of $C_1$–$C_{18}$ alkyl, $C_3$–$C_{14}$ alkoxyalkyl, $C_2$–$C_{14}$ alkyl which is substituted by carboxy or the $C_1$–$C_4$ alkyl ester thereof, $C_2$–$C_5$ alkenyl, $C_5$–$C_8$ cycloalkyl, $C_7$–$C_{12}$ phenylalkyl, $C_6$–$C_{10}$ aryl, $C_7$–$C_{12}$ alkylaryl, and phenyl or $C_7$–$C_{10}$ phenylalkyl which is substituted by hydroxy and 1-3 $C_1$–$C_4$ alkyl groups;

—$N(R_{63})$—$CO$—$O$—$R_{66}$, in which $R_{63}$ is as already defined and $R_{66}$ is a monovalent group selected from the group consisting of $C_1$–$C_{12}$ alkyl, $C_3$–$C_5$ alkenyl, $C_5$–$C_8$ cycloalkyl, phenyl, and $C_7$–$C_{12}$ phenylalkyl;

—$O$—$CO$—$O$—$R_{66}$, in which $R_{66}$ is as already defined; and

—$O$—$CO$—$N(R_{67})(R_{68})$, in which each of $R_{67}$ and $R_{68}$ independently is hydrogen or a group as defined for $R_{59}$ and $R_{60}$;

(b) a benzotriazolyl group; or (b) a divalent connecting group; and (5) $R_{56}$ is $C_1$–$C_5$ alkyl.

Preferably, $R_{47}$ is hydrogen, a tetraalkylpiperidyl group, or a divalent connecting group; $R_{48}$ is hydrogen, chloro, methyl, ethyl, methoxy, carboxy, a tetraalkylpiperidyl group, or a divalent connecting group; $R_{49}$ is hydrogen, chloro, methyl, sec-butyl, t-butyl, t-pentyl, t-octyl, α-methylbenzyl, or α,α-dimethylbenzyl; $R_{50}$ is hydrogen; $R_{51}$ is $C_1$–$C_8$ alkyl, cyclohexyl, phenyl, chloro, α-methylbenzyl, or carboxyethyl; $R_{52}$ is hydrogen, $C_1$–$C_{12}$ alkyl, allyl, benzyl, acetyl, acryloyl, a benzotriazolyl group, or a divalent connecting group; each of $R_{53}$ and $R_{56}$ is methyl; and $R_{54}$ is hydrogen.

The preparations of suitable benzotriazolyl and tetraalkylpiperidyl moieties already have been described, as have been methods of preparing siloxane moities. Compounds having benzotriazolyl and tetraalkylpiperidyl moieties are described in U.S. Pat. No. 4,481,315, which is incorporated herein by reference. Procedures for coupling siloxane moieties to organic groups also have been described earlier.

As used throughout this specification and the appended claims, the term "divalent connecting group" is employed broadly to mean, without limitation, any divalent group known to those having ordinary skill in the art for covalently coupling one organic moiety to another, or an organic moiety to a silicon atom, provided that such divalent group is sufficiently thermally stable at melt-extrusion temperatures.

As a practical matter, the divalent connecting group will involve alkylene, ether, or amine linkages, examples of which are listed below:

—$(CH_2)_n$—, where n is an integer representing the number of repeating methylene groups—when an organic moiety is being connected to a silicon atom, n will have a value of at least 3;

—$O$—;

—$O$—$R_{75}$—, in which $R_{75}$ represents a divalent organic group, e.g., $C_1$–$C_{14}$ alkylene, cycloalkylene, and arylene;

—$(CH_2)_n$—$O$—, where n is as already defined;

—$(CH_2)_n$—$O$—$R_{75}$—, where n and $R_{75}$ are as already defined;

—$NH$—;

—$N(R_{76})$—, in which $R_{76}$ represents a monovalent organic group, e.g., $C_1$–$C_{14}$ alkyl;

—$NH$—$R_{77}$—, in which $R_{77}$ represents a divalent organic group, e.g., $C_1$–$C_{14}$ alkylene, cycloalkylene, and arylene; and —$N(R_{78})$—$R_{79}$—, in which $R_{78}$ represents a monovalent organic group, e.g., $C_1$–$C_{14}$ alkyl, and $R_{79}$ represents a divalent organic group, e.g., $C_1$–$C_{14}$ alkylene, cycloalkylene, and arylene.

Of the above, methylene and ether linkages are preferred when two organic moieties are being linked together, with methylene linkages being most preferred because of the higher thermal stability which is associated with such linkages. In addition, a nitrogen atom normally will not be directly coupled to a silicon atom However, the above listing is representative only, and the selection of these and other coupling groups is well known to those having ordinary skill in the field of synthetic organic chemistry.

When a nonstaining or low surface energy fiber or film is desired, i.e., a fiber or film having a hydrophobicity which is higher than that of the virgin polymer component of the composition, moiety B conveniently can be a perfluorohydrocarbon group, any number of which are known to those having ordinary skill in the art. Also known to those having ordinary skill in the art are groups which can be use as moiety B in order to impart a buffering capacity to the fiber or film, such as a buffering capacity against hydrogen ions. In view of the teachings herein, other possible characteristics of moiety B will be readily apparent.

In general, the weight ratio of polymer to additive can vary from about 1 to about 1,000. That is, the amount of additive in the surface-segregatable, melt-extrudable thermoplastic composition of the present invention can range from about 50 percent by weight to about 0.1 percent by weight. Because the additive has a significant influence on the rheology of the melt, compositions containing greater amounts of polymeric material tend to be too fluid for melt-extrusion processes. On the other hand, lower amounts typically do not result in significant surface modification of the fiber or film. As a point of interest, it was observed that although melt viscosities are reduced by inclusion of the additive in the polymer, friction within the extruder does not appear to be significantly affected if the extruder screw design is compatible with the compositions. This result is consistent with the formation of a metastable solution. But, such result is contrary to experience with other silicon-containing compounds known to have been incorporated in polymers and, thus, unexpected.

In melt-extrusion processes such as those used to prepare fibers and nonwoven webs, the weight ratio of polymer to additive preferably will be in the range of from about 6 to about 350. More preferably, such ratio will vary from about 9 to about 200, and most preferably from about 20 to about 200.

The thermoplastic composition of the present invention can be prepared by any number of methods known to those having ordinary skill in the art. For example, the polymer in chip or pellet form and the additive can be mixed mechanically to coat the polymer particles with additive. If desired, the additive can be dissolved in a suitable solvent to aid the coating process, although the use of a solvent is not preferred. The coated polymer then can be added to the feed hopper of the extruder from which the fibers or film will emerge. Alternatively, the coated polymer can be charged to a heated compounder, such as a heated twin-screw compounder, in order to disperse the additive thoughout the bulk of the polymer. The resulting thermoplastic composition typically is extruded as rods which are fed to a chipper. The resulting chips then serve as the feed stock for a melt-processing extruder. In another method, the additive can be metered into the throat of the hopper which contains the polymer in particulate form and which feeds the extruder. In yet another method, the additive can be metered directly into the barrel of the extruder where it is blended with the molten polymer as the resulting mixture moves toward the die.

The method provided by the present invention is a method for preparing a fiber or film having a differential, increasing concentration of an additive from the center to the surface thereof, which differential, increasing concentration imparts to the surface of the fiber or film at least one desired characteristic which otherwise would not be present. The method comprises melting a mixture of at least one thermoplastic polymer and at least one additive having at least two moieties, A and B, and extruding the resulting melt through a die at a shear rate of from about 50 to about 30,000 sec$^{-1}$ and a throughput of from about 0.01 to about 5.4 kg/cm/hour, in which:

(A) moiety A and moiety B act as a single molecular unit which is compatible with said polymer at melt extrusion temperatures but is incompatible at temperatures below melt extrusion temperatures, but each of moiety A and moiety B, taken as separate molecular units, is incompatible with said polymer at melt extrusion temperatures and at temperatures below melt extrusion temperatures;

(B) moiety B has at least one functional group which imparts to said additive at least one desired characteristic;

(C) said additive is miscible with said polymer at melt extrusion temperatures, under which conditions said additive and said polymer form a metastable solution, but as the temperature drops below melt extrusion temperatures, said additive becomes significantly less compatible with said polymer and, concurrently, the polymer begins to solidify, with both events contributing to the rapid, controlled segregation of said additive;

(D) the molecular weight of said additive is in the range of from about 400 to about 15,000; and (E) the weight ratio of said thermoplastic polymer to said polymeric material is in the range of from about 6 to about 350;

with the proviso that said additive cannot be a compound having the general formula,

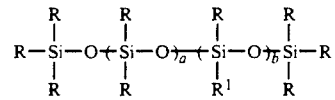

in which each R independently is a monovalent organic group selected from the group consisting of alkyl groups; $R^1$ is a monovalent organic group containing at least one ethyleneoxy group, vicinal epoxy group, or amino group; and a and b, which can be the same or different, each have a value of at least 1.

The key to the method, of course, is the use of the surface-segregatable, melt-extrudable thermoplastic composition of the present invention which has been discussed in detail already. Otherwise, anyone having ordinary skill in the art and having familiarity with various melt-extrusion processes will be able to produce fibers and films without undue experimentation, based on the teaching provided herein. For example, nonwoven webs may be formed by meltblowing in accordance with U.S. Pat. Nos. 3,016,599, 3,704,198, and 3,849,241; or by spunbonding in accordance with U.S. Pat. Nos. 3,361,394, 3,655,862, 3,705,068, 3,802,817, 3,853,651, 4,064,605, 4,405,297, and 4,434,204; or by coforming in accordance with U.S. Pat. No. 1,100,324.

The present invention is further described by the examples which follow. Such examples, however, are not to be construed as limiting in any way either the spirit or scope of the present invention, especially since the experimental work concentrated on (but is not limited to) imparting wettability to polyolefin fibers. In the examples, all temperatures are in degrees Celcius and all parts are by weight unless stated otherwise.

EXAMPLES

For convenience, the examples are divided into six sections describing (1) the additives and polymers employed; (2) the preparation of surface-segregatable, melt-extrudable thermoplastic compositions; (3) the preparation of melt-pressed films from the thermoplastic compositions; (4) the preparation of fibers from the thermoplastic compositions; (5) the preparation of cast films from the thermoplastic compositions; and (6) evaluation of a known material as an additive by way of comparison.

I. Descriptions of Additives and Polymers

A. Additives

Each of the additives employed in the examples was a type A, B, or C additive. The structures imparting water wettability are identified in Tables 1, 3, and 5 ("MW" represents molecular weight); if an additive were commercially available, the material designation or catalog number is given in the column labeled "I.D." and a manufacturer code is given in the column labeled "Source". The properties of the additives identified in Tables 1, 3, and 5 are summarized in Tables 2, 4, and 6, respectively. The structures of additives imparting characteristics other than water wettability are given in Table 7 and their properties are summarized in Table 8.

TABLE 1

Type A Additives Imparting Water Wettability $$R_{24}O-(C_2H_4O)_y(C_3H_6O)_z-Si(CH_3)_2-O]_e(C_3H_6O)_z(C_2H_4O)_yR_{24}$$

with $CH_3$ groups on Si

| Additive Code | $R_{24}$ | e | z | y | MW | I.D. | Source |
|---|---|---|---|---|---|---|---|
| A01 | $CH_3$ | 3 | 0 | 3 | 516 | V-363 | $G^a$ |
| A02 | $CH_3$ | 3 | 0 | 3 | 516 | V-360 | G |
| A03 | $CH_3$ | 4 | 0 | 3 | 590 | V-361 | G |
| A04 | $CH_3$ | 3 | 0 | 4 | 604 | V-336 | G |
| A05 | $CH_3$ | 4 | 0 | 4 | 678 | KC-V2$^b$ | G |
| A06 | $CH_3$ | 4 | 0 | 4 | 678 | V-337 | G |
| A07 | $CH_3$ | 3 | 1.5 | 3 | 690 | V-362 | G |
| A08 | $CH_3$ | 4 | 1 | 3 | 706 | V-3003 | G |
| A09 | $CH_3$ | 3 | 1.5 | 4 | 778 | V-338 | G |
| A10 | $CH_3$ | 4 | 1 | 4 | 794 | KC-V3$^b$ | G |
| A11 | $CH_3$ | 4 | 1.5 | 4 | 852 | T-3004 | G |
| A12 | $CH_3$ | 4 | 1.5 | 4 | 852 | V-339 | G |
| A13 | $CH_3$ | 4 | 1.5 | 4 | 852 | V-335 | G |
| A14 | $CH_3$ | 4 | 0 | 6 | 854 | KC-V4 | G |
| A15 | $CH_3$ | 4.3 | 1.5 | 5 | 1023 | D-985 | G |
| A16 | $CH_3$ | 5.7 | 1.5 | 5 | 1127 | D-984 | G |
| A17 | $CH_3$ | 4.3 | 1.5 | 7.5 | 1130 | D-979 | G |
| A18 | NA$^c$ | NA | 0 | NA | 1200 | PS-071 | UC$^d$ |
| A19 | $CH_3$ | 5.5 | 1.5 | 7.5 | 1200 | D-978 | G |
| A20 | n-$C_4H_9$ | 5.5 | NA | NA | 1450 | BC-1781 | G |
| A21 | NA | NA | NA | NA | 2400 | PS-555 | UC |
| A22 | $CH_3$ | 6 | NA | NA | NA | V-284 | G |
| A23 | NA | 6 | NA | NA | NA | V-290 | G |
| A24 | H | 60 | 17 | 16 | 7922 | T-5830 | G |

$^a$Th. Goldschmidt AG, Essen, Federal Republic of Germany.
$^b$Synthesis utilized a purer polyether.
$^c$Not available.
$^d$Union Carbide Corporation, Danbury, Connecticut.

TABLE 2

Properties of the Type A Additives of Table 1

| Code | Viscosity$^a$ | Cloud Point$^b$ | Surface Tension$^c$ |
|---|---|---|---|
| A01 | 7 | NA$^d$ | 24.9 |
| A02 | 10 | 1 | 24.4 |
| A03 | 11 | 1 | 22.5 |
| A04 | 16 | 7 | 24.2 |
| A05 | 13 | <0 | 23.5 |
| A06 | 15 | 2 | 23.4 |
| A07 | 18 | 7 | 26.0 |
| A08 | 15 | <0 | NA |
| A09 | 17 | 4 | 25.2 |
| A10 | 24 | <0 | 24.3 |
| A11 | 23 | <3 | 25.2 |
| A12 | 16 | 2 | 22.8 |
| A13 | 18 | 2 | 24.3 |
| A14 | 22 | 15 | 23.9 |
| A15 | 26 | 22 | NA |
| A16 | 31 | 21 | NA |
| A17 | 58 | 45 | 25.8 |
| A18 | 20 | 20 | NA |
| A19 | 59 | 40 | 24.0 |
| A20 | 40 | 0 | 24.9 |
| A21 | 320 | NA | NA |
| A22 | 38 | 4 | 22.8 |
| A23 | 44 | 4 | 24.3 |
| A24 | 2400 | T$^e$ | 21.0 |

$^a$In centistokes at 25° C.
$^b$In degrees C., of a 1 percent by weight aqueous solution.
$^c$In dynes/cm, ± 1.5, of a 1 percent by weight aqueous solution.
$^d$Not available.
$^e$Turbid

TABLE 3

Type B Additives Imparting Water Wettability

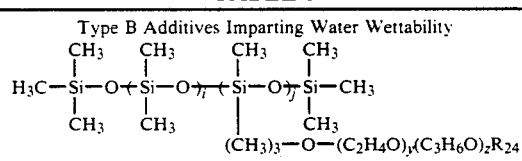

$(CH_3)_3-O-(C_2H_4O)_y(C_3H_6O)_zR_{24}$

| Additive Code | $R_{24}$ | i | j | y | z | MW | I.D. | Source |
|---|---|---|---|---|---|---|---|---|
| B01 | $CH_3$ | NA$^a$ | NA | NA | NA | 600 | L-77 | UC$^b$ |
| B02 | H | 0 | 1 | 10 | 2 | 836 | T-5847 | G$^c$ |
| B03 | $CH_3$ | 0 | 2 | 10 | 2 | 850 | T-5878 | G |
| B04 | $CH_3$ | NA | NA | NA | NA | 3000 | L-7602 | UC |
| B05 | n-$C_4H_9$ | NA | NA | NA | NA | 3000 | L-7500 | UC |
| B06 | H | 18 | 5 | 12 | 0 | 4724 | T-5842 | G |
| B07 | H | 20 | 5 | 3 | 10 | 5792 | T-5852 | G |
| B08 | H | 20 | 5 | 13 | 3 | 5962 | T-5851 | G |
| B09 | H | 18 | 5 | 16 | 2 | 6184 | T-5857 | G |
| B10 | H | 20 | 5 | 8 | 12 | 7472 | T-5873 | G |
| B11 | H | 43 | 5 | 22 | 23 | 15,444 | T-5863 | G |

$^a$Not available.
$^b$Union Carbide Corporation, Danbury, Connecticut.
$^c$Th. Goldschmidt AG, Essen, Federal Republic of Germany.

TABLE 4

Properties of the Type B Additives of Table 3

| Code | Viscosity$^a$ | Cloud Point$^b$ | Refractive Index$^c$ | Surface Tension |
|---|---|---|---|---|
| B01 | 20 | 10 | NA$^d$ | 21$^e$ |
| B02 | 100 | 45 | NA | 23$^f$ |
| B03 | 25 | T$^g$ | 1.446 | 20$^f$ |
| B04 | 100 | 0 | NA | 22$^e$ |
| B05 | 175 | 1$^h$ | NA | NA |
| B06 | 560 | 80 | 1.450 | 30$^f$ |
| B07 | 290 | 10 | 1.444 | NA |
| B08 | 430 | 65 | 1.450 | 30$^f$ |
| B09 | 580 | 84 | 1.449 | 28$^f$ |
| B10 | 440 | 30 | 1.449 | 28$^f$ |

TABLE 4-continued

Properties of the Type B Additives of Table 3

| Code | Viscosity[a] | Cloud Point[b] | Refractive Index[c] | Surface Tension |
|------|-----------|-------------|-----------------|-----------------|
| B11  | 2700      | 42          | 1.450           | 30[f]           |

[a] In centistokes at 25° C.
[b] In degrees C., of a 1 percent by weight solution.
[c] At 20° C., ± 0.005.
[d] Not available.
[e] In dynes/cm. ± 1.5, of a 0.1 percent by weight aqueous solution.
[f] In dynes/cm. ± 1.5, of a 0.1 percent by weight aqueous solution.
[g] Turbid
[h] Insoluble.

TABLE 5

Type C Additive Imparting Water Wettability $$R_{21}-Si[(-O-Si\frac{}{g}(OC_2H_4)_y(OC_3H_6)_z-OR_{24}]_3$$
with $CH_3$ groups on Si.

| Add. Code | $R_{21}$ | $R_{24}$ | g | y | z | MW | I.D. | Source |
|-----------|----------|----------|---|---|---|------|-------|--------|
| C01 | n-C₄H₉ | NA[a] | NA | NA | NA | 8000 | L-720 | UC[b] |

[a] Not available.
[b] Union Carbide Corporation, Danbury, Connecticut.

TABLE 6

Properties of the Type C Additive of Table 3

| Code | Viscosity[a] | Cloud Point[b] | Refractive Index[c] | Surface Tension[d] |
|------|-----------|-------------|-----------------|--------------------|
| C01  | 1100      | 42          | NA[e]           | 29                 |

[a] In centistokes at 25° C.
[b] In degrees C., of a 1 percent by weight aqueous solution.
[c] At 20° C., ± 0.005.
[d] In dynes/cm. ± 1.5, of a 0.1 percent by weight aqueous solution.
[e] Not available.

TABLE 7

Additives Imparting Characteristics Other Than Water Wettability

| Additive Code | Structure | Source |
|---------------|-----------|--------|
| D01[a,b] | $(CH_3)_3Si-(O-Si(CH_3)\frac{}{74}O-Si(CH_3)(CH_2)_3-O-Si(CH_3)_3$ with side chain $CHOH-CH_2R_{69}$ | Ex. 1 |
| D02[c,d] | $(CH_3)_3Si-(O-Si(CH_3)\frac{}{74}O-Si(CH_3)(CH_2)_3-O-Si(CH_3)_3$ with side chain $CHOH-CH_2R_{70}$ | Ex. 2 |
| D03[e] | $(CH_3)_3Si-O-(Si(CH_3)-O)_{74}Si(CH_3)_3$ with side chain $(CH_2)_3-O-CH-CH_2-N[CH(CH_3)_2]_2$ with $OH$ | G[f] |

TABLE 7-continued

Additives Imparting Characteristics Other Than Water Wettability

| Additive Code | Structure | Source |
|---------------|-----------|--------|
| D04[g] | $(CH_3)_3Si-O-(Si(CH_3)-O)_{32}Si(CH_3)_3$ with side chain $CH_2-CH_2-CF_3$ | P[h] |
| D05[i] | $(CH_3)_3Si-O-(Si(CH_3)-O)_{122}Si(CH_3)_3$ with $CH_3$ | P[j] |

[a] Imparts ultraviolet radiation absorption.
[b] $R_{69}$ is 2-(2-hydroxy-3-t-butyl-5-methylphenyl)-2H-benzotriazol-5-yl, lithium salt.
[c] Imparts light stabilization by deactivating excited oxygen molecules or terminating free radicals.
[d] $R_{70}$ is poly(N-β-hydroxyethyl-2,2,6,6-tetramethyl-4-hydroxypiperidyl succinate) covalently coupled through an ether linkage via the 4-hydroxy group of the terminal piperidyl moiety.
[e] Imparts buffering capacity against hydrogen ions.
[f] D-1059, Th. Goldschmidt AG, Essen, Federal Republic of Germany.
[g] Imparts a low surface energy.
[h] PS-182, Petrarch Systems, Bristol, Pennsylvania.
[i] A control additive which lacks a moiety B.
[j] PS-042, Petrarch Systems, Bristol, Pennsylvania.

TABLE 8

Properties of the Additives of Table 7

| Code | Viscosity[a] | Refractive Index[b] | Surface Tension[c] |
|------|-----------|------------------|--------------------|
| D01  | NA[d]     | NA               | NA                 |
| D02  | NA        | NA               | NA                 |
| D03  | NA        | NA               | NA                 |
| D04  | 1,000     | 1.382            | NA                 |
| D05  | 500       | 1.403            | 21.1               |

[a] In centistokes at 25° C.
[b] At 20° C., ± 0.005.
[c] In dynes/cm.
[d] Not available.

Example 1

Preparation of Additive D01

A 100-ml, three-necked, round-bottomed flask was fitted with a pressure-equalized side arm addition funnel, condenser, and rubber septum. The addition funnel and condenser also were fitted with rubber septa. The flask was purged continuously with dry nitrogen (Matheson extra dry grade) which was introduced via a syringe needle inserted through the rubber septum fitted on one of the tree necks of the flask; the nitrogen exited via another syringe needle inserted through the condenser-mounted rubber septum. Using a syringe, the flask was charged with 0.5 g (1.56 mmole) of 2-(2-hydroxy-3-t-butyl-5-methylphenyl)-5-chlorobenzotriazole (TINUVIN 326, Ciba-Geigy Corporation, Hawthorne, N.Y.) dissolved in 30 ml of dry tetrahydrofuran (THF) (Gold Label, 99.9 percent, Aldrich Chemical Company, Inc., Milwaukee, Wis.). The resulting solution was cooled in a dry ice/acetone bath to a temperature of about −78° while being stirred with a magnetic stirrer. To the cold solution was slowly added dropwise 0.48 g of lithium diisopropylamine (Aldrich Chemical Company, Inc.) in approximately 5 ml of THF which had been added via a syringe to the addition funnel. The resulting mixture was stirred for one hour, after which time 0.91 g (1.56 mmole) of a compound having the following formula (TEGOPREN 3010, Th. Goldschmidt AG, Essen, Federal Republic of Germany), dissolved in about 5 ml of THF, was added dropwise by means of the addition funnel (charged by syringe injection, over a 20-minute period:

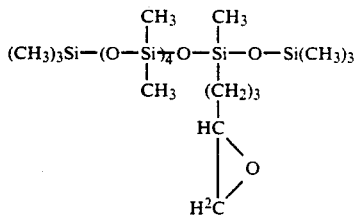

The resulting mixture was was allowed to warm to ambient temperature, with stirring. The mixture was allowed to stir for four hours, after which time the solvent was removed under reduced pressure by means of a rotating evaporator (Buchi Rotovap, Model RE 120). The residue was a pale yellow wax. Infrared analysis of the material showed absorption maxima at 3600 and 3100 cm$^{-1}$.

Example 2

Preparation of Additive D02

The procedure of Example 1 was repeated, except that the 2-(2-hydroxy-3-t-butyl-5-methylphenyl)-5-chlorobenzotriazole was replaced with 10 g (4 mmole) of poly(N-$\beta$-hydroxyethyl-2,2,6,6-tetramethyl-4-hydroxypiperidyl succinate) having a molecular weight of approximately 2300 (TINUVIN 622 LD, Ciba-Geigy Corporation, Ardsley, N.Y.), the lithium diisopropylamine was replaced with 0.26 g (4 mmole) of butyl lithium (Aldrich Chemical Company, Inc.), and the amount of TEGOPREN 3010 was increase to 2.4 g (4 mmole). The yield of additive was 9.6 g (77 percent).

B. Polymers

The polymers employed are summarized in Table 9 which is based on data supplied by the manufacturers. In the table, the melt flow rate is given in the column labeled "MFR" and was determined in accordance with ASTM Test Method D1238-82, "Standard Test Method for Flow Rates of Thermoplastics by Extrusion Plastometer." The polydispersity, PD, is the ratio of the weight-average molecular weight, $M_w$, to the number-average molecular weight, $M_n$.

TABLE 9

| Polymer Code | MFR | PD | $M_n$ | $M_w$ | Temp. Range[a] |
|---|---|---|---|---|---|
| PPA[b] | 35 | 2.7 | 52,000 | 140,000 | 293–316 |
| PPB[c] | 400 | 4.0 | 17,000 | 68,000 | 254–304 |
| PPC[d] | 400 | 4.0 | 17,000 | 68,000 | 254–304 |
| PPD[e] | 60 | 4.0 | 30,000 | NA[f] | NA |
| PPE[g] | NA | NA | NA | NA | 204–260 |
| PPF[h] | NA | NA | NA | NA | NA |
| PEA[i] | NA | NA | NA | NA | NA |
| PEB[j] | NA | NA | NA | NA | NA |
| PSA[k] | NA | NA | NA | NA | 245[l] |

[a]Degrees C.
[b]Type PC-973 polypropylene, Himont Incorporated, Wilmington, Delaware.
[c]Type PF-441 polypropylene, Himont Incorporated.
[d]Type PF-015 polypropylene, Himont Incorporated; the polymer is type PF-441 to which has been added 500 ppm of Lubrizol 101 (Lubrizol, Inc., Wickliffe, Ohio).
[e]Type PF-444 polypropylene, Himont Incorporated.
[f]Not available.
[g]Type 5A08 polypropylene, Shell Chemical Co., Houston, Texas; melt index, 3.0 g/10 min.; and specific gravity, 0.903.
[h]Type WRS-5-144 polypropylene, Shell Chemical Co., Houston, Texas.
[i]Type 61800.06 low density polyethylene, Dow Chemical Co., Midland, Michigan.
[j]Type 3404 low density polyethylene, Norchem, Inc., Rolling Meadows, Illinois; melt index, 1.8 g/10 min.; and density, 0.922 g/cm$^3$.
[k]Type PET 7352 poly(ethylene terephthalate), Eastman Chemical Products, Inc., Kingsport, Tennessee; melt index, 1.2 g/10 min.; and specific gravity, 1.4.
[l]Recommended melt processing temperature.

II. Preparation of Compositions

Surface-segregatable thermoplastic, melt-extrudable compositions as provided by the present invention were prepared by several methods. However, only those methods are described below which permitted isolation of the composition prior to a melt-processing step; i.e., a bench-scale method and a pilot-scale method. The preparations of compositions simultaneously with melt-processing are described in conjunction with such melt-processing.

Examples 3–49

A. Bench-Scale Method

Approximately 10 g of a polymer in pellet form was mixed in a beaker with the desired amount of additive. The resulting mixture was poured into the hopper of a small compounding unit (Max Mixing Extruder, No. CS-194-FA-093, Custom Scientific Instruments, Inc., New York, N.Y.). The mixture was heated in the extruder of the compounder to a temperature of 180° and extruded through a die having a single, approximately 4-mm diameter, orifice. The extruded composition was collected either on aluminum foil or in a glass evaporating dish. The cooled material was cut manually into approximately 6-mm long pieces. The compositions prepared are summarized in Table 10.

TABLE 10

Summary of Bench-Scale Preparations of Compositions

| Example | Composition Code | Polymer Code | Additive(s) Code(s) | Wt. Percent |
|---|---|---|---|---|
| 3 | PP01-1 | PPA | A13 | 2 |
| 4 | PP02-1 | PPA | A18 | 1 |
| 5 | PP03-1 | PPA | A18 | 3 |
| 6 | PP04-1 | PPA | A20 | 1 |
| 7 | PP05-1 | PPA | A20 | 3 |
| 8 | PS01-1 | PSA | A20 | 2 |
| 9 | PS02-1 | PSA | A20 | 5 |
| 10 | PP06-1 | PPA | A21 | 1 |
| 11 | PP07-1 | PPA | A21 | 3 |
| 12 | PE01-1 | PEA | A21 | 1 |
| 13 | PE02-1 | PEA | A21 | 3 |
| 14 | PS03-1 | PSA | A23 | 2 |
| 15 | PP08-1 | PPA | B01 | 1 |
| 16 | PP09-1 | PPA | B01 | 2 |
| 17 | PP10-1 | PPA | B01 | 3 |
| 18 | PE03-1 | PEA | B01 | 1 |
| 19 | PE04-1 | PEA | B01 | 3 |
| 20 | PP11-1 | PPA | B04 | 1 |
| 21 | PP12-1 | PPA | B04 | 3 |
| 22 | PE05-1 | PEA | B04 | 1 |
| 23 | PE06-1 | PEA | B04 | 3 |

TABLE 10-continued

Summary of Bench-Scale Preparations of Compositions

| Example | Composition Code | Polymer Code | Additive(s) Code(s) | Wt. Percent |
|---|---|---|---|---|
| 24 | PP13-1 | PPA | B05 | 1 |
| 25 | PP14-1 | PPA | B05 | 3 |
| 26 | PE07-1 | PEA | B05 | 1 |
| 27 | PE08-1 | PEA | B05 | 3 |
| 28 | PP15-1 | PPA | B06 | 3 |
| 29 | PP16-1 | PPA | B09 | 3 |
| 30 | PP17-1 | PPA | B10 | 3 |
| 31 | PP18-1 | PPA | C01 | 1 |
| 32 | PP19-1 | PPA | C01 | 3 |
| 33 | PE09-1 | PEA | C01 | 1 |
| 34 | PE10-1 | PEA | C01 | 3 |
| 35 | PE11-1 | PEA | D01 | 1 |
| 36 | PE12-1 | PEA | D01 | 3 |
| 37 | PE13-1 | PEA | D02 | 3 |
| 38 | PE14-1 | PEA | D03 | 3 |
| 39 | PP20-1 | PPA | D04 | 3 |
| 40 | PP21-1 | PPA | D05 | 3 |
| 41 | PP22-2 | PPA | B02 | 1.5 |
|   |   |   | B11 | 1.5 |
| 42 | PP23-2 | PPA | B06 | 1.5 |
|   |   |   | B10 | 1.5 |
| 43 | PP24-2 | PPA | B10 | 1.5 |
|   |   |   | B11 | 1.5 |
| 44 | PP25-3 | PPA | B04 | 0.33 |
|   |   |   | B05 | 0.33 |
|   |   |   | C01 | 0.33 |
| 45 | PP26-3 | PPA | B04 | 1 |
|   |   |   | B05 | 1 |
|   |   |   | C01 | 1 |
| 46 | PP27-3 | PPA | B04 | 1.67 |
|   |   |   | B05 | 1.67 |
|   |   |   | C01 | 1.67 |
| 47 | PE15-3 | PEA | B04 | 0.33 |
|   |   |   | B05 | 0.33 |
|   |   |   | C01 | 0.33 |
| 48 | PE16-3 | PEA | B04 | 1 |
|   |   |   | B05 | 1 |
|   |   |   | C01 | 1 |
| 49 | PE17-3 | PEA | B04 | 1.67 |
|   |   |   | B05 | 1.67 |
|   |   |   | C01 | 1.67 |

Examples 50-130

B. Pilot-Scale Method

To a weighed amount of polymer, typically from about 13 to about 45 kg, in a plastic-lined fiber drum was added the desired amount of additive. The components then were mixed mechanically in a paddle mixer (Banbury, Ann Arbor, Mich.). The hopper of a twin-screw compound unit (Egan Machinery Company, Sommerville, N.J.) was charged with the resulting mixture. The mixture was gravity-fed to the compound screws. Compounding was accomplished at a temperature of from about 180° to about 250°, depending on the polymer employed. The resulting composition was extruded though a die having six orifices with diameters of about 3 mm. The extruded filaments were passed through a ten-foot water bath and then a forced-air blower. The dried filaments were pelletized in a rotary pelletizer (Cumberland Company, New York, N.Y.) and stored in 23-kg lots in plastic-lined boxes. The resulting compositions are summarized in Table 11. In some case, an elemental analysis was carried out on the composition by Galbraith Laboratories, Inc., Knoxville, Tenn. The results of the elemental analyses are summarized in Table 12.

TABLE 11

Summary of Pilot-Scale Preparations of Compositions

| Example | Composition Code | Polymer Code | Additive(s) Code(s) | Wt. Percent |
|---|---|---|---|---|
| 50 | PP28-1 | PPA | A21 | 1 |
| 51 | PP29-1 | PPA | A21 | 3 |
| 52 | PP30-1 | PPA | A21 | 5 |
| 53 | PP31-1 | PPA | A21 | 12 |
| 54 | PE18-1 | PEA | A21 | 1 |
| 55 | PE19-1 | PEA | A21 | 3 |
| 56 | PE20-1 | PEA | A21 | 5 |
| 57 | PP32-1 | PPA | B01 | 3 |
| 58 | PP33-1 | PPA | B01 | 5 |
| 59 | PP34-1 | PPB | B01 | 3 |
| 60 | PP35-1 | PPB | B01 | 5 |
| 61 | PP36-1 | PPC | B01 | 3 |
| 62 | PP37-1 | PPC | B01 | 5 |
| 63 | PE21-1 | PEA | B01 | 3 |
| 64 | PE22-1 | PEA | B01 | 5 |
| 65 | PP38-1 | PPA | B02 | 3 |
| 66 | PP39-1 | PPA | B02 | 5 |
| 67 | PP40-1 | PPC | B02 | 3 |
| 68 | PP41-1 | PPC | B02 | 5 |
| 69 | PP42-1 | PPA | B03 | 3 |
| 70 | PP43-1 | PPA | B03 | 5 |
| 71 | PP44-1 | PPC | B03 | 3 |
| 72 | PP45-1 | PPC | B03 | 5 |
| 73 | PP46-1 | PPA | B04 | 3 |
| 74 | PP47-1 | PPA | B04 | 5 |
| 75 | PE23-1 | PEA | B04 | 3 |
| 76 | PE24-1 | PEA | B04 | 5 |
| 77 | PP48-1 | PPA | B05 | 3 |
| 78 | PP49-1 | PPA | B05 | 5 |
| 79 | PE25-1 | PEA | B05 | 3 |
| 80 | PE26-1 | PEA | B05 | 5 |
| 81 | PP50-1 | PPA | B06 | 3 |
| 82 | PP51-1 | PPA | B06 | 5 |
| 83 | PP52-1 | PPC | B06 | 3 |
| 84 | PP53-1 | PPC | B06 | 5 |
| 85 | PP54-1 | PPA | B07 | 3 |
| 86 | PP55-1 | PPA | B07 | 5 |
| 87 | PP56-1 | PPC | B07 | 3 |
| 88 | PP57-1 | PPC | B07 | 5 |
| 89 | PP58-1 | PPA | B08 | 3 |
| 90 | PP59-1 | PPA | B08 | 5 |
| 91 | PP60-1 | PPC | B08 | 3 |
| 92 | PP61-1 | PPC | B08 | 5 |
| 93 | PP62-1 | PPA | B09 | 2 |
| 94 | PP63-1 | PPA | B09 | 3 |
| 95 | PP64-1 | PPA | B09 | 5 |
| 96 | PP65-1 | PPC | B09 | 3 |
| 97 | PP66-1 | PPC | B09 | 5 |
| 98 | PP67-1 | PPA | B10 | 3 |
| 99 | PP68-1 | PPA | B10 | 5 |
| 100 | PP69-1 | PPC | B10 | 3 |
| 101 | PP70-1 | PPC | B10 | 5 |
| 102 | PP71-1 | PPA | B11 | 3 |
| 103 | PP72-1 | PPA | B11 | 5 |
| 104 | PP73-1 | PPC | B11 | 3 |
| 105 | PP74-1 | PPC | B11 | 5 |
| 106 | PP75-1 | PPA | C01 | 1 |
| 107 | PP76-1 | PPA | C01 | 3 |
| 108 | PP77-1 | PPA | C01 | 5 |
| 109 | PE27-1 | PEA | C01 | 1 |
| 110 | PE28-1 | PEA | C01 | 3 |
| 111 | PE29-1 | PEA | C01 | 5 |
| 112 | PP78-1 | PPA | D03 | 3 |
| 113 | PP79-1 | PPA | D04 | 3 |
| 114 | PP80-1 | PPA | D05 | 3 |
| 115 | PP81-2 | PPA | B02 | 1 |
|   |   |   | B11 | 1 |
| 116 | PP82-2 | PPA | B02 | 1.5 |
|   |   |   | B11 | 1.5 |
| 117 | PP83-2 | PPA | B06 | 1 |
|   |   |   | B10 | 1 |
| 118 | PP84-2 | PPA | B06 | 1.5 |
|   |   |   | B10 | 1.5 |
| 119 | PP85-2 | PPA | B10 | 1 |
|   |   |   | B11 | 1 |
| 120 | PP86-2 | PPA | B10 | 1.5 |
|   |   |   | B11 | 1.5 |
| 121 | PP87-3 | PPA | B06 | 1 |

TABLE 11-continued

Summary of Pilot-Scale Preparations of Compositions

| Example | Composition Code | Polymer Code | Additive(s) Code(s) | Wt. Percent |
|---|---|---|---|---|
| 122 | PP88-3 | PPA | B09 | 1 |
|  |  |  | B10 | 1 |
|  |  |  | B06 | 1 |
|  |  |  | B09 | 1 |
|  |  |  | B11 | 1 |
| 123 | PP89-3 | PPA | B09 | 0.67 |
|  |  |  | B10 | 0.67 |
|  |  |  | B11 | 0.67 |
| 124 | PP90-3 | PPA | B04 | 0.33 |
|  |  |  | B05 | 0.33 |
|  |  |  | C01 | 0.33 |
| 125 | PP91-3 | PPA | B04 | 0.67 |
|  |  |  | B05 | 0.67 |
|  |  |  | C01 | 0.67 |
| 126 | PP92-3 | PPA | B04 | 1 |
|  |  |  | B05 | 1 |
|  |  |  | C01 | 1 |
| 127 | PP93-3 | PPA | B04 | 1.67 |
|  |  |  | B05 | 1.67 |
|  |  |  | C01 | 1.67 |
| 128 | PE30-3 | PEA | B04 | 0.33 |
|  |  |  | B05 | 0.33 |
|  |  |  | C01 | 0.33 |
| 129 | PE31-3 | PEA | B04 | 1 |
|  |  |  | B05 | 1 |
|  |  |  | C01 | 1 |
| 130 | PE32-3 | PEA | B04 | 1.67 |
|  |  |  | B05 | 1.67 |
|  |  |  | C01 | 1.67 |

TABLE 12

Elemental Analyses of Selected Compositions

| Example | Composition Code | % C | % H | % Si | % F |
|---|---|---|---|---|---|
| 50 | PP28-1 | 85.60 | 13.96 | 0.23 | — |
| 52 | PP30-1 | 84.28 | 13.54 | 0.77 | — |
| 65 | PP38-1 | 84.36 | 13.83 | 0.50 | — |
| 74 | PP47-1 | 84.44 | 13.50 | 0.47 | — |
| 78 | PP49-1 | 84.51 | 13.47 | 0.36 | — |
| 81 | PP50-1 | 84.90 | 13.79 | 0.77 | — |
| 93 | PP62-1 | 83.56 | 13.39 | 0.42 | — |
| 98 | PP67-1 | 84.49 | 13.65 | 0.47 | — |
| 102 | PP71-1 | 83.86 | 13.55 | 0.42 | — |
| 108 | PP77-1 | 84.05 | 13.58 | 0.38 | — |
| 112 | PP78-1 | 83.83 | 13.49 | 1.06 | 0.93 |
| 121 | PP87-3 | 84.30 | 13.70 | 0.45 | — |
| 122 | PP88-3 | 82.70 | 13.50 | 0.64 | — |
| 123 | PP89-3 | 84.36 | 13.74 | 0.33 | — |
| 124 | PP91-3 | 85.04 | 13.58 | 0.27 | — |
| 126 | PP92-3 | 85.11 | 13.59 | 0.52 | — |

It is evident from the data in Table 12 that each composition analyzed contained additive. However, the effectiveness of the additive remained to be demonstrated.

C. Hot-Stage Microscope Study

A hot-stage microscope study was conducted on several polymer-additive combinations in an effort to gain an insight into the compatibility aspect of the additive with the polymer. Although the study actually was done later in the program, it is reported here for convenience, except for one part which will be described in Section VI.

Briefly, polymer, either in the form of small granules or fibers, both with and without additives, was observed under a hot-stage microscope at two temperatures, 160° and 220°, at a magnification of 350×. The equipment consisted of a Mettler hot-stage and a Zeiss Universal optical microscope equipped with transmitted light optics. The presence of additive globules at either temperature was an indication of the incompatibility of the additive with the polymer at the temperature of observation. The study was conducted by Ricerca, Inc., Painesville, Ohio.

Figure 2A:
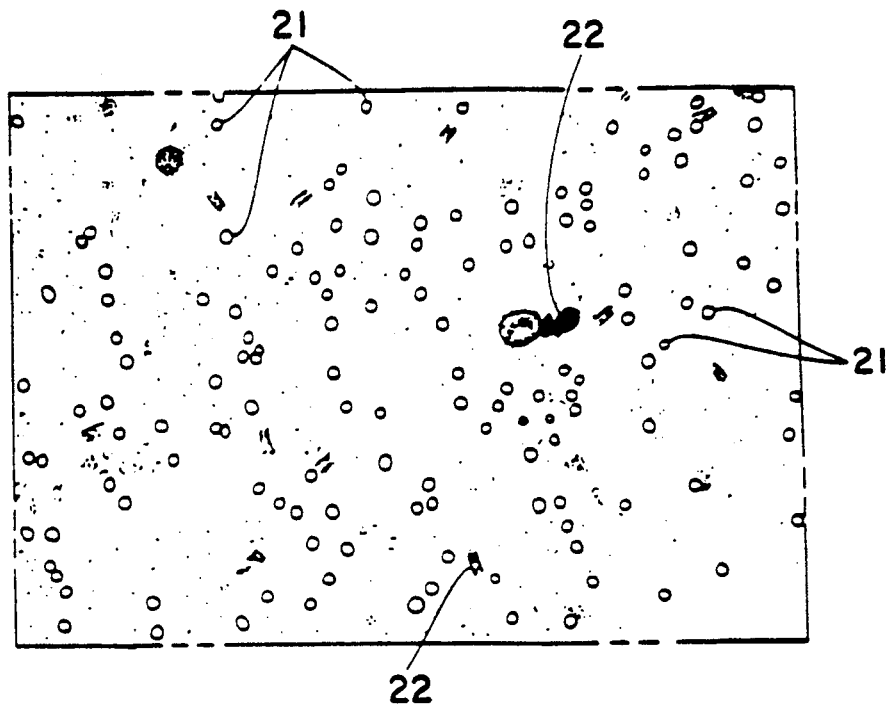
FIG. 2 consists of two hand-drawn representations of photomicrographs of a composition of the present invention, i.e., the fibers of Example 328, taken through a hot-stage microscope at two different temperatures and a magnification of 350×.
Figure 2B:
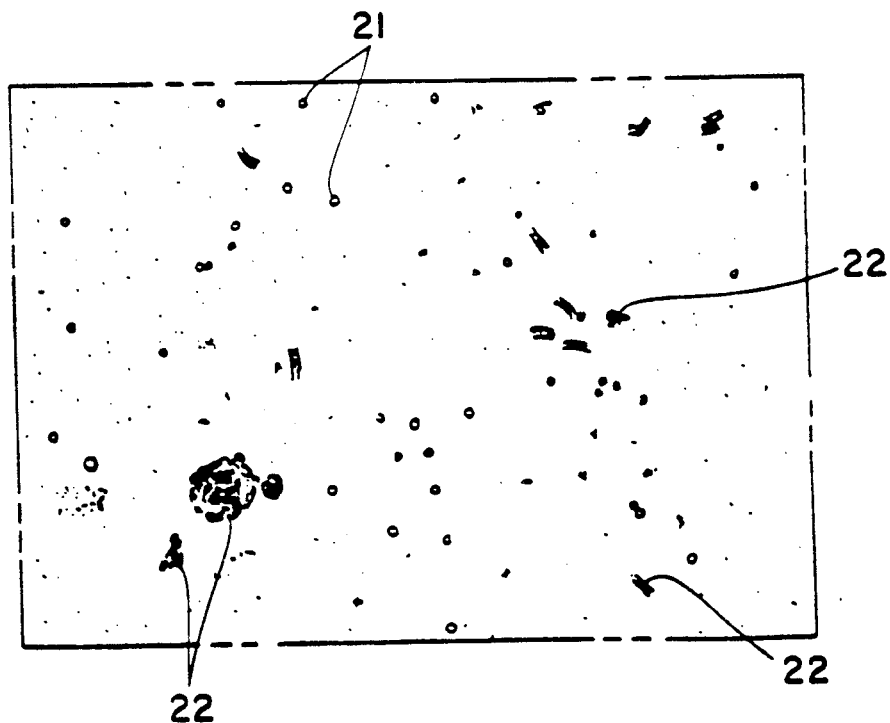

The first material studied was the web of Example 327 which was prepared from a composition of the present invention consisting of polymer PPA and 3 percent by weight of additive A11. FIG. 2A is a representation of the photomicrograph at 160° and FIG. 2B is a representation of the photomicrograph at 220°. In FIG. 2A, additive globules 21 clearly are present. Also present are what appear to be a few particles 22 of debris or foreign matter. At 220°, as seen in FIG. 2B, a few additive globules 21 seem to be present, but they appear to be slightly smaller in size. Again, some debris particles 22 are present.

The existence of a large number of additive globules at 160° demonstrates that the additive is incompatible with the polymer at that temperature. Moreover, the fact that the number of globules decreases significantly at 220° indicates that additive compatibility with the polymer has increased substantially. Since melt-extrusion temperatures for polymer PPA typically are in the range of from about 250° to about 300°, the additive clearly will be compatible with the polymer at melt extrusion temperatures.

Figure 3A:
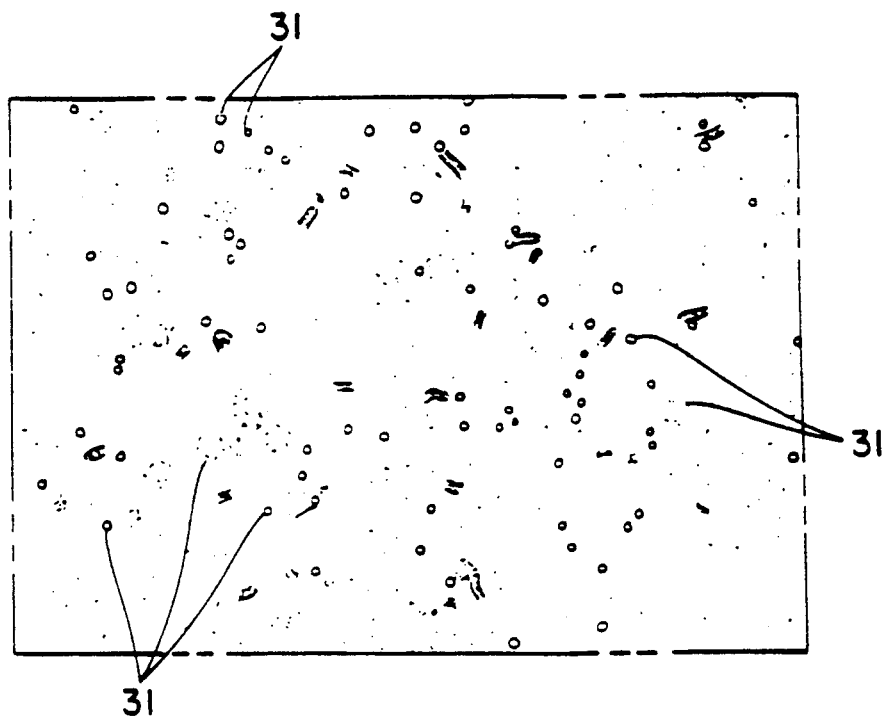
FIG. 3 consists of two hand-drawn representations of photomicrographs of the polymer component only of the fibers of Example 328, taken through a hot-stage microscope at two different temperatures and a magnification of 350×.
Figure 3B:
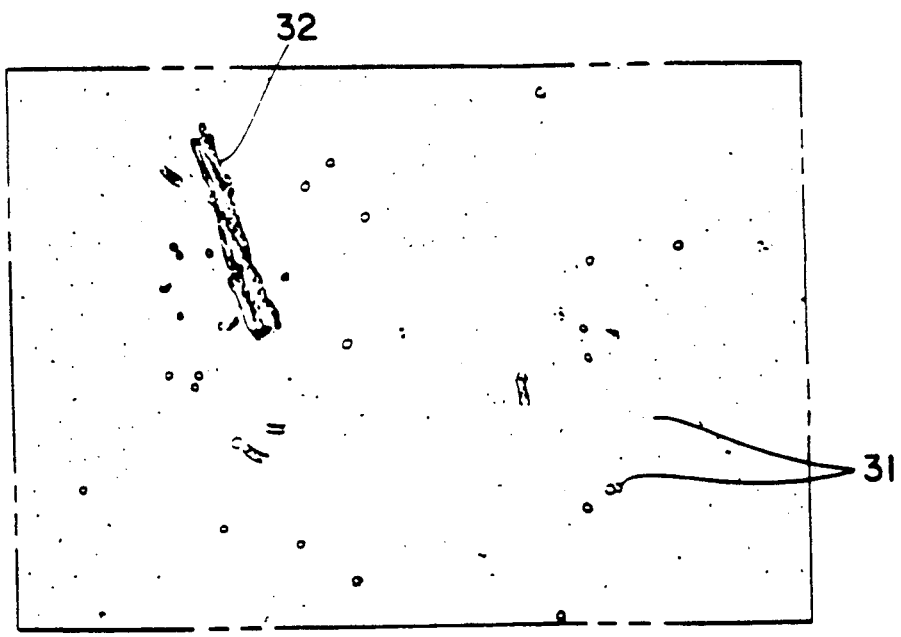

The second material consisted of polymer PPA alone as a negative control. FIGS. 3A and 3B are representations of the hot-stage photomicrographs at 160° and 220°, respectively. In FIG. 3A, crystallites 31 are seen. While not apparent from the Figures, such crystallites 31 differ in appearance and are distinguishable from additive globules, such as additive globules 21 in FIG. 2A. Upon heating to 220°, as shown by FIG. 3B, most of the crystallites 31 have disappeared; some debris 32 is present.

Figure 4A:
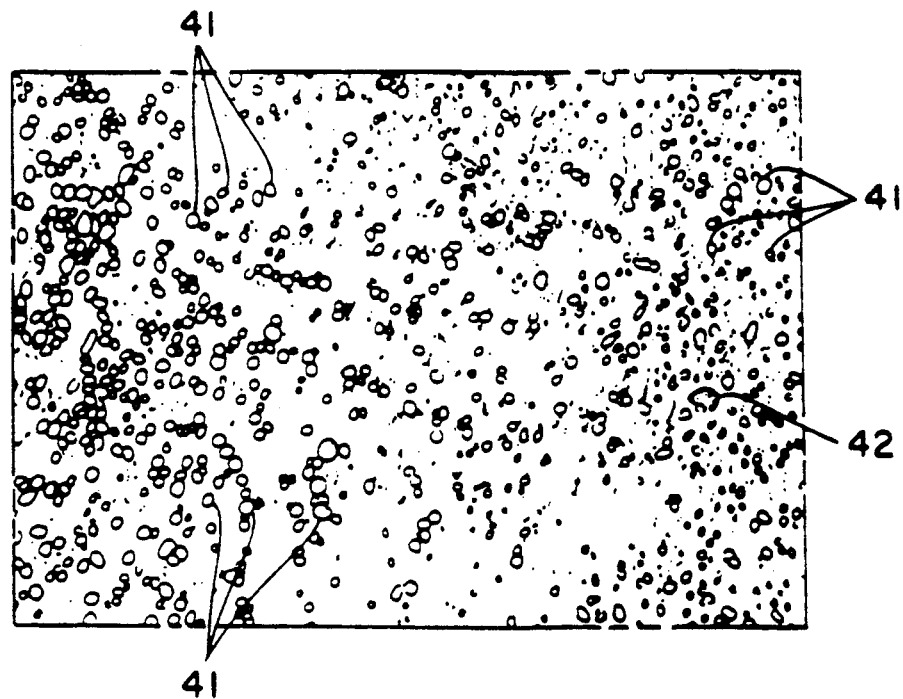
FIG. 4 consists of two hand-drawn representations of photomicrographs of the composition of Example 40 consisting of the polymer component of the fibers of Example 328 and an incompatible silicon-containing compound, taken through a hot-stage microscope at two different temperatures and a magnification of 350×.
Figure 4B:
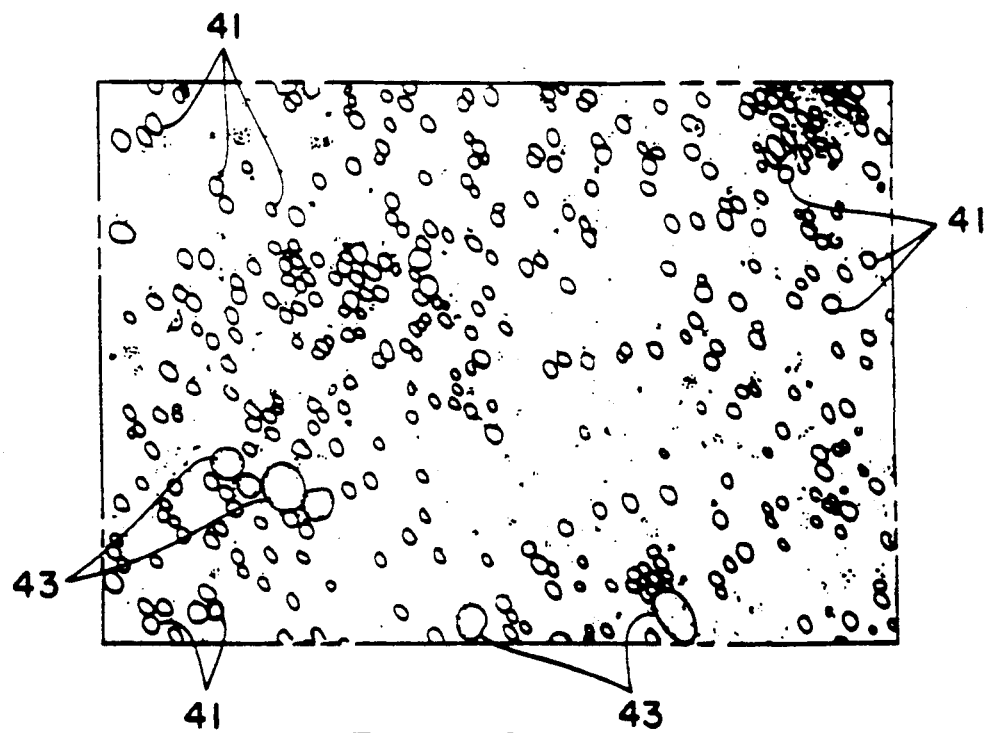

As a positive control, composition PP21-1 from Example 40 was studied under the same conditions. Representations of the photomicrographs are shown as FIGS. 4A and 4B. In both figures, numerous globules 41 of additive D05 are apparent. Some of such globules apparently have coalesced at the higher temperature to form droplets 43 (FIG. 4B). At least one debris particle 42 is seen in FIG. 4A.

The incompatibility of additive D05 in polymer PPA at both 160° and 220° is striking, especially when FIG. 4B is compared with FIG. 2B. Moreover, it is clear that the additive becomes less compatible with the polymer as the temperature of the polymer increases.

Figure 5A:
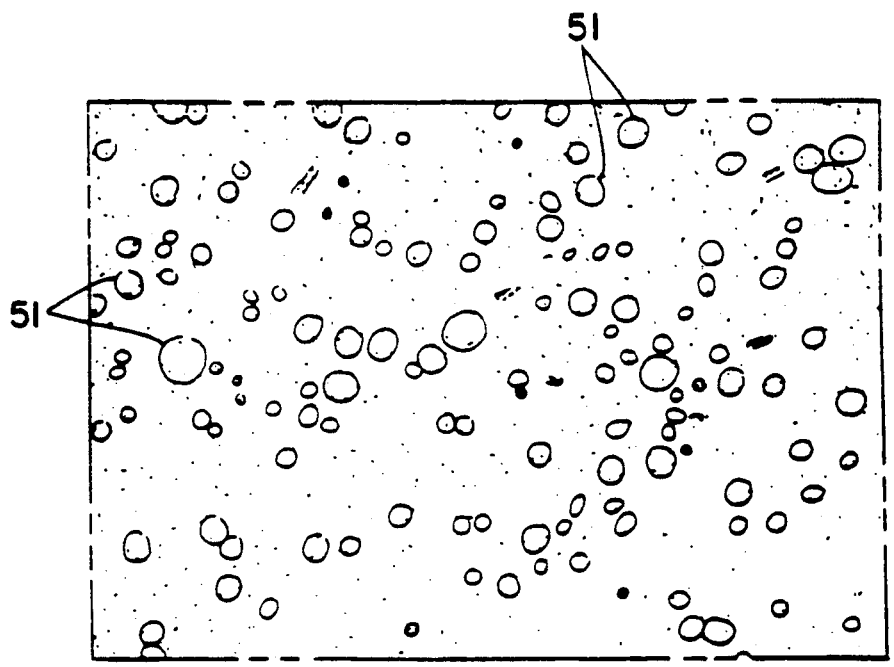
FIG. 5 consists of two hand-drawn representations of photomicrographs of the composition of Example 45, taken through a hot-stage microscope at two different temperatures and a magnification of 350×.

This discussion of the hot-stage microscope study concludes with the results obtained with composition PP26-3 from Example 45. That composition, it will be recalled, consists of polymer PPA and a mixture of additives having molecular weights of 3,000, 3,000, and 8,000, respectively. The presence of additive globules 51 is seen in FIG. 5A which represents the hot-stage photomicrograph at 160°. Such globules appear to be nearly gone at 220° (FIG. 5B).

Figure 5B:
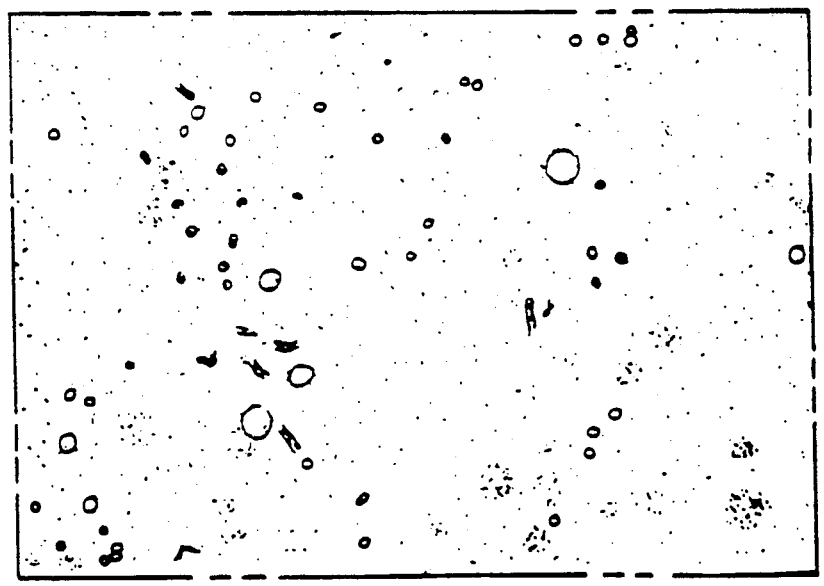

Thus, FIGS. 5A and 5B are similar to FIGS. 2A and 2B, respectively, and demonstrate that the additive mixture changes from incompatible to compatible as the temperature of the polymer is raised from 160° to 220°.

Several other compositions of the present invention were included in the hot-stage microscope study with results similar to those shown in FIGS. 2A, 2B, 5A, and 5B.

From the foregoing, it is apparent that the use of the hot-stage microscope as just described can be used as a simple method for determining whether or not any given additive or additive mixture is likely to segregate in a controlled manner to the surface of a fiber or film as described herein. If the additive or additive mixture forms globules which remain at both 160° and 220°, the probability is that such additive or additive mixture will not segregate to one or more of the interfacial surface, effective surface, and subsurface. In addition, the melt-processing of a composition incorporating therein such additive or additive mixture probably will not be successful. On the other hand, if the additive or additive mixture does not form globules at 160°, the additive or additive mixture is compatible with the polymer at temperatures below melt-extrusion temperatures and probably will remain distributed throughout the bulk of the resulting fiber or film without any controlled segregation toward the surface.

III. Preparation of Melt-Pressed Films

Examples 131–176

As an initial screening method, films were pressed from various of the compositions prepared and described in Section II, above. The apparatus employed was a Carver Laboratory Press, Model 2518 (Fred S. Carver, Inc., Menomonee Falls, Wis.) having heated plates. From about 1 to about 10 g of a composition was placed between two sheets of aluminum foil and the resulting assembly was placed on the bottom plate of the press, the plates having been preheated to about 180°. Pressure up to about 10,000 psig was applied and maintained for no more than about 5 seconds. The pressure was released and the foil sandwich was removed from the press. The foil was removed and the film thus obtained was stored in a plastic bag. Film thicknesses of from about 1 to about 5 microns typically were obtained. The wettability of each film made with a type A, B, or C additive was qualitatively estimated by simply placing a drop of water on the surface and observing whether or not the drop wet the surface of the film. The films obtained and the results of the wettability screen are summarized in Table 13.

TABLE 13

Summary of Melt-Pressed Films Prepared from Compositions Prepared in Section II

| Example | Composition Example | Code | Wettability |
|---|---|---|---|
| 131 | 3 | PP01-1 | Positive |
| 132 | 4 | PP02-1 | Positive |
| 133 | 5 | PP03-1 | Positive |
| 134 | 6 | PP04-1 | Positive |
| 135 | 7 | PP05-1 | Positive |
| 136 | 8 | PS01-1 | Positive |
| 137 | 9 | PS02-1 | Positive |
| 138 | 10 | PP06-1 | Positive |
| 139 | 11 | PP07-1 | Positive |
| 140 | 12 | PE01-1 | Positive |
| 141 | 13 | PE02-1 | Positive |
| 142 | 14 | PS03-1 | Positive |
| 143 | 15 | PP08-1 | Positive |
| 144 | 16 | PP09-1 | Positive |
| 145 | 17 | PP10-1 | Positive |
| 146 | 18 | PE03-1 | Positive |
| 147 | 19 | PE04-1 | Positive |
| 148 | 20 | PP11-1 | Positive |
| 149 | 21 | PP12-1 | Positive |
| 150 | 22 | PE05-1 | Positive |
| 151 | 23 | PE06-1 | Positive |
| 152 | 24 | PP13-1 | Positive |
| 153 | 25 | PP14-1 | Positive |

TABLE 13-continued

Summary of Melt-Pressed Films Prepared from Compositions Prepared in Section II

| Example | Composition Example | Code | Wettability |
|---|---|---|---|
| 154 | 26 | PE07-1 | Positive |
| 155 | 27 | PE08-1 | Positive |
| 156 | 28 | PP15-1 | Positive |
| 157 | 29 | PP16-1 | Positive |
| 158 | 30 | PP17-1 | Positive |
| 159 | 31 | PP18-1 | Positive |
| 160 | 32 | PP19-1 | Positive |
| 161 | 33 | PE09-1 | Positive |
| 162 | 34 | PE10-1 | Positive |
| 163 | 35 | PE11-1 | N/A[a] |
| 164 | 36 | PE12-1 | N/A |
| 165 | 37 | PE13-1 | N/A |
| 166 | 38 | PE14-1 | N/A |
| 167 | 39 | PP20-1 | N/A |
| 168 | 40 | PP21-1 | N/A |
| 169 | 41 | PP22-2 | Positive |
| 170 | 42 | PP23-2 | Positive |
| 171 | 43 | PP24-2 | Positive |
| 172 | 44 | PP25-3 | Positive |
| 173 | 45 | PP26-3 | Positive |
| 174 | 46 | PP27-3 | Positive |
| 175 | 47 | PE15-3 | Positive |
| 176 | 48 | PE16-3 | Positive |
| 177 | 49 | PE17-3 | Positive |

[a]Not applicable, since the additive was not designed to impart water wettability.

In an effort to obtain some indication of the preferential segregation of additive(s) to the surface of the melt-pressed films, a sample of the film of Example 173 was subjected to scanning electron microscopy in conjunction with a silicon x-ray probe (Si-SEM) in accordance with standard procedures. The scanning electron microscope was manufactured by Cambridge Instruments, Cambridge, England, and the x-ray probe was manufactured by Princeton Gamma Tech, Princeton, Calif.

Figure 6:
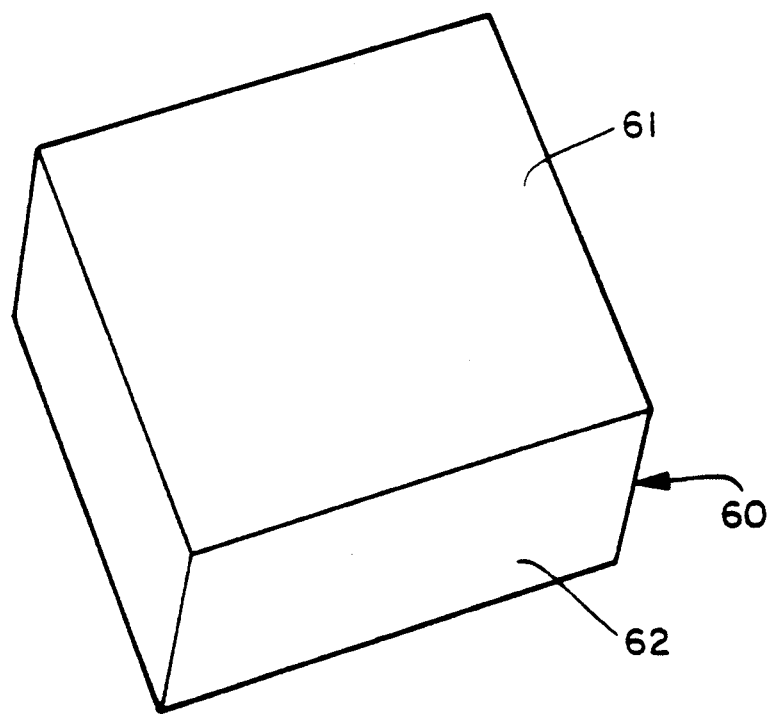
FIG. 6 is a diagrammatic representation of a section of melt-pressed film prepared from a composition of the present invention, as described in Examples 131–176, inclusive.
Figure 7:
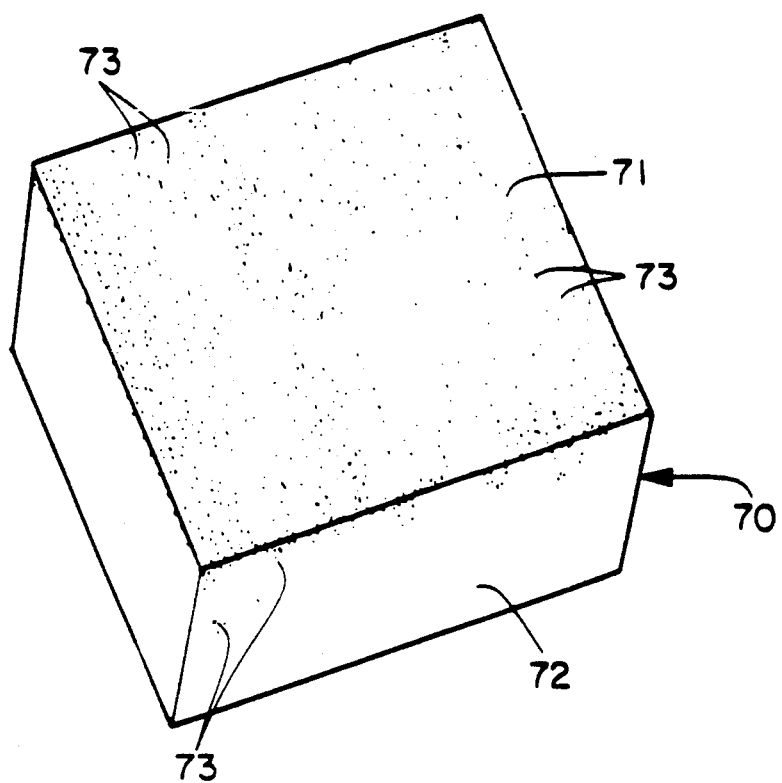
FIG. 7 is a diagrammatic representation of a scanning electron micrograph, using a silicon x-ray probe, of a sample of the film of Example 172, superimposed on the diagrammatic representation of FIG. 6, which film was prepared from a composition of the present invention in which the additive was a silicon-containing compound.

The sample of the film of Example 173 is represented diagrammatically by FIG. 6, in which film sample 60 has top surface 61 and front end surface 62. FIG. 7 is the diagrammatic representation of FIG. 6 on which has been superimposed the results of the Si-SEM. In FIG. 7, film sample 70 has top surface 71 and front end surface 72. Each of dots 73 represents the presence of silicon atoms.

It is clear the additives included in the composition from which the film of Example 173 was prepared have segregated preferentially to the surface region of the film. The absence of silicon in the core region of the film is striking. The irregular distribution of silicon along top surface 71 (FIG. &) is believed to have resulted from the irregularities present in the surface of the top plate of the press. Such irregularities include the generally streaked orientation of silicon atoms along surface 71.

Water contact angles were measured for several of the melt-pressed films. The apparatus employed was an NRL Goniometer, Model No. 100-00-115 (Ramé-Hart, Inc., Mountain Lakes, N.J. The water used was HPLC Grade water (Fisher Scientific, Pittsburgh, Pa.). The results of the measurements are summarized in Table 14.

TABLE 14

Water Contact Angles for Selected Melt-Pressed Films

| Film Example | Contact Angle, ° |
|---|---|
| 131 | <2 |
| 144 | <2 |
| 156 | 10 |

TABLE 14-continued

Water Contact Angles for Selected Melt-Pressed Films

| Film Example | Contact Angle. ° |
|---|---|
| 157 | 12 |
| 158 | 10 |
| 171 | 7 |
| Control[a] | 98 |
| 167 | 105 |
| 168[b] | 115 |

[a]Film pressed from virgin polymer (PPA) without any additive.
[b]Film pressed from the composition consisting of polymer PPA and additive D05 as a positive control.

The presence of either an additive intended to impart water wettability or an additive intended to increase the surface energy of the film clearly changed the contact angle measurement of the film relative to the control film which did not contain additive. Additives of the former type decreased the contact angle, as expected, and the additive of the latter type increased the contact angle, also as expected.

With respect to the two films which contained an additive which absorbed ultraviolet radiation, i.e., the films of Examples 163 and 164, they showed a broad, strong absorption band from 220 to 360 nm when analyzed on an ultraviolet spectrophotometer.

Samples of both films were subjected to electron spectroscopy for chemical analysis (ESCA). The ESCA data were collected by Surface Science Laboratories, Inc., Mountain View, Calif., using a Hewlett-Packard 5950 B spectrometer with a monochromatic aluminum K-alpha x-ray source. The scans were done with the open aperature setting for high sensitivity (low resolution). The x-ray power setting was 600–800 watts and charge neutralization was accomplished with a flood gun setting of 13 electron volts. The vacuum utilized was $10^{-8}$ Torr. The area analyzed was about $1 \times 4$ mm and the sampling depth was about 100 Å.

In addition, each film was subjected to bulk elemental analysis. The ESCA data and the results of the elemental analyses are summarized in Table 15.

barrier detectors. Data analysis involved the TOS source code written by Charles Evans & Associates and owned by General Ionics Corporation. The energy losses of the scattered helium nuclei give information on the nature and depth of the target atoms in the polymer matrix. The results are summarized in Table 16.

TABLE 16

Summary of RBS Analyses on Melt-Pressed Films

| | | Atomic Concentration, Atom % | | | |
|---|---|---|---|---|---|
| Example | Depth, Å | C | O | Si | Ti |
| 144 | 0–500 | 30 | 0.3 | 0.09 | <0.01[a] |
|  | >500 | 30 | 0.1 | 0.03 | <0.01[a] |
| 173 | 0-14 500 | 30 | 1.0 | 0.56 | <0.01[a] |
|  | 500–1000 | 30 | 0.6 | 0.15 | <0.01[a] |
|  | >1000 | 30 | 0.1 | 0.04 | <0.01[a] |

[a]This concentration was at or near the detection limit; the actual concentration may be considerably lower.

Figure 8:
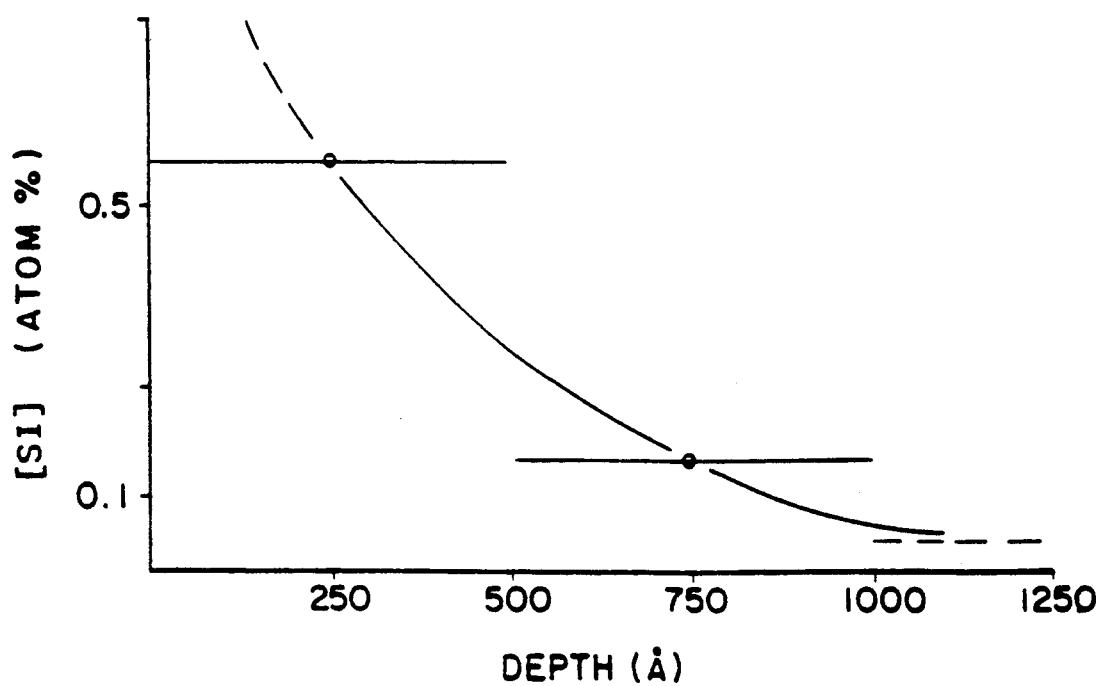
FIG. 8 is a plot of silicon concentration in atom percent versus depth in Å below the interfacial surface for a sample of the film of Example 172, the data for the plot having been obtained by Rutherford back scattering spectrometry.

The RBS data from Table 16 for the film of Example 173 were plotted as the atomic concentration of silicon in atom percent (y-axis) versus depth in Å (x-axis); the plot is shown as FIG. 8. In this and all subsequent plots of RBS data, the silicon concentrations were drawn parallel to the x-axis as liens which correspond to the depth field and the midpoints of such liens then were connected to obtain the curve shown in the plot. It is evident from FIG. 8 that most of the additives have segregated to the interfacial surface, effective surface, and subsurface of the film. Below a depth of around 1000–1250 Å, the concentration of silicon is very low, i.e., no more than about 0.04 atom percent.

The films from Examples 144 and 173 also were submitted for ESCA and bulk elemental analyses. The results of these analyses are shown in Table 17.

TABLE 17

Summary of ESCA Data and Elemental Analyses for the Films of Examples 144 and 172

| | ESCA Data | | | Bulk Elemental Anal. | | |
|---|---|---|---|---|---|---|
| Example | % C | % O | % Si | % C | % H | % Si |
| 144 | 94 | 4.4 | 1.3 | 84.21 | 13.32 | 0.24 |
| 173 | 62 | 25 | 12 | 85.11 | 13.59 | 0.52 |

It is apparent that the ESCA data and the RBS data cannot be correlated, partly because of the differences in the depths of measurements and partly because of the nonlinear concentration gradient which exists from the interfacial surface to the core of the film. Taken together, however, the data clearly establish the controlled segregation of additive toward the surface of the film.

Because ESCA analyses are limited to a depth of about 100 Å, two film samples were submitted for analysis by Rutherford back scattering (RBS) spectrometry. The analyses were carried out by Charles Evans & Associates, Redwood City, Calif. The apparatus employed was a General Ionics Model 4110 Tandem Accelerator (General Ionics Corporation. Newburyport, Mass.) using an Evans End Station (Charles Evans & Associates). A 2.275 MeV He++ ion probe was used, with a detection angle of 160°. Typical beam currents were 1–20 nanoamps. Ions were detected by surface

TABLE 15

Summary of ESCA Data and Elemental Analyses on Melt-Pressed Films Containing a UV Absorber

| | ESCA Data | | | | Bulk Elemental Analyses | | | |
|---|---|---|---|---|---|---|---|---|
| Example | % C | % O | % N | % Si | % C | % H | % N | % Si |
| 163 | 64 | 12 | 12 | 6 | 85.30 | 14.10 | 0.13 | 0.26 |
| 164 | 61 | 11 | 14 | 7 | 85.10 | 14.37 | 0.10 | 0.33 |

The evaluation of the film from Example 165 which contained additive D02 consisted of an accelerated ultraviolet radiation exposure trial. A sample of film measuring $3.8 \times 10$ cm, along with a control film pressed from virgin polymer, was suspended 0.91 m in front of a 400-Watt mercury arc lamp (Hanovia 674A10). Both films were exposed continuously for 12 hours. The films then were moved to a distance of 0.30 m from the lamps and exposed continuously for an additional 8 hours. Upon examining both films, it was found that the film of example 165 appeared to be unchanged, whereas the control film was brittle and could not be bent without breaking.

Before evaluating the film of Example 166 which contained buffering additive D03, the additive itself was examined for its buffering capabilities. This was done by charging a 50-ml beaker with 15 ml of deionized water and a small magnetic stirring bar. The beaker was placed on top of a magnetic stirrer and fitted with a calibrated pH electrode. The beaker then was charged with 0.032 g (1 drop) of TRITON X-102 (Rohm and Haas Co., Philadelphia, Pa.) and the pH of the resulting solution measured. To the solution in the beaker then was added 0.032 g (1 drop) of additive D03, followed by the measurement of the solution pH. Three additional, equal amounts of additive D03 were added sequentially, with the solution pH being measured after each addition. The results are presented in Table 18.

TABLE 18

Summary of pH Measurements of Aqueous Additive D03 Solutions

| Solution Composition | Solution pH |
| --- | --- |
| Water and 1 drop TRITON | 5.50 |
| Water, 1 drop TRITON, 1 drop D03 | 6.25 |
| Water, 1 drop TRITON, 2 drops D03 | 8.30 |
| Water, 1 drop TRITON, 3 drops D03 | 8.72 |

The solution containing 1 drop of TRITON X-102 and 3 drops of additive D03 (0.096 g) then was titrated with 0.01N hydrochloric acid. That is, incremental volumes of hydrochloric acid were added, with the pH of the solution being measured after each addition. The results are summarized in Table 19, which shows the cumulative volume of acid added.

TABLE 19

Titration of Additive D03 Solution

| Volume (ml) HCl Added | Solution pH |
| --- | --- |
| — | 8.72 |
| 0.2 | 6.55 |
| 0.5 | 6.91 |
| 1.0 | 6.73 |
| 2.0 | 6.74 |
| 3.0 | 6.70 |
| 4.0 | 6.62 |

It is clear the additive D03 is capable of acting as a buffer. The sharp drop in pH with the first addition of acid was expected, since a buffer system consists of a weak acid or base and its salt; consequently, buffering behavior could not be seen until acid had been added to form the salt of additive D03.

Having verified the buffering capability of additive D03, the procedure which provided the data for Table 19 was repeated, except that the three aliquots of additive D03 were replaced with a sample of the film of Example 166 weighing 0.211 g and only three 0.5-ml additions of hydrochloric acid were done. The results are summarized in Table 20; again, the cumulative volume of acid is shown.

TABLE 20

Titration of 0.211-g Sample of Film 166

| Volume (ml) HCl Added | Solution pH |
| --- | --- |
| None (sample absent) | 5.71 |
| None (sample present) | 5.91 |
| 0.5 | 5.90 |
| 1.0 | 5.90 |

TABLE 20-continued

Titration of 0.211-g Sample of Film 166

| Volume (ml) HCl Added | Solution pH |
| --- | --- |
| 1.5 | 5.75 |

The titration of a sample of the film of Example 166 was repeated, except that the film sample weighed 0.474 g. The results are shown in Table 21 which shows the cumulative volume of acid added.

TABLE 21

Titration of 0.474-g Sample of Film 166

| Volume (ml) HCl Added | Solution pH |
| --- | --- |
| None (sample absent) | 5.60 |
| None (sample present) | 6.70 |
| 0.5 | 6.69 |
| 1.0 | 6.69 |
| 1.5 | 6.69 |
| 2.0 | 6.60 |
| 2.5 | 6.40 |
| 3.0 | 4.60 |

Additive D03 not only retains its buffering capability when incorporated into a composition from which a film is formed, but also clearly is on the interfacial surface; otherwise, the additive could not buffer the solution in which the film was placed since the solution could not swell the film under the conditions of the test.

While the additives clearly segregated to the surfaces of the melt-pressed films and in general were effective in imparting to the film surfaces the desired characteristics, the critical test remained to be conducted; namely, the continuous preparation of melt-processed fibers or films to determine whether or not additive segregation will occur under the conditions encountered during fiber and film formation. Thus, the preparation of fibers is the subject of the next section.

IV. Preparation of Fibers

Examples 178–239

A. Meltblown Fibers from Bench-Scale Apparatus

As a simple screening method, fibers were formed by means of a bench-scale apparatus having a single orifice in the die tip. The apparatus consisted of a cylindrical steel reservoir having a capacity of about 15 g. The reservoir was enclosed by an electrically heated steel jacket. The temperature of the reservoir was thermostatically controlled by means of a feedback thermocouple mounted in the body of the reservoir. The extrusion orifice had a diameter of 0.016 inch (0.41 mm) and a length of 0.060 inch (1.5 mm). A second thermocouple was mounted near the die tip. The exterior surface of the die tip was flush with the reservoir body. Composition extrusion was accomplished by means of a compressed air piston in the reservoir. The extruded filament was surrounded and attenuated by a cylindrical air stream exiting a circular 0.075-inch (1.9-mm) gap. Attenuating air pressures typically were of the order of 5–90 psig. The forming distance was approximately 10 inches (25 cm). The attenuated extruded filament was collected on the clear plastic film of an 8.5×11 inch (21.6×27.9 cm) loose leaf protector having a black paper insert.

In each case, the material extruded consisted of a simple mixture of a polymer and the desired additive(s) in the desired amount(s). The mixtures extruded (meltblown) are summarized in Table 22.

TABLE 22

Summary of Compositions Meltblown on Bench-Scale Apparatus

| Example | Polymer Code | Additive Code | Wt. Percent |
|---|---|---|---|
| 178 | PPA | A01 | 3 |
| 179 | PPC | A01 | 3 |
| 180 | PPA | A02 | 3 |
| 181 | PPC | A02 | 3 |
| 182 | PPA | A03 | 3 |
| 183 | PPC | A03 | 3 |
| 184 | PPA | A04 | 3 |
| 185 | PPC | A04 | 3 |
| 186 | PPA | A05 | 3 |
| 187 | PPC | A05 | 3 |
| 188 | PPA | A06 | 3 |
| 189 | PPC | A06 | 3 |
| 190 | PPA | A07 | 3 |
| 191 | PPC | A07 | 3 |
| 192 | PPA | A08 | 3 |
| 193 | PPC | A08 | 3 |
| 194 | PPA | A09 | 3 |
| 195 | PPC | A09 | 3 |
| 196 | PPA | A10 | 2 |
| 197 | PPA | A10 | 3 |
| 198 | PPC | A10 | 3 |
| 199 | PPA | A11 | 3 |
| 200 | PPA | A11 | 5 |
| 201 | PPB | A11 | 3 |
| 202 | PPB | A11 | 5 |
| 203 | PPA | A12 | 3 |
| 204 | PPC | A12 | 3 |
| 205 | PPA | A13 | 2 |
| 206 | PPA | A13 | 3 |
| 207 | PPC | A13 | 3 |
| 208 | PPA | A14 | 3 |
| 209 | PPC | A14 | 3 |
| 210 | PPA | A15 | 2 |
| 211 | PPA | A15 | 3 |
| 212 | PPC | A15 | 3 |
| 213 | PPA | A16 | 3 |
| 214 | PPC | A16 | 3 |
| 215 | PPA | A17 | 2 |
| 216 | PPC | A17 | 3 |
| 217 | PPA | A18 | 2 |
| 218 | PPA | A18 | 3 |
| 219 | PPC | A18 | 3 |
| 220 | PPA | A19 | 3 |
| 221 | PPC | A19 | 3 |
| 222 | PPA | A20 | 2 |
| 223 | PPA | A20 | 3 |
| 224 | PPB | A20 | 3 |
| 225 | PPC | A20 | 3 |
| 226 | PPA | A22 | 3 |
| 227 | PPC | A22 | 3 |
| 228 | PPA | A24 | 2 |
| 229 | PPA | A24 | 3 |
| 230 | PPB | A24 | 3 |
| 231 | PPC | A24 | 3 |
| 232 | PPA | B01 | 2 |
| 233 | PPA | B02 | 2 |
| 234 | PPA | B03 | 2 |
| 235 | PPA | B04 | 2 |
| 236 | PPA | B11 | 2 |
| 237 | PPA | B04 | 0.33 |
|  |  | B05 | 0.33 |
|  |  | C01 | 0.33 |
| 238 | PPA | B04 | 0.67 |
|  |  | B05 | 0.67 |
|  |  | C01 | 0.67 |
| 239 | PPA | B04 | 1 |
|  |  | B05 | 1 |
|  |  | C01 | 1 |

Meltblowing conditions for any given composition depended primarily on the polymer component. Consequently, standardized conditions were utilized for each of the three polymers as summarized in Table 23.

TABLE 23

Summary of Meltblowing Conditions Using the Bench-Scale Apparatus[a]

| Polymer Code | Die Temp., ° | Air Temp., ° |
|---|---|---|
| PPA | 260 | 228 |
| PPB | 249 | 249 |
| PPC | 240 | 230 |

[a]The conditions given are approximate only and typically may vary by as much as ± 30°.

The wettability of each web was estimated by placing a drop of water on a sample of the nonwoven material and measuring the time required for complete penetration of the water drop into the fabric (referred to hereinafter as "wetting time"). Each sample was tested with a minimum of five drops of water placed in five different locations. If all of the drops wet the web within three seconds, the web was considered to be immediately wettable (i.e., wettable). If the wetting times of the drops were greater than three seconds and equal to or less than 30 seconds, the web was considered to be slowly wettable. If wetting times were greater than 30 seconds, the web was considered to be nonwettable.

Of the webs obtained in Examples 178-239, inclusive, those from Examples 178-227, 232-234, and 237-239, inclusive, were immediately wettable, although in some cases wettability was dependent upon fiber diameter. Those from Examples 228-231, inclusive, 235, and 236 were nonwettable. It is seen from Table 16 that Examples 228-231 employed additive A24, Example 235 employed additive B04, and Example 236 employed additive B11. According to Table 1, additive A24 has a molecular weight of about 7,900. From Table 3, it is seen that additive B04 has a molecular weight of about 3,000 and additive B11 has a molecular weight of about 15,000. All three molecular weights are high enough to prevent the rapid segregation of the additive to the effective and/or interfacial surface region of the fibers. Consequently, the fibers were not wettable.

It should be noted, however, that webs made from a composition containing a mixture of additives having molecular weights equal to or greater than about 3,000, i.e., the webs of Examples 237-239, inclusive, were wettable, while webs made from a composition containing any one of the additives used in the mixture were not wettable (i.e., the web of Example 235). This illustrates the apparent synergistic effect which can result from combining additives, even though such additives individually do not segregate under similar melt-processing conditions above the subsurface of the fibers or films.

Some qualitative observations on web quality and wettability as a function of fiber diameter are appropriate at this point, at least for webs made with polymer PPA.

Web quality was based on visual inspection or inspection under a low-power optical microscope and was rated on a scale of from b 'to 4 as follows:

4—fibers having uniform diameters with no shot present;

3—fibers having a small amount of fiber diameter nonuniformity, with small amounts of shot present (fiber diameter nonuniformity refers to variations of fiber diameter, i.e., the presence of varying large and small fiber diameters);

2—moderate fiber nonuniformity and a moderate amount of shot present; and

1—substantial fiber nonuniformity and a large amount of shot present.

Fiber diameters also were estimated visually or under the microscope and were simply classed as small, medium, or large, As will be described in greater detail alter, fiber diameter is a function of attenuating air pressure—the higher the pressure, the smaller the fiber diameters.

A number of the webs obtained in Examples 178-239, inclusive, were evaluated for web quality and fiber diameter. The results of this evaluation and the wettabilities of the webs evaluated are summarized in Table 24.

TABLE 24

Summary of Evaluations of Web Quality and Fiber Diameters

| Additive | | Cloud | Primary | Web | |
|---|---|---|---|---|---|
| Code | MW | Point[a] | Air[b] | Rating | Wettability[c] |
| A06 | 678 | 2 | 25-90 | 4 | WS, WM, WL |
| A11 | 852 | 3 | 25-90 | 4 | WS, WM, WL |
| A13 | 852 | 2 | 25-90 | 4 | WS, WM, WL |
| A17 | 1130 | 45 | 27 | 1 | WL |
| A19 | 1200 | 40 | 30 | 1 | WL |
| A20 | 1450 | 0 | 26-90 | 4 | WS, WM, WL |
| A22 | NA[d] | 4 | 25-85 | 4 | WS, WM, WL |
| A23 | NA | 4 | 25-90 | 4 | WS, WM, WL |
| B01 | 600 | 10 | 30-90 | 4 | WS, WM, WL |
| B04 | 3000 | 0 | 30-80 | 4 | WL |
| B05 | 3000 | 1[e] | 25 | 1 | Nonwettable[f] |
| B07 | 5792 | 10 | 25-45 | 3 | WL |
| B08 | 5962 | 65 | 25 | 1 | Slowly Wett.[f] |
| B11 | 15,444 | 42 | 25 | 1 | Nonwettable[f] |
| C01 | 8000 | 42 | 25 | 2 | Nonwettable[f] |

[a]In degrees C.
[b]In psig.
[c]Code:
WS = small diameter fibers wettable;
WM = medium diameter fibers wettable; and
WL = large diameter fibers wettable.
[d]Not available.
[e]Insoluble.
[f]Only large fibers were produced.

The data in Table 24 substantiate the already-observed decrease in wettability associated with increasing additive molecular weight. In addition, however, the data suggest that there is a correlation between web quality and additive cloud point. That is, when the cloud point of the additive is above about 20° C., web quality declines significantly. Thus, the cloud point of additives employed to impart water wettability to the surface of fibers or films preferably will be no more than about 20° C. and most preferably no more than about 10° C.

Examples 240-261

In order to more fully understand the segregation phenomenon, three series of the bench-scale meltblowing experiments were repeated under somewhat more carefully controlled conditions. The first series employed either polymer PPA or PPB and additive levels of two percent by weight; the process and product details are summarized in Table 25. Fiber diameters were estimated from scanning electron photomicrographs taken by Surface Science Laboratories, Inc., Mountain View, Calif. The instrument employed was a Camscan Series 4 Scanning Electron Microscope. The accelerating voltage was 24 keV, the working distance was 20 mm, and the spot size was 5. The instrument was calibrated with 0.76-micron diameter National Bureau of Standards latex spheres. Each sample was gold coated (100-Å thickness) to increase conductivity under the electron beam.

TABLE 25

Summary of First Series of Additional Bench-Scale Meltblowing Experiments

| | Additive | | Air | Fiber |
|---|---|---|---|---|
| Example[a] | Code | MW | Press.[b] | Dia.[c] |
| 240 | B01 | 600 | 40 | 15 |
| 241 | B01 | 600 | 80 | 3 |
| 242 | B02 | 836 | 20 | 12 |
| 243 | B02 | 836 | 80 | 3 |
| 244 | B03 | 850 | 40 | 12 |
| 245 | B03 | 850 | 80 | 4 |
| 246 | A13 | 852 | 35 | 12 |
| 247 | A13 | 852 | 80 | 4 |
| 248 | B04 | 3000 | 25 | 12 |
| 249 | B04 | 3000 | 40 | 5 |
| 250[d] | B04 | 3000 | 12 | 20 |
| | B05 | 3000 | | |
| | C01 | 8000 | | |
| 251[d] | B04 | 3000 | 20 | 6 |
| | B05 | 3000 | | |
| | C01 | 8000 | | |
| 252[d] | B04 | 3000 | 25 | 5 |
| | B05 | 3000 | | |
| | C01 | 8000 | | |
| 253[d] | B04 | 3000 | 40 | 2-3 |
| | B05 | 3000 | | |
| | C01 | 8000 | | |

[a]Polymer PPA was employed in every case, except for Examples 250-253, inclusive, which utilized polymer PPB.
[b]In psig.
[c]In micrometers.
[d]The polymer contained a mixture of all three additives in equal concentrations; the total of all three additives still was two percent by weight.

In each case, a coherent web was obtained. Each web was subjected to ESCA analysis. Additionally, each web was subjected to bulk elemental analysis and the water drop test. The ESCA data and the results of the elemental analyses and water drop tests are summarized in Table 26.

TABLE 26

Summary of Analytical Data And Water Drop Test for Webs from Experiments 240-253, Inclusive

| Example | Additive MW | Fiber Dia.[a] | ESCA Si[b] | Bulk Si[c] | Wettability |
|---|---|---|---|---|---|
| 240 | 600 | 15 | 1.8 | 0.006 | Wettable |
| 241 | 600 | 3 | 2.0 | 0.007 | Wettable |
| 242 | 836 | 12 | 1.9 | 0.017 | Wettable |
| 243 | 836 | 3 | 1.5 | 0.18 | Wettable |
| 244 | 850 | 12 | 2.6 | 0.08 | Wettable |
| 245 | 850 | 4 | 1.7 | 0.009 | Wettable |
| 246 | 852 | 12 | 4.3 | 0.011 | Wettable |
| 247 | 852 | 4 | 4.5 | 0.011 | Wettable |
| 248 | 3000 | 12 | 13.0 | 0.017 | Nonwettable |
| 249 | 3000 | 5 | 6.3 | 0.016 | Nonwettable |
| 250 | $3-8 \times 10^{3d}$ | 20 | 8.5 | 0.010 | Wettable |
| 251 | $3-8 \times 10^{3d}$ | 6 | 5.8 | 0.010 | Slowly Wett. |
| 252 | $3-8 \times 10^{3d}$ | 5 | 5.9 | 0.010 | Slowly Wett. |
| 253 | $3-8 \times 10^{3d}$ | 2-3 | 4.8 | 0.010 | Slowly Wett. |

[a]In micrometers.
[b]Average concentration in atom-percent to a depth of approximately 100 Å.
[c]Average concentration in atom-percent throughout the bulk of the fibers.
[d]The polymer contained three aditives having molecular weights of 3,000, 3,000, and 8,000, respectively.

From Table 26, it is seen that only two webs were not wettable; both webs were made with additive B04 which has a molecular weight of about 3,000. Interestingly, the fibers of both webs had higher bulk silicon concentrations and higher surface silicon concentrations than any of the webs which were wettable. Indeed, the fibers of the web from Example 248 had from three to nine times as much silicon in the top 100-Å layer of the surface as the fibers of webs which were wettable. Notwithstanding such high concentrations, it is evident that there was insufficient additive in the effective surface to render the webs wettable. Thus, while the higher molecular weight additives will segregate to some extend, additive molecular weights of less than about 3,000 are required in order for additive to migrate to the interfacial surface or effective surface in concentrations sufficient to impart wettability to the fibers, at least for fibers having diameters in the 3–15 micrometer range.

In order to demonstrate the effect of fiber diameter on surface silicon concentration, a second series of bench-scale meltblowing experiments was carried out. In this series, the polymer was PPB and the additive was A10 at a level of two percent by weight (the additive molecular weight is 794—see Table 1). ESCA analyses were carried out on the webs, all of which were wettable. The results are summarized in Table 27.

TABLE 27

Summary of Second Series of Additional Bench-Scale Meltblowing Experiments

| Example | Air Press.$^a$ | Fiber Dia.$^b$ | ESCA Data$^c$ | |
|---|---|---|---|---|
| | | | % C | % Si |
| 254 | 40 | 6 | 84 | 4.7 |
| 255 | 50 | 4 | 87 | 4.1 |
| 256 | 60 | 2 | 88 | 3.9 |

$^b$In micrometers, estimated from scanning electron photomicrographs as already described.
$^c$Average concentration in atom-percent to a depth of approximately 100 Å; the bulk silicon concentration as determined by elemental analysis was 0.01 atom-percent.

From the discussion earlier regarding the factors influencing the segregation of the additive, it is apparent that there are two competing factors in the segregation of additive during fiber formation. First, as the diameter of the fiber is diminished, the distance to the surface also is diminished, thereby contributing to the higher additive concentrations in the surface region. Second, as the diameter of the fiber is diminished, the time the fiber remains in a molten state also is diminished, thereby shortening the time during which the additive can migrate toward the surface. From the data in Table 27, it is evident that the second factor was controlling since the additive concentration was reduced as the fiber diameter decreased.

As already pointed out, the higher molecular weight additives segregate toward the surface of the fiber or film, but typically do not reach either the interfacial surface or the effective surface. In cases where the additive has segregated to the subsurface and is sufficiently close to the effective surface, the additive can be "coaxed" to the effective surface by the application of relatively mild heating conditions. This phenomenon is illustrated by a third series of bench-scale meltblowing experiments.

The third series of experiments involved in incorporation of two weight percent of an additive in PPA polymer essentially as described in Examples 178–239, inclusive. As ESCA and elemental analysis was obtained for each web. The wettability of each web also was estimated by the water drop test. A sample of each web then was heated in an oven at 120 degrees for 20 seconds. An ESCA analysis was obtained on the heated web and its wettability estimated as before. The results are summarized in Tables 28 and 29.

TABLE 28

Summary of Third Series of Additional Bench-Scale Meltblowing Experiments

| Example | Additive Code | MW | Bulk % Si$^a$ |
|---|---|---|---|
| 257 | A15 | 1023 | 0.005 |
| 258 | A18 | 1200 | 0.014 |
| 259 | A20 | 1450 | 0.014 |
| 260 | A23 | NA$^b$ | 0.008 |
| 261 | B11 | 15,444 | 0.006 |

$^a$Average concentration in atom-percent throughout the bulk of the fibers.
$^b$Not available.

TABLE 29

Summary of ESCA Data and Wettability Testing for Third Series of Bench-Scale Meltblowing Experiments Before and After Heating the Webs

| | Before Heating | | After Heating | |
|---|---|---|---|---|
| Example | % Si$^a$ | Wettability | % Si$^a$ | Wettability |
| 257 | 3.2 | Nonwettable | 5.8 | Slowly Wett. |
| 258 | 1.9 | Nonwettable | 2.7 | Wettable |
| 259 | 6.9 | Wettable | 7.4 | Wettable |
| 260 | 4.3 | Nonwettable | 3.3 | Nonwettable |
| 261 | 4.7 | Nonwettable | 5.3 | Nonwettable |

$^a$Average concentration in atom-percent to a depth of approximately 100 Å.

While the heat treatment did not convert every nonwettable web into a wettable one, the procedure was successful for the two lowest molecular weight additives. Whether or not such treatment can be used depends, at least in part, on whether or not the additive has segregated to the subsurface sufficiently close to the effective surface to permit a gentle heat treatment to move the material into the effective surface region. Such segregation in turn is in part dependent upon the diameter of the fibers, i.e., the time the fibers remain in a molten state. Thus, the choice of additive and heat treatment conditions is, of necessity, somewhat empirical.

The ability of additive to be moved from the subsurface to either the effective surface or the interfacial surface, or both, expands the types of products based on nonwoven webs prepared in accordance with the present invention. A few examples in the area of household and industrial wipes will serve by way of illustration:

(1) a wipe consisting of a single polyolefin nonwoven web prepared in accordance with the present invention, in which additive is present in either or both of the effective surfaces and the interfacial surfaces of the fibers—the wipe is hydrophilic or water wettable and is suited for washing or cleaning tasks using aqueous cleaning solutions;

(2) a wipe consisting of a single polyolefin nonwoven web prepared in accordance with the present invention, in which additive is present in the subsurface of the fibers—the web is hydrophobic or oleophilic and is suited for cleaning oily surfaces, but on washing the wipe is converted to a hydrophilic wipe because the heat of the washing or drying environment will cause additive to migrate from the fiber subsurface to either or both of the fiber effective surface and interfacial surface, which conversion aids in the removal of oily residues from the wipe; and (3) a wipe consisting of two polyolefin nonwoven layers, one prepared from virgin polymer and the other consisting of a web as described in either (1) or (2) above—in the first instance, the wipe will be effective for both water-soluble or water dispersible substances and oily substances, depending on which layer is used as the wiping layer, and in the second instance, the wipe can be converted to a wipe of the first instance by laundering.

B. Meltblown Fibers from Pilot-Scale Apparatus

Examples 262-297

Since the above bench-scale meltblowing experiments in general were successful, meltblowing trials were conducted on a pilot-scale meltblowing apparatus essentially as described in U.S. Pat. No. 4,663,220, which is incorporated herein by reference. Briefly, such meltblowing was accomplished by extruding a composition (or a simple mixture) through a 0.75-inch (19-mm) diameter Brabender extruder and then through a meltblowing die having nine extrusion capillaries per linear inch (approximately 3.5 capillaries per linear cm) of die tip. Each capillary had a diameter of about 0.0145 inch (about 0.37 mm) and a length of about 0.113 inch (about 2.9 mm). The process variables in general were as follows:

polymer extrusion rate, 2.5-3.5 g per capillary per minute;
polymer extrusion temperature, 250°-300°, depending upon the polymer employed;
extrusion pressure, 490-510 psig;
die tip temperature, 270°-275°;
attenuating air temperature, 304°-310°;
attenuating air pressure, 8-11 psig; and
forming distance, 20-40 cm.

The collecting arrangement consisted of a rotating 15.2-cm wide drum having a diameter of 76.2 cm. The surface of the drum was a screen.

The polymer and additive typically were mixed by one of several methods before introducing the mixture to the feed hopper of the extruder. In the first (method A), a standard portable cement mixer was charged with 50 pounds of the polymer in pellet form. The mixer then was started and charged with the desired amount of additive. Mixing was allowed to continue for 20 minutes, after which time the mixture was removed from the mixer and stored in plastic-lined boxes. In a variation of that method, the additive was used in an amount higher than that intended for melt-processing to give a stock mixture. The stock mixture then was mixed in a similar fashion with additional polymer in a ratio calculated to give the desired final additive concentration (method B). In the third (method C), a metered stream of additive was pumped into the feed hopper about 15 cm above the feed screws as polymer pellets flowed downward by gravity into the screws. All three methods worked equally well, although method C was used with only one additive.

In each case, a coherent web was obtained which had a basis weight in the range of from about 20 to about 50 g/m². Wettability was estimated by means of the water drop test. The trials are summarized in Table 30, along with the results of the water drop test.

TABLE 30

| Summary of Pilot-Scale Meltblowing Trials | | | | |
|---|---|---|---|---|
| | Polymer | Additive | | |
| Example | Code | Code | Wt. % | Wettability |
| 262 | PPA | A11 | 2 | Wettable |
| 263 | PPA | A11 | 3 | Wettable |
| 264 | PPA | A11 | 5 | Wettable |
| 265 | PPB | A11 | 2 | Wettable |
| 266 | PPB | A11 | 3 | Wettable |

TABLE 30-continued

| Summary of Pilot-Scale Meltblowing Trials | | | | |
|---|---|---|---|---|
| | Polymer | Additive | | |
| Example | Code | Code | Wt. % | Wettability |
| 267 | PPB | A11 | 5 | Wettable |
| 268 | PPA | A18 | 1 | Wettable |
| 269 | PPA | A18 | 3 | Wettable |
| 270 | PPA | A18 | 5 | Wettable |
| 271 | PPB | A18 | 1 | Wettable |
| 272 | PPB | A18 | 3 | Wettable |
| 273 | PPB | A18 | 5 | Wettable |
| 274 | PPA | A21 | 1 | Wettable |
| 275 | PPA | A21 | 3 | Wettable |
| 276 | PPA | A21 | 5 | Wettable |
| 277 | PPC | A21 | 1 | Wettable |
| 278 | PPC | A21 | 3 | Wettable |
| 279 | PPC | A21 | 5 | Wettable |
| 280 | PPA | B01 | 1 | Wettable |
| 281 | PPA | B01 | 3 | Wettable |
| 282 | PPA | B01 | 5 | Wettable |
| 283 | PPB | B01 | 1 | Wettable |
| 284 | PPB | B01 | 3 | Wettable |
| 285 | PPB | B01 | 5 | Wettable |
| 286 | PPC | B01 | 1 | Wettable |
| 287 | PPC | B01 | 3 | Wettable |
| 288 | PPC | B01 | 5 | Wettable |
| 289 | PPA | B04 | 1 | Nonwettable |
| 290 | PPA | B04 | 3 | Nonwettable |
| 291 | PPA | B04 | 5 | Nonwettable |
| 292 | PPA | B05 | 1 | Nonwettable |
| 293 | PPA | B05 | 3 | Nonwettable |
| 294 | PPA | B05 | 5 | Nonwettable |
| 295 | PPA | C01 | 1 | Nonwettable |
| 296 | PPA | C01 | 3 | Nonwettable |
| 297 | PPA | C01 | 5 | Nonwettable |

The results obtained are consistent with the bench-scale meltblowing experiments. Single additives having molecular weights of the order of 3,000 or higher do not segregate to the interfacial surface or effective surface when fiber diameters are relatively small, as they are in typical meltblowing processes.

C. Spunbonded Fibers from Pilot-Scale Apparatus

Examples 298-365

Spunbonded trials were conducted on a pilot-scale apparatus essentially as described in U.S. Pat. No. 4,360,563, which is incorporated herein by reference.

The polymer and additive typically were mixed by one of the methods described above with repect to Examples 262-297, inclusive.

In each case, a web was obtained which had a basis weight in the range of from about 14 to about 60 g/m². In some cases, webs of different basis weights were made during a trial by changing the velocity of the forming wire. Typical basis weights thus prepared were 14, 19, 36, 47, and 59 g/m². Wettability was estimated by means of the water drop test.

Unlike the meltblown trials, however, it was discovered that when the additive level was greater than 1 percent by weight, there was no web integrity; that is, the web simply fell apart upon attempting to remove it from the forming wire, even when excellent fiber formation was obtained. The problem was overcome by running the web under a heated compaction roll before removing it from the forming wire. Thus, all of the spunbonded examples in which additive levels were greater than 1 percent by weight utilized a heated compaction roll. While a compaction roll temperature of about 66° was employed, lower or higher temperatures can be used.

The trials are summarized in Table 31, along with the results of the water drop test; because wettability was independent of web basis weight, the latter is not included in the table.

TABLE 31

Summary of Pilot-Scale Spunbonding Trials

| Example | Polymer Code | Additive Code | Wt. % | Wettability |
|---|---|---|---|---|
| 298 | PPA | A05 | 1 | Wettable |
| 299 | PPA | A05 | 3 | Wettable |
| 300 | PPC | A05 | 1 | Wettable |
| 301 | PPC | A05 | 3 | Wettable |
| 302 | PPD | A05 | 1 | Wettable |
| 303 | PPD | A05 | 3 | Wettable |
| 304 | PPA | A08 | 0.75 | Wettable |
| 305 | PPA | A08 | 1 | Wettable |
| 306 | PPA | A08 | 3 | Wettable |
| 307 | PPD | A08 | 0.75 | Wettable |
| 308 | PPD | A08 | 1 | Wettable |
| 309 | PPD | A08 | 3 | Wettable |
| 310 | PPE | A08 | 1 | Wettable |
| 311 | PPE | A08 | 3 | Wettable |
| 312 | PPA | A10 | 0.5 | Slowly Wett. |
| 313 | PPA | A10 | 0.75 | Wettable |
| 314 | PPA | A10 | 1 | Wettable |
| 315 | PPA | A10 | 1.5 | Wettable |
| 316 | PPA | A10 | 2 | Wettable |
| 317 | PPA | A10 | 3 | Wettable |
| 318 | PPE | A10 | 0.5 | Slowly Wett. |
| 319 | PPE | A10 | 0.75 | Wettable |
| 320 | PPE | A10 | 1 | Wettable |
| 321 | PPE | A10 | 1.5 | Wettable |
| 322 | PPE | A10 | 2 | Wettable |
| 323 | PPE | A10 | 3 | Wettable |
| 324 | PPE | A11 | 0.5 | Slowly Wett. |
| 325 | PPE | A11 | 0.75 | Wettable |
| 326 | PPE | A11 | 1 | Wettable |
| 327 | PPE | A11 | 1.5 | Wettable |
| 328 | PPA | A11 | 2 | Wettable |
| 329 | PPA | A11 | 3 | Wettable |
| 330 | PPD | A11 | 0.5 | Slowly Wett. |
| 331 | PPD | A11 | 0.75 | Wettable |
| 332 | PPD | A11 | 1 | Wettable |
| 333 | PPD | A11 | 1.5 | Wettable |
| 334 | PPD | A11 | 2 | Wettable |
| 335 | PPD | A11 | 3 | Wettable |
| 336 | PPE | A11 | 0.5 | Slowly Wett. |
| 337 | PPE | A11 | 0.75 | Wettable |
| 338 | PPE | A11 | 1 | Wettable |
| 339 | PPE | A11 | 1.5 | Wettable |
| 340 | PPE | A11 | 2 | Wettable |
| 341 | PPE | A11 | 3 | Wettable |
| 342 | PPA | A14 | 1 | Wettable |
| 343 | PPA | A14 | 3 | Wettable |
| 344 | PPD | A14 | 1 | Wettable |
| 345 | PPD | A14 | 3 | Wettable |
| 346 | PPA | B01 | 1 | Wettable |
| 347 | PPA | B01 | 3 | Wettable |
| 348 | PPA | B01 | 5 | Wettable |
| 349 | PPD | B01 | 0.5 | Wettable |
| 350 | PPD | B01 | 1 | Wettable |
| 351 | PPD | B01 | 2 | Wettable |
| 352 | PPD | B01 | 3 | Wettable |
| 353 | PPD | B01 | 5 | Wettable |
| 354 | PPA | B04 | 1 | Wettable |
| 355 | PPA | B04 | 3 | Wettable |
| 356 | PPA | B04 | 5 | Wettable |
| 357 | PPA | B05 | 1 | Wettable |
| 358 | PPA | B05 | 3 | Wettable |
| 359 | PPA | B05 | 5 | Wettable |
| 360 | PPA | C01 | 1 | Nonwettable |
| 361 | PPA | C01 | 3 | Nonwettable |
| 362 | PPA | C01 | 5 | Nonwettable |
| 363[a] | PPA | B04 | 0.33 | Wettable |
|  |  | B05 | 0.33 |  |
|  |  | C01 | 0.33 |  |
| 364[a] | PPA | B04 | 0.67 | Wettable |
|  |  | B05 | 0.67 |  |
|  |  | C01 | 0.67 |  |
| 365[b] | PPA | B04 | 1 | Wettable |
|  |  | B05 | 1 |  |
|  |  | C01 | 1 |  |

TABLE 31-continued

Summary of Pilot-Scale Spunbonding Trials

| Example | Polymer Code | Additive Code | Wt. % | Wettability |
|---|---|---|---|---|

[a] The composition also contained 2.5 percent by weight titanium dioxide.
[b] The composition also contained 2.0 percent by weight titanium dioxide.

Because spunbonded fibers typically have larger diameters on the average than meltblown fibers, the spunbonded webs were wettable or slowly wettable with additives having molecular weights up to about 3,000. However, the use of an additive having a molecular weight of about 8,000 did not produce a wettable web.

In order to further investigate the ability of a gentle post-formation heat treatment to bring additive to the effective surface and/or interfacial surface, ESCA analyses were carried out on three of the spunbonded webs. The webs then were heated at 110 degrees for 1 minute in a laboratory oven and the heated webs were subjected to ESCA analyses. The results of the ESCA analyses before and after heating are summarized in Table 32.

TABLE 32

Summary of ESCA Analyses Before and After Heating

| | ESCA Analyses Before and After Heating[a] | | | | | | |
|---|---|---|---|---|---|---|---|
| | Before Heating | | | After Heating | | | % |
| Example | % C | % O | % Si | % C | % O | % Si | Inc.[b] |
| 325 | 95 | 3.2 | 1.6 | 91 | 6.6 | 2.8 | 75 |
| 326 | 95 | 3.9 | 1.6 | 79 | 15 | 6.5 | 306 |
| 327 | 84 | 11 | 5.0 | 76 | 17 | 7.4 | 48 |

[a] In atom percent.
[b] Percent silicon increase in first 100 Å of surface.

The data in Table 32 clearly show the remarkable increase in silicon concentration within the first 100 Å of the surface upon exposing a web to a mild heat treatment, especially at an additive level of 1 percent by weight.

Because spunbonded webs commonly are employed as liners in disposable diapers, the mild heat treatment phenomenon was investigated by two different methods in conjunction with a simple diaper run-off test. The diaper run-off test involved removing the linear from a standard KIMBEE diaper. The linerless diaper was mounted on a plate which was inclined at a 45° angle, the back edge of the diaper being at the top of the plate. The test fabric was layed over the diaper. A reservoir containing 100 ml of 0.85 percent (weight per volume) saline (cat. no. SS-442-10, Fisher Scientific, Pittsburgh, Pa.) at 37° was located at the top of the plane 2 inches (5.1 cm) above the uppermost edge of the diaper's absorbent pad. The saline then was allowed to run out of the reservoir in a steady stream. Fluid which was not retained by the diaper was collected and measured, the volume in ml being the run-off value.

In the first method, samples of a spunbonded nonwoven web made from a composition of the present invention and having a basis weight of 27 g/m² were heated in an oven at two different temperatures. Run-off measurements were made on samples which had not been heat treated and those which had. In every case, the additive was A11 and the polymer was PPE. The results are summarized in Table 33.

TABLE 33

Summary of Results of Run-Off Test
After First Heat Treatment Method

| Web Example | Add. Level[a] | Oven Temp., ° | Heating Time | Run-Off Test, ml |
|---|---|---|---|---|
| 324 | 0.5 | — | — | 100[b] |
| | 0.5 | 80 | 3 min. | 20–30 |
| | 0.5 | 110 | 30 sec. | 30–40 |
| 325 | 0.75 | — | — | 70–80[b] |
| | 0.75 | 80 | 3 min. | 0–1 |
| | 0.75 | 110 | 30 sec. | 40–50 |
| 326 | 1 | — | — | 20–30[b] |
| | 1 | 80 | 3 min. | 0 |
| | 1 | 110 | 30 sec. | 0 |

[a] In weight percent.
[b] Control.

The efficacy of the heat treatment in each case is readily apparent. It appears that 80° for 3 minutes is more effective than 110° for 30 seconds, at least for the webs having the two lowest concentrations of additive. Either temperature treatment, however, converts the web containing 1 percent by weight of additive into a highly wettable, highly efficient transfer layer.

In the second method, samples in continuous roll form of the same webs used in the first method were passed over two steam cans in series which were heated by steam at a pressure of 5 psig. The surfaces of the cans were at about 85°. Each sample was passed over the cans at two different line speeds, after which the run-off test was performed. The results are summarized in Table 34.

TABLE 34

Summary of Results of Run-Off Test
After Second Heat Treatment Method

| Web Example | Add. Level[a] | Line Speed, m/min | Run-Off Test, ml |
|---|---|---|---|
| 324 | 0.5 | — | 100[b] |
| | 0.5 | 9 | 80–90 |
| | 0.5 | 4.5 | 80–90 |
| 325 | 0.75 | — | 70–80[b] |
| | 0.75 | 9 | 50 |
| | 0.75 | 4.5 | 50 |
| 326 | 1 | — | 20–30[b] |
| | 1 | 9 | 5–10 |
| | 1 | 4.5 | 0–5 |

[a] In weight percent.
[b] Control.

The results from the second method were similar to those of the first method in that the concentration of additive leading to the most efficient transfer layer was 1 percent by weight; the slower line speed gave slightly better results at that concentration.

Figure 9:
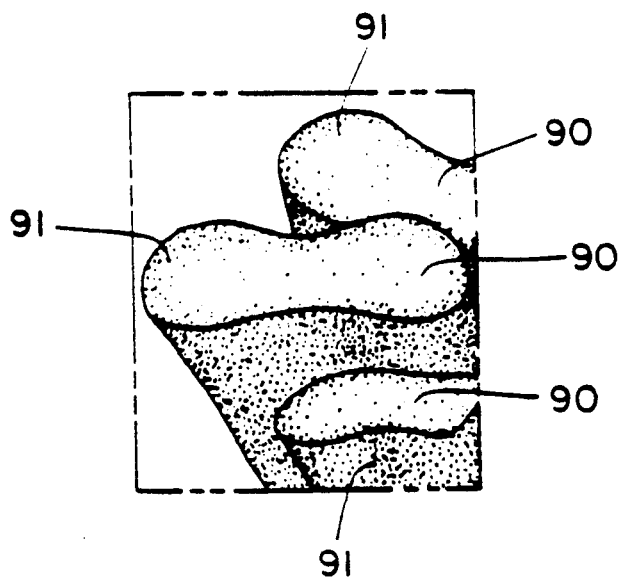
FIG. 9 is a diagrammatic representation of a scanning electron micrograph, using a silicon x-ray probe, of a section of the spunbonded nonwoven web of Example 364 prepared from a composition of the present invention, in which the additive was a silicon-containing compound.

Because of the success with the Si-SEM procedure with a melt-pressed film, a similar effort was carried out with spunbonded fibers prepared from a composition containing a mixture of additives in polymer PPA, i.e., Example 365. In this case, a bundle of fibers was collected before they reached the forming wire. The bundle was cut and inserted into a small plastic tube about 19 mm long and having an inside diameter of about 3 mm, thereby packing the tube with fibers. The packed tubing was placed in liquid nitrogen, removed, and cut with a razor blade. The sample was placed on the SEM mount and sputtered with carbon before carrying out the analysis. A diagrammatic representation of the results of the analysis is shown by FIG. 9. In FIG. 9, the fibers 50 are bilobal in cross-section. As with the film analysis, each of dots 51 represents the presence of silicon atoms.

It is clear that the additives included in the composition from which the fibers of Example 365 were prepared have segregated preferentially to the surface region of the film. While the core region is not as devoid of silicon as was the core region of the film, there clearly is a lower concentration of the additives in the core region than in the area at or near the surfaces of the fibers. This result was expected, however, because of the relatively rapid formation of the fibers as compared to the film formation time. That is, the fibers remained in a molten state for a time which was much shorter than the time the film remained in a molten state. The fact that the additives segregated to the surfaces of the fibers in such a short time is, as already pointed out, a result of the influence of shear during the extrusion process.

Two samples of fibers from the spunbonded trials were submitted for analysis by RBS. The results are summarized in Table 35.

TABLE 35

Summary of RBS Analyses on Spunbonded Fibers

| Example | Depth, Å | Atomic Concentration, Atom % | | | |
|---|---|---|---|---|---|
| | | C | O | Si | Ti |
| 329 | 0–1000 | 30 | 0.7 | 0.28 | 0.01[a] |
| | 1000–3000 | 30 | 0.2 | 0.06 | 0.02 |
| | >3000 | 30 | 0.2 | 0.03 | 0.03 |
| 329[b] | 0–1000 | 29 | 0.3 | 0.13 | 0.01[a] |
| | 1000–2000 | 29 | 0.1 | 0.02 | 0.02 |
| | >2000 | 30 | 0.1 | 0.02 | 0.02 |
| 364 | 0–250 | 28 | 3.6 | 1.94 | 0.02 |
| | 250–900 | 28 | 2.2 | 0.90 | 0.02 |
| | 900–1600 | 29 | 1.5 | 0.45 | 0.05 |
| | 1600–2900 | 29 | 1.0 | 0.37 | 0.05 |
| | 2900–4900 | 29 | 0.8 | 0.26 | 0.05 |
| | >4900 | 29 | 0.8 | 0.12 | 0.05 |

[a] This concentration was at or near the detection limit; the actual concentration may be considerably lower.
[b] A second analysis was carried out on the same sample.

From the data for the two analyses on the same sample, it appears that the RBS procedure causes some loss of additives as evidenced by the decreased silicon concentration values. Thus, it is probable that the concentration values are lower than the actual concentrations. Nevertheless, the procedure is helpful because it gives at least a qualitative view of the segregation of the additives in the surface region and the core region adjacent thereto.

The RBS data from Table 35 for the webs of Examples 329 and 364 were plotted as already described. The plots for the two analyses of the web of Example 329 are shown as FIGS. 10A and 10B. The plot for the analysis of the web of Example 364 is shown as FIG. 11.

Figure 11:
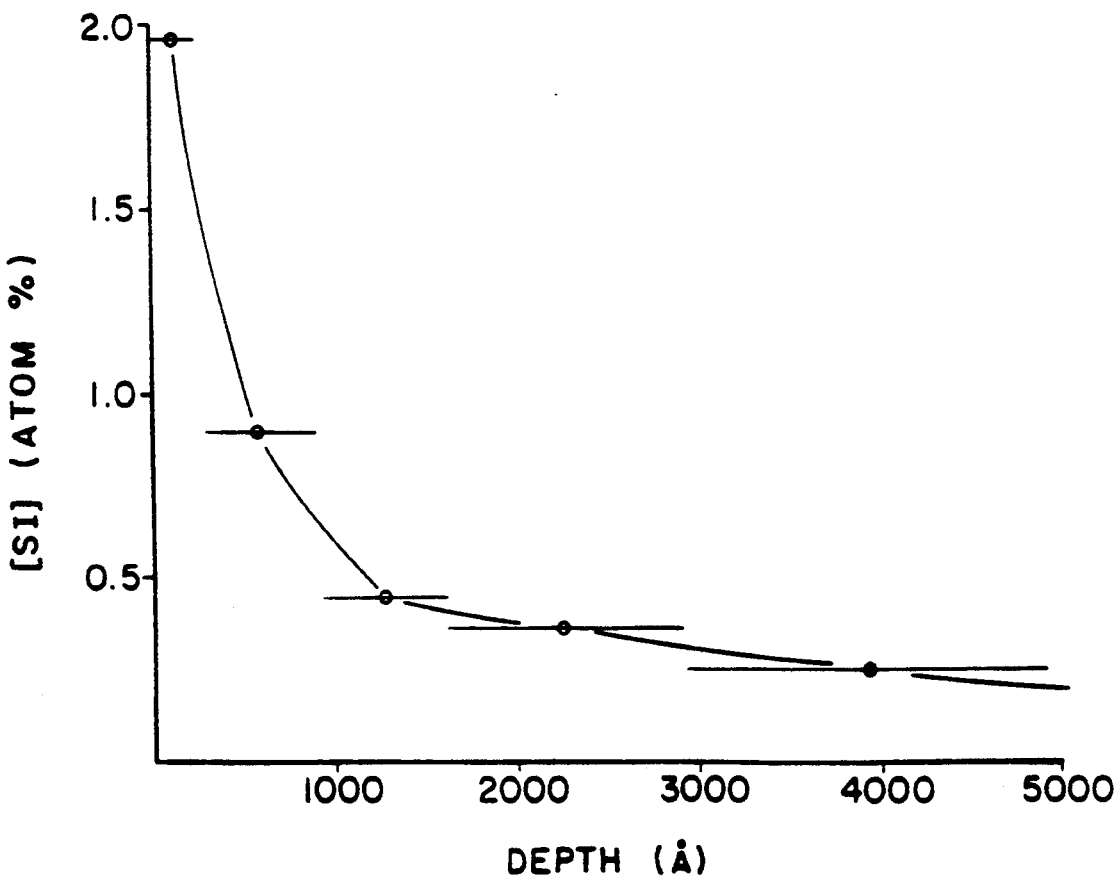
FIGS. 10 and 11 are plots of silicon concentrations in atom percent versus depth in Å below the interfacial surface for the fibers of two spunbonded nonwoven webs made in accordance with the present invention, i.e., Examples 328 and 363, in which the additive was a silicon-containing compound, the data for the plots having been obtained by Rutherford back scattering spectrometry.
Figure 10A:
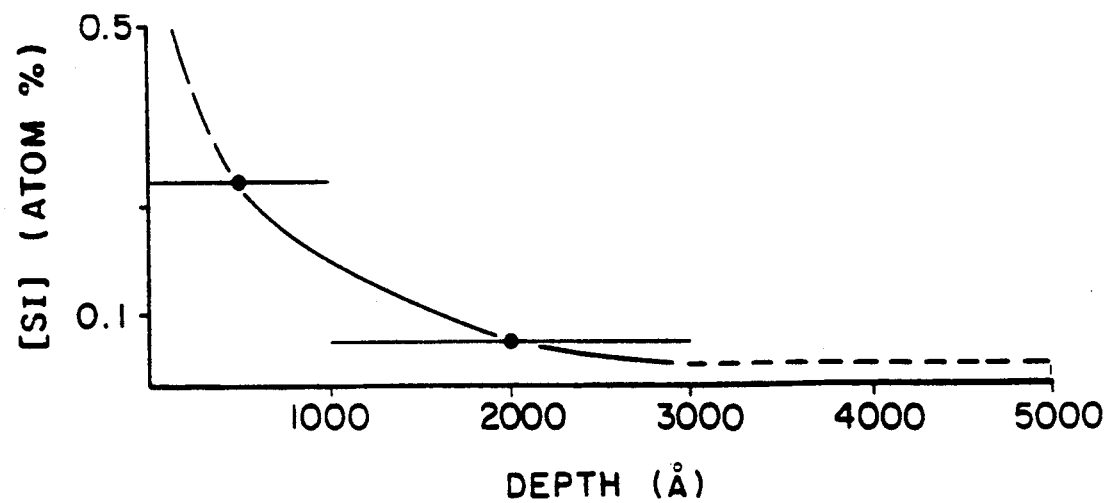
Figure 10B:
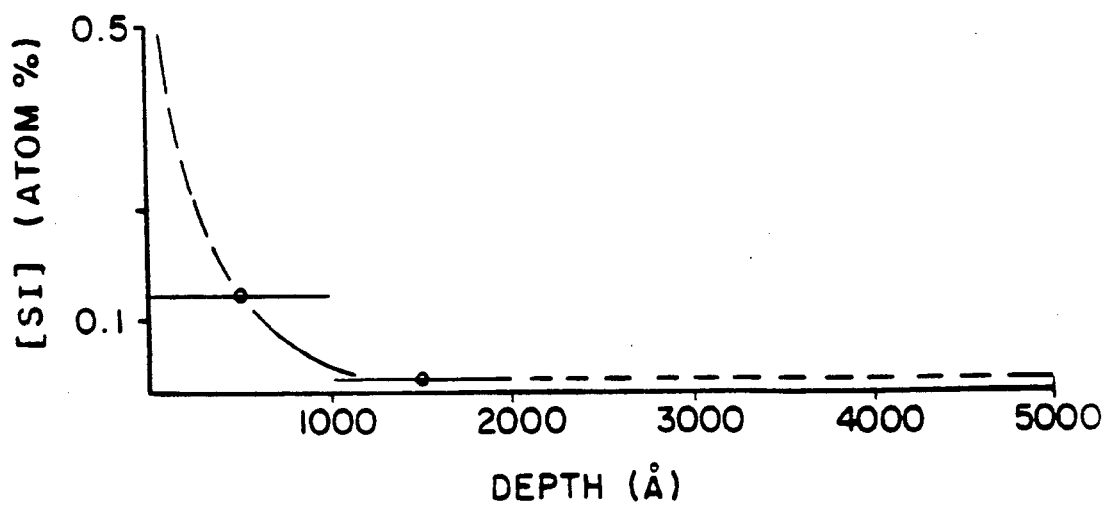

The plots are similar to that for the RBS analysis of the film of Example 173. FIGS. 8 and 10A are especially similar, although in the latter the concentration of silicon diminishes to the minimum concentration at around 2,000 Å, rather than at around 1,000 Å. In FIG. 11, it is seen that the silicon concentration diminishes more slowly with depth, although all of the plots resulted in curves having similar shapes.

The webs from Examples 329 and 364 also were submitted for ESCA and bulk elemental analyses. The results of these analyses are shown in Table 36.

TABLE 36

Summary of ESCA Data and Elemental Analyses for the Webs of Example 329 and 364

| | ESCA Data | | | Bulk Elemental Anal. | | |
|---|---|---|---|---|---|---|
| Example | % C | % O | % Si | % C | % H | % Si |
| 329 | 77 | 17 | 6.6 | 83.84 | 13.23 | 0.35 |
| 364 | 62 | 27 | 11 | 82.23 | 13.40 | 0.89 |

Examples 366–439

A number of larger-scale meltblowing runs were carried out on a coforming apparatus of the type described described in U.S. Pat. Nos. 4,100,432 and 4,663,220, the latter patent having been identified and incorporated herein by reference in regard to Examples 262–297, inclusive; the former patent also is incorporated herein by reference.

Meltblowing was accomplished by extruding the composition from a 1.5-inch (3.75-cm) Johnson extruder and through a meltblowing die having 15 extrusion capillaries per linear inch (about 5.9 extrusion capillaries per linear cm) of die tip. Each capillary had a diameter of about 0.018 inch (about 0.46 cm) and a length of about 0.14 inch (about 3.6 mm). The composition was extruded through the capillaries at a rate of about 0.5 g per capillary per minute at a temperature of about 184°. The extrusion pressure exerted on the composition in the die tip was in the range of from about 180 to about 200 psig. The composition viscosity in the die tip under these conditions was about 500 poise. The die tip configuration was adjusted to have a positive perpendicular die tip distance of about 0.01 inch (about 0.25 mm). The air gaps of the two attenuating air passageways were adjusted to be about 0.067 inch (about 1.7 mm). forming air for meltblowing the composition was supplied to the air passageways at a temperature of about 209° and a pressure of about 2 psig. The fibers thus formed were deposited on a forming screen drum which was approximately 18 inches (46 cm) below and 20 inches (51 cm) back from the die tip.

The more significant process variable generally were as follows:
 barrel temperature, 280°–300°;
 die temperature 285°–316°;
 melt temperature in die, 275°–316°;
 barrel pressure, 220–570 psig;
 die pressure, 55–130 psig;
 primary air temperature, 235°–349°;
 primary air pressure, 3–4.5 psig;
 throughput, 7–360 g per cam of die width per hour;
 forming distance, 36 cm; and
 basis weight, 27–85 g/m², wire the more typical basis weights being 27, 51, and/or 85 g/m².

The compositions which were meltblown were prepared by melt-blending polymer and additive(s) as described in Examples 50–130, inclusive. Coherent webs were formed in each case. As with previous trials, wettability of the formed webs was estimated by the water drop test as appropriate. The compositions meltblown and the results of the water drop test are summarized in Table 37.

TABLE 37

Summary of Meltblowing Trials on Pilot-Scale Coforming Apparatus

| Example | Comp. Code | Polymer Code | Additive(s) Code(s) | Wt. % | Wettability |
|---|---|---|---|---|---|
| 366 | PP28-1 | PPA | A21 | 1 | Wettable |
| 367 | PP29-1 | PPA | A21 | 3 | Wettable |
| 368 | PP30-1 | PPA | A21 | 5 | Wettable |
| 369 | PP31-1 | PPA | A21 | 12 | Wettable |
| 370 | PE18-1 | PEA | A21 | 1 | Wettable |
| 371 | PE19-1 | PEA | A21 | 3 | Wettable |
| 372 | PE20-1 | PEA | A21 | 5 | Wettable |
| 373 | PP32-1 | PPA | B01 | 3 | Wettable |
| 374 | PP33-1 | PPA | B01 | 5 | Wettable |
| 375 | PP34-1 | PPB | B01 | 3 | Wettable |
| 376 | PP35-1 | PPB | B01 | 5 | Wettable |
| 377 | PP36-1 | PPC | B01 | 3 | Wettable |
| 378 | PP37-1 | PPC | B01 | 5 | Wettable |
| 379 | PE21-1 | PEA | B01 | 3 | Wettable |
| 380 | PE22-1 | PEA | B01 | 5 | Wettable |
| 381 | PP38-1 | PPA | B02 | 3 | Wettable |
| 382 | PP39-1 | PPA | B02 | 5 | Wettable |
| 383 | PP40-1 | PPC | B02 | 3 | Wettable |
| 384 | PP41-1 | PPC | B02 | 5 | Wettable |
| 385 | PP42-1 | PPA | B03 | 3 | Wettable |
| 386 | PP43-1 | PPA | B03 | 5 | Wettable |
| 387 | PP44-1 | PPC | B03 | 3 | Wettable |
| 388 | PP45-1 | PPC | B03 | 5 | Wettable |
| 389 | PP46-1 | PPA | B04 | 3 | Nonwettable |
| 390 | PP47-1 | PPA | B04 | 5 | Nonwettable |
| 391 | PE23-1 | PEA | B04 | 3 | Nonwettable |
| 392 | PE24-1 | PEA | B04 | 5 | Nonwettable |
| 393 | PP48-1 | PPA | B05 | 3 | Nonwettable |
| 394 | PP49-1 | PPA | B05 | 5 | Nonwettable |
| 395 | PE25-1 | PEA | B05 | 3 | Nonwettable |
| 396 | PE26-1 | PEA | B05 | 5 | Nonwettable |
| 397 | PP50-1 | PPA | B06 | 3 | Nonwettable |
| 398 | PP51-1 | PPA | B06 | 5 | Nonwettable |
| 399 | PP52-1 | PPC | B06 | 3 | Nonwettable |
| 400 | PP53-1 | PPC | B06 | 5 | Nonwettable |
| 401 | PP54-1 | PPA | B07 | 3 | Nonwettable |
| 402 | PP55-1 | PPA | B07 | 5 | Nonwettable |
| 403 | PP56-1 | PPC | B07 | 3 | Nonwettable |
| 404 | PP57-1 | PPC | B07 | 5 | Nonwettable |
| 405 | PP58-1 | PPA | B08 | 3 | Nonwettable |
| 406 | PP59-1 | PPA | B08 | 5 | Nonwettable |
| 407 | PP60-1 | PPC | B08 | 3 | Nonwettable |
| 408 | PP61-1 | PPC | B08 | 5 | Nonwettable |
| 409 | PP62-1 | PPA | B09 | 2 | Nonwettable |
| 410 | PP63-1 | PPA | B09 | 3 | Nonwettable |
| 411 | PP64-1 | PPA | B09 | 5 | Nonwettable |
| 412 | PP65-1 | PPC | B09 | 3 | Nonwettable |
| 413 | PP66-1 | PPC | B09 | 5 | Nonwettable |
| 414 | PP67-1 | PPA | B10 | 3 | Nonwettable |
| 415 | PP68-1 | PPA | B10 | 5 | Nonwettable |
| 416 | PP69-1 | PPC | B10 | 3 | Nonwettable |
| 417 | PP70-1 | PPC | B10 | 5 | Nonwettable |
| 418 | PP71-1 | PPA | B11 | 3 | Nonwettable |
| 419 | PP72-1 | PPA | B11 | 5 | Nonwettable |
| 420 | PP73-1 | PPC | B11 | 3 | Nonwettable |
| 421 | PP74-1 | PPC | B11 | 5 | Nonwettable |
| 422 | PP75-1 | PPA | C01 | 1 | Nonwettable |
| 423 | PP76-1 | PPA | C01 | 3 | Nonwettable |
| 424 | PP77-1 | PPA | C01 | 5 | Nonwettable |
| 425 | PE27-1 | PEA | C01 | 1 | Nonwettable |
| 426 | PE28-1 | PEA | C01 | 3 | Nonwettable |
| 427 | PE29-1 | PEA | C01 | 5 | Nonwettable |
| 428 | PP78-1 | PPA | D03 | 3 | Wettable |
| 429 | PP79-1 | PPA | D04 | 3 | N/A[a] |
| 430 | PP80-1 | PPA | D05 | 3 | N/A |
| 431 | PP82-2 | PPA | B02 | 1.5 | Wettable |
| | | | B11 | 1.5 | |
| 432 | PP84-2 | PPA | B06 | 1.5 | Wettable |
| | | | B10 | 1.5 | |
| 433 | PP86-2 | PPA | B10 | 1.5 | Wettable |
| | | | B11 | 1.5 | |
| 434 | PP90-3 | PPA | B04 | 0.33 | Wettable |
| | | | B05 | 0.33 | |
| | | | C01 | 0.33 | |
| 435 | PP92-3 | PPA | B04 | 1 | Wettable |
| | | | B05 | 1 | |
| | | | C01 | 1 | |

TABLE 37-continued

Summary of Meltblowing Trials on
Pilot-Scale Coforming Apparatus

| Example | Comp. Code | Polymer Code | Additive(s) Code(s) | Wt. % | Wettability |
|---|---|---|---|---|---|
| 436 | PP93-3 | PPA | B04 | 1.67 | Wettable |
|  |  |  | B05 | 1.67 |  |
|  |  |  | C01 | 1.67 |  |
| 437 | PE30-3 | PEA | B04 | 0.33 | Wettable |
|  |  |  | B05 | 0.33 |  |
|  |  |  | C01 | 0.33 |  |
| 438 | PE31-3 | PEA | B04 | 1 | Wettable |
|  |  |  | B05 | 1 |  |
|  |  |  | C01 | 1 |  |
| 439 | PE32-3 | PEA | B04 | 1.67 | Wettable |
|  |  |  | B05 | 1.67 |  |
|  |  |  | C01 | 1.67 |  |

[a]Not applicable.

The results of the meltblowing trials on the coforming apparatus with additives which impart water wettability to the surfaces of the fibers were consistent with those of the previous meltblowing trials.

In order to verify the presence of additive D04 on the surfaces of the fibers, ESCA and bulk elemental analyses were run on the web from Example 429. Similar analyses were carried out with the web from Example 430 as a control. The results of these analyses are summarized in Table 38.

TABLE 38

Summary of ESCA and Bulk Analyses
on the Webs from Examples 429 and 430

|  | ESCA Data | | | Bulk Elemental Analyses | | |
|---|---|---|---|---|---|---|
| Example | % C | % F | % Si | % C | % F | % Si |
| 429 | 73 | 11 | 6.9 | 83.66 | 0.99 | 0.50 |
| 430 | 69 | — | 16 | 84.72 | — | 1.06 |
| Control[a] | 100 | — | — | 98 | — | — |

[a]Polymer PPA which did not contain any additive.

According to the analytical data for the web from Example 429, it is evident that additive D04 has segregated to the surface region; i.e., the first 100 Å of the surface as measured from the interfacial surface. The web from Example 430 also contained a substantial amount of additive, in this case D05, in the same surface region.

As already pointed out, however, additive D05 moved to the surface of the fibers because it is imcompatible with the polymer. Such incompatibility resulted in poor web formation; that is, the web was characterized by nonuniform fiber diameters, an unusually high proportion of discontinuous fibers, and a substantial amount of shot. The process was characterized by a frequent, almost explosive, expulsion of polymer from the die orifices which is potentially hazardous to the operators.

E. Coformed Webs from Pilot-Scale Coforming Apparatus

Examples 440 and 441

Two fibrous coformed nonwoven webs were formed by meltblowing a composition of the present invention and incorporating polyester staple fibers therein.

Meltblowing was accomplished as described for Examples 366-439, inclusive. In each case, the polymer was PPA and the additive was B01 at a level of 3 percent by weight.

The more significant meltblowing process conditions were approximately as follows:
die tip temperature, 296°;
primary air temperature, 284°;
primary air pressure, 3.5 psig;
throughput, 179 g per cm of die width per hour;
horizontal forming distance, 51 cm; and
vertical forming distance, 43 cm.

Following the procedure illustrated by FIG. 5 of said U.S. Pat. No. 4,663,220 and described therein, 3-inch (7.6-cm) long, 40 denier per filament polyester staple (type 125, E. I. Du Pont de Nemours & Co., Inc., Wilmington, Del.) was incorporated into the stream of meltblown fibers prior to deposition upon the forming drum. The polyester fibers were first formed by a Rando Webber matforming apparatus into a mat having a basis weight of about 100 g/m². The mat was fed to the picker roll by a feed roll which was positioned about 0.13 mm from the picker roll surface. The picker roll was rotating at a rate of about 3,000 revolutions per minute and fiber transporting air was supplied to the picker roll at a pressure of about 2.5 psig. While actual measurement of the position of the nozzle of the coform apparatus with respect to the stream of meltblown fiber was not made, it was estimated to be about 5.1 cm below and about 5.1 cm away from the die tip of the meltblowing die.

Two coformed webs were prepared, both of which had a width (cross-machine direction) of about 51 cm. The first web was composed of about 70 percent by weight of the polyester staple fibers and about 30 percent by weight of the meltblown fibers and the second web was composed of about 50 percent by weight of each of the two types of fibers. Each web had a basis weight of about 100 g/m² and wet immediately when subjected to the water drop test.

Although not described in detail here, other coformed webs were similarly prepared with staple fiber:-meltblown fiber ratios of 85:15, 75:25, 65:35, and 15:85. In addition, webs utilizing other sources of polyester staple fibers were prepared at each of the foregoing ratios. Such other polyester staple fibers were as follows:

3.25-inch (8.3-cm)×25 denier (Eastman Chemical Products, Inc., Kingsport, Tenn.);

type ES 1.5-inch (3.8-cm)×1.5 denier (Chisso Corporation, Tokyo, Japan); and type 41-D 1.5-inch (3.8-cm)×1.5 denier (Eastman Chemical Products, Inc.).

Example 441

The procedure of Examples 440 and 441 was repeated, except that the composition was 3 percent by weight of additive B01 in polymer PEA, the secondary fibers were wood pulp fibers, and a dual meltblowing die/center secondary fiber duct arrangement was employed. The composition was meltblown through one die at a throughout of either 179 or 894 g per cm per hour. In either case, the melt temperature was about 288°. The die tip pressure was either 90 or 220 psig, depending upon the throughput.

Polymer PPC was meltblown through the other die at a throughput of from about 179 to about 716 g per cm per hour. The melt temperature was in the range of from about 246° to about 274° and the primary air temperature was in the range of from about 280° to about 302°. The primary air pressure was in the 2-5 psig range.

Coformed webs containing pulp:polymer ratios of 70:30 and 90:10 were prepared. The webs wet immediately and the composition did not impede the absorbancy of the web.

V. Preparation of Cast Films

Examples 443-445

Cast films were prepared on a cast film pilot line consisting essentially of a Hexco extruder having an 8.9-cm diameter barrel, an all-purpose mixing screw, and a length-to-diameter ratio of 24 (Hexco, Inc., Addison, Ill.). The die was a 91-cm wide coathanger manifold, standard sheet die (EDI Ultraflex H-40, Extrusion Dies, Inc., Chippewa Falls, Wis.). The chill roll and take-away system consisted of two 50.8-cm outer diameter, 91-cm wide rolls with matte finishes, water cooled or heated. The winder was a Model 191-W winder and take-away system manufactured by Gloucester Engineering Co., Gloucester, Mass. The resin feeders were Conair automatic pneumatic-type resin loaders.

Three films were prepared as summarized in Table 39. In each case, the melt temperature was about 216° and the die temperature was 216°-219°. The chill rolls were maintained at temperatures of 16° and 21°, respectively.

TABLE 39

Summary of Cast Films

| Example | Polymer Code | Additive Code | Wt. Percent |
|---------|--------------|---------------|-------------|
| 443 | PPF | A11 | 1 |
| 444 | PPF | A11 | 3 |
| 445 | PEB | A11 | 1 |

Film preparation in general was routine, although barrel preessure decreased upon switching to the higher level of additive. Attempts to cast a film with polymer PPF and 5 percent by weight additive A11 and films from polymer PEB with higher levels of additive PEB were unsuccessful because of a loss of extruder pressure resulting from an inappropriate extruder screw design for the polymers and additive levels employed (no difficulties were encountered in compounding compositions in the pilot-scale apparatus, regardless of the polymer or additive level). All of the films prepared were wettable.

The films were subjected to both ESCA and bulk elemental analyses. The results are summarized in Table 40.

TABLE 40

Summary of ESCA Data and Elemental Analyses for the Cast Films of Examples 442-444

| Example | ESCA Data | | | Bulk Elemental Analyses | | |
|---------|-----------|---|---|------------------------|---|---|
| | % C | % O | % Si | % C | % H | % Si |
| 443 | 80 | 13 | 7.2 | 85.85 | 14.13 | 0.22 |
| 444 | 71 | 20 | 8.9 | 84.87 | 13.32 | 0.42 |
| 445 | 64 | 24 | 13 | 85.73 | 13.71 | 0.13 |

The analytical data summarized in Table 40 demonstrate that the additive in each case segregated to the film surface. Thus, the behavior of the additives is the same for both films and fibers.

VI. Evaluation of Known Material

In conclusion, an additive of the type described in U.S. Pat. No. 4,659,777 was evaluated both in melt-pressed films and fibers from the bench-scale meltblowing apparatus. The additive was a poly(2-ethyloxazoline)polydimethylsiloxane-poly(2-ethyloxazoline) block copolymer, each of the blocks having a molecular weight of about 3,000.

Example 446

A melt-pressed film was prepared successfully as described for Examples 131-176, inclusive. The material contained 10 percent by weight of the additive in polymer PPA.

The surface energy of the film was estimated by means of Pillar wetting agents (Pillar Corporation, West Allis, Wis.) to be 34-35 dynes per cm. The value for virgin polymer is about 30. The film then was subjected to ESCA analysis. None of the additive was found to be in the first 100 Å below the interfacial surface.

Example 447

Meltblown fibers were prepared with a bench-scale apparatus as described for Examples 178-239, inclusive. The composition consisted of 3 percent by weight of the additive in polymer PPA. Meltblowing was conducted at an air pressure of 35 psig and melt temperatures of 264, 285, and 308°. Although webs were obtained in each case, web quality was poor and decomposition of the additive occurred at each melt temperature. Decomposition was especially severe at the highest temperature. No analyses of the webs were attempted since the additive obviously is unsuited for melt-processing procedures and does not segregate to the surface.

Figure 12A:
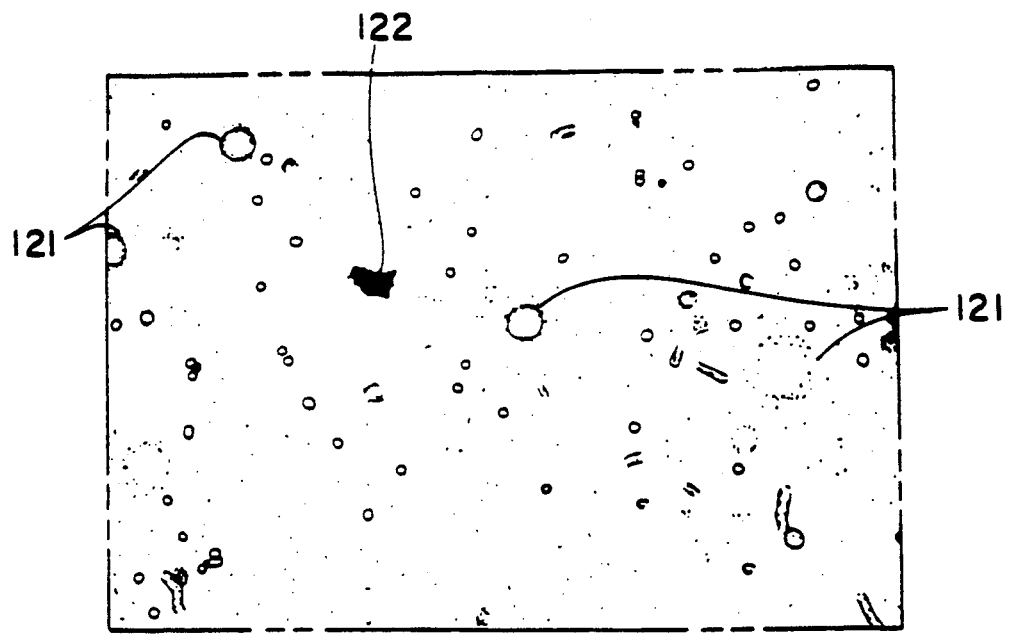
FIG. 12 consists of two hand-drawn representations of photomicrographs of a composition consisting of the polymer component of the fibers of Example 328 and a surfactant commonly used in a blooming process to render polypropylene fibers wettable, taken through a hot-stage microscope at two different temperatures and a magnification of 350×.
Figure 12B:
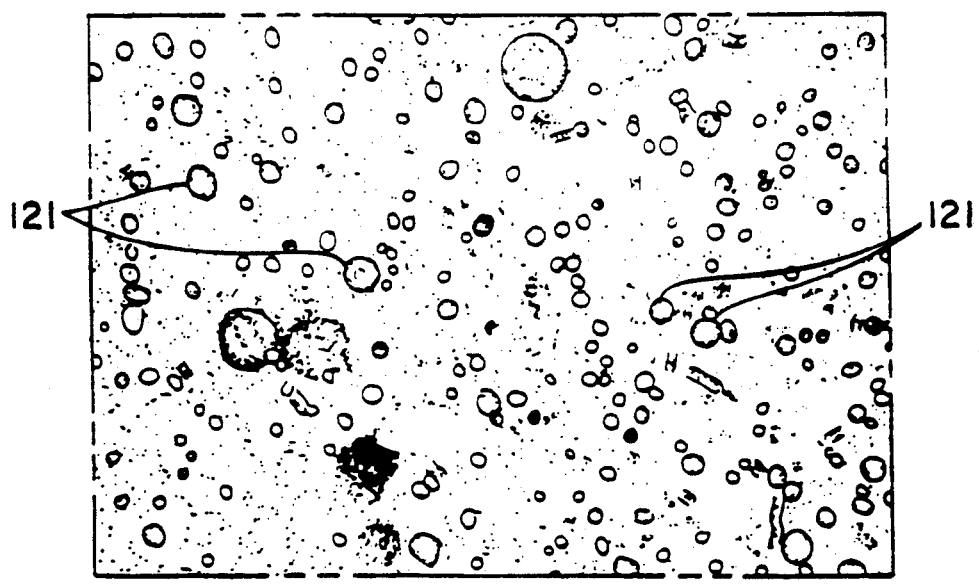

One last hot-stage microscope analysis is conveniently described here. The composition consisted of polymer PPA with 3 percent by weight of TRITON X-102 (Rohm and Haas Co.), a surfactant which is commonly used to make polypropylene wettable by means of the blooming technique already described; see U.S. Pat. No. 4,070,218. The representations of the photomicrographs are shown in FIGS. 12A and 12B. Globules 121 of the surfactant are seen in both Figures; some debris 122 in FIG. 12A also is apparent. The most noteworthy fact about the two Figures is that the surfactant not only is incompatible with the polymer at 160°, but is even less compatible at about 220°. In view of FIGS. 12A and 12B, it is easy to understand why a blooming process is required to bring the surfactant to the surface of the fiber or film and why the material migrates back into the polymer.

It now should be evident that the additives described herein and the compositions of the present invention function in a manner which is different from the materials previously added to thermoplastic polymers to alter the surface characteristics of shaped articles, such as fibers and films, made therefrom. Moreover, the compositions of the present invention permit the control of the segregation phenomenon, which control was not possible with prior art procedures.

Having thus described the invention, numerous changes and modifications thereof will be readily apparent to those having ordinary skill in the art without departing from the spirit or scope of the invention. For example, the compositions of the present invention also can contain fillers, delustrants, colorizers, stabilizers, and the like.

What is claimed is:

1. A fiber or film made from a surface-segregatable, melt-extrudable thermoplastic composition which comprises at least one thermoplastic polymer and at least one additive having at least two moieties, A and B, in which:
- (A) said additive is compatible with said polymer at melt extrusion temperatures but is incompatible at temperatures below melt extrusion temperatures, but each of moiety A and moiety B, if present as separate compounds, would be incompatible with said polymer at melt extrusion temperatures and at temperatures below melt extrusion temperatures;
- (B) moiety B has at least one functional group which imparts to said additive at least one desired characteristic;
- (C) the molecular weight of said additive is in the range of from about 400 to about 15,000; and
- (D) the weight ratio of said polymer to said additive is in the range of from about 1 to about 1,000;

with the proviso that said additive cannot be a compound having the general formula,

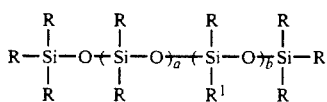

in which each R independently is a monovalent alkyl group; $R^1$ is a monovalent organic group containing at least one ethyleneoxy group, vicinal epoxy group, or amino group; and a and b, which can be the same or different, each has a value of at least 1.

2. A nonwoven web comprising fibers made from a surface-segregatable, melt-extrudable thermoplastic composition which comprises at least one thermoplastic polymer and at least one additive having at least two moieties, A and B, in which:
- (A) said additive is compatible with said polymer at melt extrusion temperatures but is incompatible at temperatures below melt extrusion temperatures, but each of moiety A and moiety B, if present as separate compounds, would be incompatible with said polymer at melt extrusion temperatures and at temperatures below melt extrusion temperatures;
- (B) moiety B has at least one functional group which imparts to said additive at least one desired characteristic;
- (C) the molecular weight of said additive is in the range of from about 400 to about 15,000; and
- (D) the weight ratio of said polymer to said additive is in the range of from about 1 to about 1,000;

with the proviso that said additive cannot be a compound having the general formula,

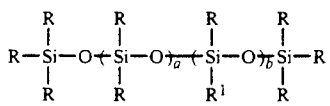

in which each RT independently is a monovalent alkyl group; $R^1$ is a monovalent organic group at least one ethyleneoxy group, vicinal epoxy group, or amino group; and a and b, which can be the same or different, each has a valve of at least 1.

3. The nonwoven web of claim 2, in which the at least one additive migrated upon formation of the fibers by melt extrusion primarily to at least one of the effective surface and the interfacial surface of the fibers.

4. The nonwoven web of claim 3, in which a characteristic of said moiety B is hydrophilicity.

5. The nonwoven web of claim 2, in which the at least one additive migrated upon formation of the fibers by melt extrusion primarily to the subsurface of the fibers.

6. The nonwoven web of claim 5, in which a characteristic of said moiety B is hydrophilicity.

7. A disposable absorbent product, at least one component of which is the nonwoven web of claim 2.

* * * * *

UNITED STATES PATENT AND TRADEMARK OFFICE
CERTIFICATE OF CORRECTION

PATENT NO. : 5,120,888

DATED : June 9, 1992

INVENTOR(S) : Ronald S. Nohr, John Gavin MacDonald

It is certified that error appears in the above-identified patent and that said Letters Patent is hereby corrected as shown below:

Column 5, line 7, "amine The silicone" should read --amine. The silicone--;

Column 5, line 33, "silicone. See A. J. Sabia" should read --silicone, see A. J. Sabia--;

Column 9, line 35, "$[-Si(R_{11})(B_3)-O-]_3$;" should read --$[-Si(R_{11})(B_3)-O-]_d$;--

Column 20, line 2, "$[-Si(R_9)(R_{10})-O-]_3$," should read --$[-Si(R_9)(R_{10})-O-]$ --

Column 20, line 21-22, "greater than that such" should read --greater than 1, that such--;

Column 23, line 32, "Essen. Federal" should read --Essen, Federal--;

Column 28, line 34 & 35, "phenylalkyl, alkyl; (b)" should read --phenylalkyl; (b)--;

Column 30, line 42, "coupled to a silicon atom" should read --coupled to a silicon atom.--;

Column 30, line 58, "be readily. Apparent" should read --be readily apparent.--;

Column 32, line 37, "with U.S. Pat. No. 1,100,324." should read --with U.S. Pat. No. 4,100,324.--;

UNITED STATES PATENT AND TRADEMARK OFFICE
CERTIFICATE OF CORRECTION

PATENT NO. : 5,120,888

DATED : June 9, 1992

INVENTOR(S) : Ronald S. Nohr, John Gavin MacDonald

It is certified that error appears in the above-identified patent and that said Letters Patent is hereby corrected as shown below:

Column 35, line 9, "In degrees C., of a 1 percent by weight solution." should read --In degrees C, of a 1 percent by weight aqueous solution.--;

Column 35, line 10, "At 20° C., ± 0.005." should read --At 20° C, ± 0.005.--;

Column 35, line 34, "In degrees C., of a" should read --In degrees C, of a--;

Column 35, line 35, "At 20° C., ± 0.005." should read --At 20° C, ± 0.005.--;

Column 35, line Table 7 Do3$^e$, "Missing $CH_2$ between O and $CH-CH_2-N[CH(CH_3)_2]_2$"

Column 36, line 24, "$^f$D-1059." should be --$^f$D-1059,--;

Column 36, line 28, "Petrarch Systems. Bristol. Pennsylvania." should read --Petrarch Systems, Bristol, Pennsylvania.--;

Column 36, line 39, "At 20° C., ± 0.005." should read --At 20° C, ± 0.005.--;

Column 36, line 53, "one of the tree necks" should read --one of the three necks--;

Column 37, line 5 & 6, "(charged by syringe injection," should read --(charged by syringe injection),--;

UNITED STATES PATENT AND TRADEMARK OFFICE
CERTIFICATE OF CORRECTION

PATENT NO. : 5,120,888

DATED : June 9, 1992

INVENTOR(S) : Ronald S. Nohr, John Gavin MacDonald

It is certified that error appears in the above-identified patent and that said Letters Patent is hereby corrected as shown below:

Column 37, line 19, "The resulting mixture was was" should read -- The resulting mixture was--;

Column 44, line 51, "surface 71 (FIG. &)" should read --surface 71 (FIG. 7)--;

Column 44, line 58, "Lakes, N.J." should read --Lakes, N.J.)--;

Column 46, line 13, "173 0-14 500    30    1.0" should read --173 0-500    30    1.0--;

Column 46, line 24, "x-axis as liens which" should read --x-axis as lines which--;

Column 46, line 25, "of such liens then" should read --of such lines then--;

Column 50, line 59, "from b 'to 4 as follows:" should read --from 1 to 4 as follows:--;

Column 51, line 5 & 6, "greater detail alter. fiber" should read --greater detail later, fiber--;

Column 53, line 3, "to some extend," should read --to some extent,--;

Column 53, line 26 & 27, Add the missing footnote, --$^a$In psig.--;

Column 53, line 37, "to the higher" should read --to higher--;

UNITED STATES PATENT AND TRADEMARK OFFICE
CERTIFICATE OF CORRECTION

PATENT NO. : 5,120,888

DATED : June 9, 1992

INVENTOR(S) : Ronald S. Nohr, John Gavin MacDonald

It is certified that error appears in the above-identified patent and that said Letters Patent is hereby corrected as shown below:

Column 54, line 24, "approximately 100 A" should read --approximately 100 Å--;

Column 61, line 10, Insert the missing heading, --<u>D. Meltblown Fibers from Pilot-Scale Coforming Apparatus</u>--;

Column 61, line 14 & 15, "type described described" should read --type described--;

Column 61, line 38, "(about 1.7mm). forming" should read --(about 1.7mm). Forming--;

Column 61, line 56, "7-360 g per cam of" should read --7-360 g per cm of--;

Column 61, line 58, "wire the more" should read --with the more--;

Column 65, line 35, "barrel preesure" should read --barrel pressure--;

Signed and Sealed this

Seventh Day of December, 1993

Attest:

BRUCE LEHMAN

Attesting Officer

Commissioner of Patents and Trademarks